US010369843B2

(12) United States Patent
Yamana et al.

(10) Patent No.: US 10,369,843 B2
(45) Date of Patent: Aug. 6, 2019

(54) PRODUCTION METHOD OF RUBBER COMPOSITION FOR TIRE AND TIRE

(71) Applicant: SUMITOMO RUBBER INDUSTRIES, LTD., Kobe-shi, Hyogo (JP)

(72) Inventors: Ayuko Yamana, Kobe (JP); Yuka Yokoyama, Kobe (JP); Masako Nakatani, Kobe (JP); Takashi Miki, Kobe (JP); Takuya Horiguchi, Kobe (JP); Yoichi Mizuno, Kobe (JP); Takahiro Kawachi, Kobe (JP); Noboru Okabe, Kobe (JP); Natsuki Sugimoto, Kobe (JP); Kenichi Uesaka, Kobe (JP); Tetsuya Maekawa, Kobe (JP); Yumi Suzuki, Kobe (JP); Fumiya Kato, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days.

(21) Appl. No.: 15/519,061

(22) PCT Filed: Nov. 6, 2015

(86) PCT No.: PCT/JP2015/081343
§ 371 (c)(1),
(2) Date: Apr. 13, 2017

(87) PCT Pub. No.: WO2016/072499
PCT Pub. Date: May 12, 2016

(65) Prior Publication Data
US 2017/0225512 A1    Aug. 10, 2017

(30) Foreign Application Priority Data

| Nov. 7, 2014 | (JP) | 2014-227018 |
|---|---|---|
| Jan. 6, 2015 | (JP) | 2015-001128 |
| Jan. 6, 2015 | (JP) | 2015-001129 |
| Jan. 6, 2015 | (JP) | 2015-001130 |
| Jan. 6, 2015 | (JP) | 2015-001131 |
| Jan. 6, 2015 | (JP) | 2015-001132 |
| Jan. 6, 2015 | (JP) | 2015-001133 |
| Jan. 6, 2015 | (JP) | 2015-001134 |
| Jan. 6, 2015 | (JP) | 2015-001135 |
| Jan. 6, 2015 | (JP) | 2015-001136 |
| Jan. 6, 2015 | (JP) | 2015-001137 |

(51) Int. Cl.
| C08C 19/25 | (2006.01) |
|---|---|
| B60C 1/00 | (2006.01) |
| C08J 3/20 | (2006.01) |
| C08K 3/36 | (2006.01) |
| C08K 5/548 | (2006.01) |

(Continued)

(52) U.S. Cl.
CPC ............ B60C 1/0016 (2013.01); B29C 35/02 (2013.01); B60C 1/00 (2013.01); C07C 279/02 (2013.01); C08J 3/20 (2013.01); C08K 3/36 (2013.01); C08K 5/103 (2013.01); C08K 5/372 (2013.01); C08K 5/54 (2013.01); C08K 5/548 (2013.01); C08L 7/00 (2013.01); C08L 9/00 (2013.01); C08L 9/06 (2013.01); C08L 21/00 (2013.01); C08K 2201/006 (2013.01); C08L 2205/03 (2013.01)

(58) Field of Classification Search
CPC ........... B60C 1/00; B60C 1/0016; C08K 3/36; C08K 5/372; C08K 5/54; C08K 5/548; C08C 19/25; C08C 19/20
See application file for complete search history.

(56) References Cited

U.S. PATENT DOCUMENTS 9,023,952 B2 * 5/2015 Botti .................... B60C 1/0016
525/332.6
2002/0082334 A1    6/2002 Kobayashi et al.
(Continued)

FOREIGN PATENT DOCUMENTS

| EP | 2128186 A1 | 12/2009 |
| EP | 2784115 A1 | 10/2014 |

(Continued)

OTHER PUBLICATIONS

International Search Report, issued in PCT/JP2015/081343, dated Feb. 2, 2016.
Written Opinion of the International Searching Authority, issued in PCT/JP2015/081343, dated Feb. 2, 2016.
International Preliminary Report on Patentability and an English translation of the Written Opinion of the International Searching Authority (PCT/IB/338, PCT/IB/373 and PCT/ISA/237), dated May 18, 2017, for International Application No. PCT/JP2015/081343.
Extended European Search Report, dated May 22, 2018, for European Application No. 15856571.3.

(Continued)

*Primary Examiner* — Robert C Boyle
(74) *Attorney, Agent, or Firm* — Birch, Stewart, Kolasch & Birch LLP

(57) ABSTRACT

According to a production method of a rubber composition for tire of the present invention comprising a rubber component (A) comprising at least one selected from the group consisting of a natural rubber and a synthetic diene rubber, a filler, a coupling agent (D) of $(C_pH_{2p+1}O)_3$—Si—$(CH_2)_q$—S—CO—$C_kH_{2k+1}$, and a vulcanizing agent (E) comprising a vulcanizer and a vulcanization accelerator, the method comprising: a step X1 of kneading all amount of A, a part of the filler and a part of D, a step X2 of kneading the kneaded product of step X1, the remaining amount of the filler and D, and a step F of kneading the kneaded product of step X2 and E, it is possible to produce a rubber composition for tire in which fuel efficiency and abrasion resistance are improved in a good balance.

11 Claims, No Drawings

(51) Int. Cl.
  *C08L 7/00* (2006.01)
  *C08L 9/00* (2006.01)
  *B29C 35/02* (2006.01)
  *C07C 279/02* (2006.01)
  *C08K 5/103* (2006.01)
  *C08K 5/372* (2006.01)
  *C08K 5/54* (2006.01)
  *C08L 9/06* (2006.01)
  *C08L 21/00* (2006.01)

(56) References Cited

U.S. PATENT DOCUMENTS

| | | | |
|---|---|---|---|
| 2010/0036006 A1 | 2/2010 | Ota | |
| 2010/0190885 A1* | 7/2010 | Hua | B60C 1/0016 523/152 |
| 2013/0237637 A1* | 9/2013 | Katou | B60C 1/00 523/351 |
| 2013/0267638 A1* | 10/2013 | Katou | C08K 3/36 524/274 |
| 2013/0331498 A1* | 12/2013 | Miyazaki | B60C 1/0016 524/493 |
| 2014/0296375 A1* | 10/2014 | Dunlavy | C08K 3/36 523/156 |
| 2015/0011676 A1 | 1/2015 | Miyazaki | |

FOREIGN PATENT DOCUMENTS

| | | |
|---|---|---|
| JP | 8-230407 A | 9/1996 |
| JP | 11-130908 A | 5/1999 |
| JP | 2002-201309 A | 7/2002 |
| JP | 2005-263999 A | 9/2005 |
| JP | 2007-238803 A | 9/2007 |
| JP | 2012-25802 A | 2/2012 |
| JP | 2012-82325 A | 4/2012 |
| JP | 2012-140508 A | 7/2012 |
| JP | 2012-144619 A | 8/2012 |
| JP | 2012-214617 A | 11/2012 |
| JP | 2014-501833 A | 1/2014 |
| JP | 2014-118555 A | 6/2014 |
| JP | 2015-13974 A | 1/2015 |
| WO | WO 2012/085893 A1 | 6/2012 |
| WO | WO 2014/021002 A1 | 2/2014 |

OTHER PUBLICATIONS

Office Action dated Jun. 5, 2018 in Japanese Patent Application No. 2015-001128 with English translation.
Office Action dated Jun. 5, 2018 in Japanese Patent Application No. 2015-001134 with English translation.

* cited by examiner

PRODUCTION METHOD OF RUBBER COMPOSITION FOR TIRE AND TIRE

TECHNICAL FIELD

The present invention relates to a production method of a rubber composition for tire and a tire having a tire component composed of the rubber composition for tire produced by the production method.

BACKGROUND ART

Due to the requirement of tires having higher fuel efficiency, a rubber composition comprising silica is now used for not only a tread, but also various components of tire. However, since silica has a hydrophilic silanol group on its surface, the affinity thereof with a rubber component (particularly, a natural rubber, a butadiene rubber and a styrene butadiene rubber which are often used for a component of tire, and the like) is low compared to that of carbon black, and there is a problem that abrasion resistance and mechanical strength (tension strength and elongation at break) are inferior.

As a method for improvement by solving such problem, a method of enhancing a reaction between a rubber component and silica by use of a coupling agent is known. However, usual coupling agents have a problem that functional groups thereof react to each other before being brought into reaction with silica and coagulate, and there was a limit in an effect of dispersing silica. Also, a method of introducing a modifier which reacts with silica into a rubber component to improve reactivity between the rubber component and silica is known. However, these methods can stand further improvement in achieving both processability and fuel efficiency.

Moreover, recently, the requirement for abrasion resistance has been getting stronger in addition to fuel efficiency from the viewpoint of natural resources protection. As a method of improving abrasion resistance, a method of using particulate silica with high reinforcing effect and the like is known. However, particulate silica is generally very difficult to be dispersed in a rubber composition and there are problems that it cannot disperse enough and a coagulated mass remains and thus cannot improve abrasion resistance and mechanical strength, or even worsen these properties in some cases.

In Patent Document 1, a technique of improving fuel efficiency, wet grip performance and processability of a rubber composition in a good balance by a combined use of a specified silane coupling agent 1 and a specified silane coupling agent 2 is disclosed. However, there is still room for improvement in achieving both wet grip performance and fuel efficiency. Further, improvement of abrasion resistance is not considered.

Moreover, in the case where a large amount of silica is used for improvement of fuel efficiency, an electrical resistance of tire becomes high and thus for example, fuel may catch fire with a spark of static electricity at fuel supply of vehicle, that is to say, there is a problem in safety at use.

In Patent Document 2, a tire in which rolling resistance is reduced without reducing electrical conductivity of tire by providing a conductive membrane at a tread portion and a sidewall portion is described. However, since this technique complicates a process of tire production and has a problem in cost, a rubber composition which can easily improve fuel efficiency and electrical conductivity in a good balance is required.

PRIOR ART DOCUMENT

Patent Document

Patent Document 1: JP 2012-082325 A
Patent Document 2: JP H08-230407 A

SUMMARY OF THE INVENTION

Problem to be Solved by the Invention

An object of the present invention is to provide a production method of a rubber composition for tire in which fuel efficiency and abrasion resistance are improved in a good balance, and a tire having a tire component composed of the rubber composition for tire produced by the production method.

Means to Solve the Problem

The inventors of the present invention have conducted extensive studies and found that instead of a conventional kneading method comprising a base kneading step X of kneading components other than vulcanizing agents at a time and a finish kneading step F of adding the vulcanizing agents to the kneaded product obtained in the step X and kneading the mixture, by use of a kneading method comprising a step X1 and a step X2 in which fillers and coupling agents are divisionally added and kneaded and a step F, a coagulation of coupling agents are prevented and a reaction with the fillers is promoted, thereby solving the above problems and as a result of further studies, the inventors have succeeded in completing the present invention.

Namely, the present invention is a production method of a rubber composition for tire comprising a rubber component (A) comprising at least one selected from the group consisting of a natural rubber and a synthetic diene rubber, a filler, a coupling agent (D) represented by the following chemical formula (1), and a vulcanizing agent (E) comprising a vulcanizer and a vulcanization accelerator, the method comprising:
(step X1) a step X1 of kneading all amount of A, a part of the filler and a part of D,
(step X2) a step X2 of kneading the kneaded product of the step X1, and the remaining amount of the filler and D, and
(step F) a step F of kneading the kneaded product of the step X2 and E.

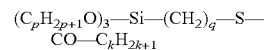
$$(C_pH_{2p+1}O)_3\text{—Si—}(CH_2)_q\text{—S—}CO\text{—}C_kH_{2k+1}$$   Chemical formula (1):

In the chemical formula (1), p represents an integer of 1 to 3, q represents an integer of 1 to 5, and k represents an integer of 5 to 12.

It is preferable that the rubber component comprises a styrene butadiene rubber and/or a butadiene rubber which has a functional group that reacts with silica.

It is preferable that the production method is a production method of the rubber composition further comprising a plasticizer and not less than 50% by mass of the total added amount of the plasticizer is kneaded in the step X1.

It is preferable that the production method is a production method of the rubber composition further comprising an anti-aging agent and the anti-aging agent is kneaded in the step X2.

The present invention also relates to a tire having a tire component composed of a rubber composition for tire produced by the above production method of a rubber composition for tire.

Effects of the Invention

The present invention is a production method of a rubber composition for tire comprising a specified rubber component (A), a filler, a specified coupling agent (D) and a vulcanizing agent (E) comprising a vulcanizer and a vulcanization accelerator, and the method comprises a specified step X1, step X2 and step F. According to the production method of a rubber composition for tire, it is possible to provide a production method of a rubber composition for tire in which fuel efficiency and abrasion resistance are improved in a good balance, and a tire having a tire component composed of the rubber composition for tire produced by the above production method.

EMBODIMENT FOR CARRYING OUT THE INVENTION

The present invention includes first to eleventh inventions. In the following, the first to eleventh inventions will be explained.

<First Invention>

The first invention is a production method of a rubber composition for tire comprising a rubber component (A-1) comprising at least two selected from the group consisting of a natural rubber and a synthetic diene rubber, silica (B-1), carbon black (C-1), a coupling agent (D-1) represented by the following chemical formula (1), and a vulcanizing agent (E-1) comprising a vulcanizer and a vulcanization accelerator, the method comprising:
(step X1-1) a step X1-1 of kneading all amount of A, a part of B-1 and a part of D-1,
(step X2-1) a step X2-1 of kneading the kneaded product of the step X1-1, the remaining amount of B-1 and D-1, and
(step F-1) a step F-1 of kneading the kneaded product of the step X2-1 and E.

            Chemical formula (1):

In the chemical formula (1), p represents an integer of 1 to 3, q represents an integer of 1 to 5, and k represents an integer of 5 to 12.

It is preferable that the rubber component comprises a styrene butadiene rubber and/or a butadiene rubber which has a functional group that reacts with silica.

It is preferable that the nitrogen adsorption specific surface area of silica is not less than 160 m²/g and the total added amount of silica is not less than 40 parts by mass based on 100 parts by mass of the rubber component.

It is preferable that the added amount of a coupling agent in each of the step X1-1 and the step X2-1 is 4 to 10 parts by mass based on 100 parts by mass of silica added in each step.

It is preferable that the added amount of silica in the step X1-1 is 50 to 95% by mass of the total added amount of silica.

It is preferable that the production method is a production method of the rubber composition further comprising a plasticizer and not less than 50% by mass of the total added amount of the plasticizer is kneaded in the step X1-1.

It is preferable that the production method is a production method of the rubber composition further comprising an anti-aging agent and the anti-aging agent is kneaded in the step X2-1.

The first invention also relates to a tire having a tire component composed of the rubber composition for tire produced by the above production method of a rubber composition for tire.

According to the first invention, it is possible to produce a rubber composition for tire in which processability, fuel efficiency and abrasion resistance are improved in a good balance. Further, by use of a tire having a tire component composed of the produced rubber composition for tire, it is possible to produce a tire in which fuel efficiency and abrasion resistance are improved in a good balance.

The rubber composition according to the first invention is characterized by comprising a specified rubber component (A-1), silica (B-1), carbon black (C-1), a specified coupling agent (D-1), and a vulcanizing agent (E-1) comprising a vulcanizer and a vulcanization accelerator.

Rubber Component (A-1)

The rubber component (A-1) is characterized by comprising at least two selected from the group consisting of a natural rubber and a synthetic diene rubber. By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The natural rubber includes a natural rubber (NR), and a modified natural rubber such as an epoxidized natural rubber (ENR), a hydrogenated natural rubber (HNR), a deproteinized natural rubber (DPNR), a high purity natural rubber (HPNR) and the like.

The NR is not limited particularly and those generally used in the tire industry such as SIR20, RSS#3, TSR20 and the like can be used.

In the case where the rubber composition comprises NR, the content thereof in the rubber component (A-1) is preferably not less than 5% by mass, more preferably not less than 10% by mass since breaking resistance of the rubber composition improves. On the other hand, the content of NR is preferably not more than 80% by mass, more preferably not more than 70% by mass, further preferably not more than 50% by mass since fuel efficiency and abrasion resistance of the rubber composition are excellent.

Examples of the synthetic diene rubber include an isoprene rubber (IR), a styrene butadiene rubber (SBR), a butadiene rubber (BR), a styrene-isoprene-butadiene rubber (SIBR) and the like.

Among synthetic diene rubbers, it is preferable that the rubber component comprises SBR since it is excellent in processability and grip performance. The SBR is not limited particularly and examples thereof include an unmodified solution-polymerized styrene-butadiene rubber (S-SBR), an unmodified emulsion-polymerized styrene-butadiene rubber (E-SBR), and modified SBRs of these (modified E-SBR, modified S-SBR) and the like. Examples of the modified SBR include a modified SBR in which a terminal and/or a main chain is modified, a modified SBR coupled by a tin or silicon compound (such as a condensate or one having a branched structure) and the like. Among these SBRs, S-SBR and a modified S-SBR are preferable since they can improve grip performance and abrasion resistance in a good balance, and from the viewpoint of the interaction with silica, a modified SBR having at least one selected from the group consisting of a silyl group, an amino group, an amide group, a hydroxyl group and an epoxy group is particularly preferable. While these SBRs can be used alone, from the viewpoint of a balance of physical properties, a combined use of SBRs having different physical properties such as a content of styrene is more preferable, depending on an application. It is noted that SBRs may be appropriately selected depending on a part to which they are applied.

The styrene content of SBR is preferably not less than 5% by mass, more preferably not less than 10% by mass, further preferably not less than 20% by mass from the viewpoint of grip performance and rubber strength. On the other hand, the styrene content of SBR is preferably not more than 60% by mass, more preferably not more than 50% by mass, further preferably not more than 40% by mass from the viewpoint of fuel efficiency. It is noted that the styrene content of SBR herein is calculated from a $^1$H-NMR measurement.

The vinyl bond amount of SBR is preferably not less than 10 mol %, more preferably not less than 15 mol %, further preferably not less than 20 mol % from the viewpoint of grip performance and rubber strength. On the other hand, the vinyl bond amount of SBR is preferably not more than 65 mol %, more preferably not more than 60 mol %, further preferably not more than 30 mol % from the viewpoint of fuel efficiency. It is noted that the vinyl bond amount of SBR herein refers to a vinyl bond amount of a butadiene part and is calculated from a $^1$H-NMR measurement.

In the case where the rubber composition comprises SBR, the content thereof in the rubber component (A-1) is preferably not less than 10% by mass, more preferably not less than 20% by mass, further preferably not less than 30% by mass from the viewpoint of grip performance. On the other hand, the content of SBR is preferably not more than 90% by mass, more preferably not more than 80% by mass from the viewpoint of abrasion resistance.

Further, it is preferable that the rubber composition comprises BR since it is excellent in abrasion resistance. In general, a rubber composition in which a white filler such as silica (B-1) is compounded in BR has a problem that dispersibility of the filler is low and it is difficult to obtain desired performance. However, in the first invention, the interaction between a filler and a rubber component is improved by divisionally kneading a specified coupling agent (D-1). Accordingly, dispersibility of a filler increases and fuel efficiency and abrasion resistance are improved as well as satisfactory processability can be obtained, thereby synergistically improving a balance among these performances.

Examples of the BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of the achievement of excellent abrasion resistance. From the viewpoint of the interaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

In the case where the rubber component comprises BR, the content thereof in the rubber component (A-1) is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 70% by mass from the viewpoint of processability.

In particular, the modified SBR or modified BR, due to a strong interaction of its functional groups, coagulates itself and dispersion of a filler usually becomes all the more difficult. However, in the first invention, by divisionally kneading a specified coupling agent (D-1), the coagulation of the rubber component is prevented and the interaction with silica is promoted.

Silica (B-1)

The silica (B-1) is not limited particularly and ones generally used in the tire industry can be used. Examples thereof include dry processed silica (silicic anhydride) and wet processed silica (hydrous silicic acid) and the like, and wet processed silica is preferable because it has more silanol groups.

The nitrogen adsorption specific surface area ($N_2SA$) of silica (B-1) is preferably not less than 40 m$^2$/g, more preferably not less than 100 m$^2$/g, further preferably not less than 130 m$^2$/g, particularly preferably not less than 160 m$^2$/g from the viewpoint of breaking strength. On the other hand, the $N_2SA$ of silica (B-1) is preferably not more than 500 m$^2$/g, more preferably not more than 300 m$^2$/g, further preferably not more than 200 m$^2$/g from the viewpoint of fuel efficiency and processability. It is noted that the $N_2SA$ of silica (B-1) herein is a value as measured with the BET method in accordance with ASTM D3037-81.

The content (total added amount) of silica (B-1) is preferably not less than 10 parts by mass, more preferably not less than 20 parts by mass, further preferably not less than 30 parts by mass, particularly preferably not less than 40 parts by mass based on 100 parts by mass of the rubber component (A-1) from the viewpoint of fuel efficiency. On the other hand, the content of the silica (B-1) is preferably not more than 200 parts by mass, more preferably not more than 150 parts by mass, further preferably not more than 100 parts by mass from the viewpoint of dispersibility of a filler into the rubber component and processability.

Carbon Black (C-1)

The carbon black (C-1) is not limited particularly and ones generally used in the tire industry such as GPF, FEF, HAF, ISAF, SAF and the like can be used, and these carbon black may be used alone, or may be used in combination with two or more thereof.

The nitrogen adsorption specific surface area ($N_2SA$) of carbon black (C-1) is preferably not less than 80 m$^2$/g, more preferably not less than 100 m$^2$/g from the viewpoint of weather resistance and antistatic performance. On the other hand, the $N_2SA$ of carbon black (C-1) is preferably not more than 200 m$^2$/g, more preferably not more than 150 m$^2$/g from the viewpoint of processability. It is noted that the $N_2SA$ of carbon black (C-1) herein is a value as measured in accordance with JIS K6217, method A.

The content (total added amount) of carbon black (C-1) is preferably not less than 1 part by mass, more preferably not less than 3 parts by mass based on 100 parts by mass of the rubber component (A-1). If the content of carbon black (C-1) is less than 1 part by mass, the effect obtained by inclusion of carbon black (C-1) may not be obtained sufficiently. On the other hand, the content of carbon black (C-1) is preferably not more than 30 parts by mass, more preferably not more than 10 parts by mass from the viewpoint of fuel efficiency and processability.

Coupling Agent (D-1)

The specified coupling agent (D-1) is a compound represented by the following chemical formula (1).

Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D-1) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and the cost.

The content of a coupling agent (D-1) represented by the chemical formula (1) is preferably not less than 4 parts by mass, more preferably not less than 5 parts by mass, further preferably not less than 6 parts by mass based on 100 parts by mass of the content of silica (C-1) from the viewpoint of the effect of improving a reaction with a filler and processability. On the other hand, the content of a coupling agent (D-1) is preferably not more than 20 parts by mass, more preferably not more than 10 parts by mass, further preferably not more than 9 parts by mass from the viewpoint of the effect of improving dispersibility of silica that is compatible with the increase of the cost.

Vulcanizing Agent (E-1)

A vulcanizing agent (E-1) comprises a vulcanizer (E1-1) and a vulcanization accelerator (E2-1). Vulcanizing agents generally used in the rubber industry such as a vulcanization accelerator auxiliary agent can be also used.

Vulcanizer (E1-1)

The vulcanizer (E1-1) is not limited particularly and ones generally used in the tire industry can be used. Since the effect of the first invention can be sufficiently obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of a vulcanizer (E1-1) is preferably not less than 0.1 part by mass, more preferably not less than 0.5 part by mass based on 100 parts by mass of the rubber component (A-1). On the other hand, the content of a vulcanizer (E1-1) is preferably not more than 15 parts by mass, more preferably not more than 5 parts by mass. If the content of a vulcanizer (E1-1) is within the above range, satisfactory tensile strength, abrasion resistance and heat resistance can be obtained.

Vulcanization Accelerator (E2-1)

The vulcanization accelerator (E2-1) is not limited particularly and ones generally used in the tire industry can be used. Example thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolesulfenamide, N-t-butyl-2-benzothiazolesulfenamide, N-oxyethylene-2-benzothiazolesulfenamide, and N,N'-diisopropyl-2-benzothiazolesulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the elastic modulus of rubber and processability are improved, and guanidine vulcanization accelerators are particularly preferable.

The content of a vulcanization accelerator (E2-1) is preferably not less than 0.1 part by mass, more preferably not less than 0.2 part by mass based on 100 parts by mass of the rubber component (A-1). On the other hand, the content of a vulcanization accelerator (E2-1) is preferably not more than 5 parts by mass, more preferably not more than 3 parts by mass. If the content of a vulcanization accelerator (E2-1) is within the above range, the reduction of the elastic modulus of rubber and the deterioration of breaking resistance can be prevented.

Other Compounding Agents

The rubber composition for tire of the first invention can suitably comprise, in addition to the above components, compounding agents that have been used in the rubber industry such as, for example, a plasticizer (F-1), a filler for reinforcement other than silica and carbon black, an anti-aging agent (G-1), an antioxidant, a stearic acid, wax and the like as necessary.

Plasticizer (F-1)

Since processability is improved and strength of rubber can be increased, it is preferable that the rubber composition for tire of the first invention comprises the plasticizer (F-1). The plasticizer (F-1) is not limited particularly and ones generally used in the tire industry can be used, and examples thereof include oil, liquid polymer, liquid resin and the like. Among these, oil is preferable since the cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as a plasticizer (F-1), the content thereof based on 100 parts by mass of the rubber component (A-1) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-1)

The anti-aging agent (G-1) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, amine anti-aging agents are preferable since these are excellent in ozone resistance and p-phenylenediamine anti-aging agents are particularly preferable.

In the case where the rubber composition comprises an anti-aging agent (G-1), the content thereof based on 100 parts by mass of the rubber component (A-1) is preferably not less than 0.5 part by mass, more preferably not less than 1.0 part by mass from the viewpoint of ozone resistance and crack resistance. On the other hand, the content of an anti-aging agent is preferably not more than 10 parts by mass, more preferably not more than 5 parts by mass from the viewpoint of the prevention of discoloration.

Production Method of Rubber Composition for Tire

The production method of a rubber composition for tire of the first invention is characterized by dividing a kneading step into a step X1-1, a step X2-1 and a step F. Known kneaders can be used in each step and examples thereof include a Banbury mixer, a kneader, an open roll and the like.

Specifically, the production method of a rubber composition for tire includes a kneading process comprising (step X1-1) of kneading all amount of a rubber component (A-1), a part of silica (B-1) and a part of a silane coupling agent (D-1), (step X2-1) of kneading the remaining amount of B-1 and D-1, and (step F-1) of kneading all amount of a vulcanizing agent (E-1) containing a vulcanizer and a vulcanization accelerator, to obtain an unvulcanized rubber composition. The obtained unvulcanized rubber composition is then vulcanized (vulcanization process) and the rubber composition for tire according to the first invention can be produced. It is noted that the timing when other compounding agents such as carbon black (C-1), a plasticizer (F-1), an anti-aging agent (G-1), a zinc oxide, a stearic acid and the like are added and kneaded is not limited particularly, and these compounding agents may be added in any of the step X1-1, the step X2-1 or the step F-1, or may be added divisionally.

The production method of the first invention is particularly characterized in that the coupling agent (D-1) represented by the chemical formula (1) is divisionally kneaded. The coupling agent (D-1) can form homogeneous chemical bonds between the filler and the polymer without losing activity even in the kneading as in the first invention where the coupling agent is divisionally input because the coupling agent does not have a plurality of alkoxysilyl groups in the molecule and the coagulation thereof is small and also because a mercapto group suitably reacting with a polymer part becomes a fatty acid thioester, thereby non-uniformity resulting from a rapid reaction is prevented.

Step X1-1

In the step X1-1, compounding agents comprising all amount of the rubber component (A-1), a part of the silica (B-1) and a part of the coupling agent (D-1) are kneaded with a Banbury mixer or the like. In this operation, the filler disperses while forming a strong bond with a rubber component, particularly with a rubber component having high affinity with the filler. Further, by use of the coupling agent (D-1) having the structure of the chemical formula (1), since thioester groups are decomposed during kneading to gradually generate mercapto groups which have high activity, it is possible to disperse the filler while maintaining processability and promote binding with the polymer. However, if a conventional polysulfide silane is used, then it releases sulfur even in this phase, thereby processability is deteriorated, a dispersion of the filler is prevented and the activity of a coupling agent itself is lowered. The coupling agent (D-1) represented by the chemical formula (1) does not release sulfur, thereby being able to continue kneading while maintaining processability.

The added amount of silica (B-1) in the step X1-1 is preferably not less than 50% by mass, more preferably not less than 60% by mass, further preferably not less than 70% by mass, particularly preferably not less than 80% by mass of the total added amount of silica (B-1) from the viewpoint of improvement of the effect of kneading silica, sufficient dispersion of silica and abrasion resistance. On the other hand, the added amount of silica (B-1) in the step X1-1 is preferably not more than 95% by mass, more preferably not more than 90% by mass of the total added amount of silica (B-1) from the viewpoint of the effect obtained by adding silica divisionally in the step X2-1 as described below, fuel efficiency and abrasion resistance.

The added amount of the coupling agent (D-1) in the step X1-1 is preferably not less than 4 parts by mass, more preferably not less than 5 parts by mass, further preferably not less than 6 parts by mass based on 100 parts by mass of the added amount of silica (B-1) in the step X1-1, since a reaction with the filler becomes sufficient and the excellent effect of improving processability of the coupling agent (D-1) can be brought out. On the other hand, the added amount of the coupling agent (D-1) in the step X1-1 is preferably not more than 20 parts by mass, more preferably not more than 10 parts by mass, further preferably not more than 9 parts by mass from the viewpoint of the effect of improving dispersibility of silica that is compatible with the increase of the cost.

It is preferable that the carbon black (C-1) is added in the step X1-1 and/or the step X2-1. The added amount of carbon black (C-1) in the step X1-1 is preferably not less than 10% by mass, more preferably not less than 50% by mass, further preferably not less than 80% by mass, most preferably 100% by mass of the total added amount of carbon black (C-1) from the viewpoint of improvement of dispersibility of carbon black and efficiency of the step. If the added amount of carbon black (C-1) in the step X1-1 is less than 100% by mass, it is preferable that the remaining amount is added in the step X2-1.

While the step in which the plasticizer (F-1) is added is not limited particularly, it is preferable that not less than 50% by mass, more preferably not less than 70% by mass, further preferably not less than 80% by mass of the total added amount of plasticizer (F-1) is added in the step X1-1. If the added amount of plasticizer (F-1) in the step X1-1 is less than 100% by mass, it is preferable that the remaining amount is added in the step X2-1 since dispersibility of the silica which is added in the step X2-1 is more improved.

Step X2-1

In the step X2-1, the remaining amount of the silica (B-1) and the coupling agent (D-1) and other compounding agents are added to the kneaded product of the step X1-1 and kneaded. If the all amount of the silica (B-1) is added in the step X1-1, the silica tends to be localized in a polymer portion having high affinity with silica such as a modified polymer and/or an interface portion of the polymer, however, in the production method of the first invention, since the silica (B-1) is divisionally added in the step X1-1 and the step X2-1, the silica (B-1) becomes easily dispersed through the entire rubber component. Further, the later added silica (B-1) (added in the step X2-1) itself has an effect of promoting kneading by applying shear to the rubber component. Moreover, in the production method of the first invention, since the coupling agent (D-1) represented by the chemical formula (1) is divisionally added, an initial reduction of the activity of the coupling agent is prevented and processability throughout the kneading operation can be maintained.

The added amount of the coupling agent (D-1) represented by the chemical formula (1) in the step X2-1 is preferably not less than 4 parts by mass, more preferably not less than 5 parts by mass, further preferably not less than 6 parts by mass based on 100 parts by mass of the added amount of the silica (B-1) in the step X2 since the reaction with a filler can be made sufficient and the excellent effect of improving processability by the coupling agent (D-1) can be brought out. On the other hand, the added amount of the coupling agent (D-1) represented by the chemical formula (1) in the step X2-1 is preferably not more than 20 parts by mass, more preferably not more than 10 parts by mass, further preferably not more than 9 parts by mass from the viewpoint of the effect of improving dispersibility of silica that is compatible with the increase of the cost.

The step in which the anti-aging agent (G-1) is added is not limited particularly, but from the viewpoint of operation efficiency and prevention of activity reduction of the anti-aging agent, it is preferable that all amount is added in the step X2-1.

The temperature at discharge of kneading in the step X1-1 and the step X2-1 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-1 and the step X2-1 is within the above range, the kneaded product in which silica is well dispersed tends to be obtained efficiently.

The kneading time in the step X1-1 and the step X2-1 is not limited particularly, but the kneading time in each step is preferably not less than 3.0 minutes, more preferably not less than 4.0 minutes, further preferably not less than 4.5 minutes. On the other hand, the kneading time in each step is preferably not more than 7.0 minutes, more preferably not more than 6.0 minutes, further preferably not more than 5.5 minutes. If the kneading time in the step X1-1 and the step X2-1 is within the above range, the kneaded product in which silica is well dispersed tends to be obtained efficiently.

Step F-1

In the step F-1, the kneaded product obtained in the step X2-1 is cooled and then the vulcanizing agent (E-1) containing a vulcanizer and a vulcanization accelerator is added and the mixture is kneaded with an open roll or the like to obtain an unvulcanized rubber composition.

It is preferable that the kneaded product obtained in the step X2-1 is normally cooled to 100° C. or less, preferably to 20 to 80° C.

The temperature at discharge of kneading in the step F-1 is preferably not higher than 110° C., more preferably not higher than 100° C. If the temperature at discharge exceeds 110° C., a rubber burning (scorch) tends to easily arise. On the other hand, the lower limit of the temperature at discharge of kneading in the step F is not limited particularly, but is preferably not lower than 80° C.

The kneading time in the step F-1 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-1 by a known method. The vulcanization temperature of the unvulcanized rubber composition is preferably not lower than 120° C., further preferably not lower than 140° C. On the other hand, the vulcanization temperature is preferably not higher than 200° C., more preferably not higher than 180° C. If the vulcanization temperature is within the above range, the effect of the first invention can be obtained successfully.

Rubber Composition for Tire

The rubber composition for tire according to the first invention can be used for any component of a tire and among these, can be suitably used for a tread since it is the rubber composition for tire in which processability, fuel efficiency and abrasion resistance are improved in a good balance.

Tire

In addition, a tire of the first invention can be produced with a normal method by use of the rubber composition for tire according to the first invention. That is, the rubber composition for tire produced by the production method of the first invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the first invention can be produced. The tire of the first invention can be suitably used for tires for passenger vehicle, tires for bus, tires for truck and the like.
<Second Invention>

The second invention is a production method of a rubber composition for tire comprising a rubber component (A-2) comprising at least one selected from the group consisting of a natural rubber and a synthetic diene rubber, silica 1 (B1-2) having a nitrogen specific surface area of more than 140 m²/g, silica 2 (B2-2) having a nitrogen specific surface area of not more than 140 m²/g, carbon black (C-2), a coupling agent (D-2) represented by the following chemical formula (1), and a vulcanizing agent (E-2) comprising a vulcanizer and a vulcanization accelerator, the method comprising:
(step X1-2) a step X1-2 of kneading A-2, B1-2, a part of D-2 and optionally a part of E-2,
(step X2-2) a step X2-2 of kneading the kneaded product of step X1-2, B2-2, the remaining amount of D-2 and optionally a part of E-2, and
(step F-2) a step F-2 of kneading the kneaded product of step X2-2 and the remaining amount of E.

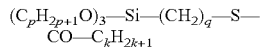

Chemical formula (1):

In the chemical formula (1), p represents an integer of 1 to 3, q represents an integer of 1 to 5, and k represents an integer of 5 to 12.

It is preferable that the rubber component comprises a styrene butadiene rubber and/or a butadiene rubber which has a functional group that reacts with silica.

It is preferable that the nitrogen adsorption specific surface area of silica 1 is not less than 160 m²/g.

It is preferable that the added amount of a coupling agent in each of the step X1-2 and the step X2-2 is 4 to 10 parts by mass based on 100 parts by mass of silica added in each step.

It is preferable that the added amount of silica 1 is 10 to 95% by mass of the total added amount of silica.

It is preferable that the production method is a production method of the rubber composition further comprising a plasticizer and not less than 50% by mass of the total added amount of a plasticizer is kneaded in the step X1-2.

It is preferable that the highest temperature in the step X1-2 and/or the step X2-2 is 140 to 200° C.

It is preferable that the production method comprises a step of keeping the kneaded product at 150 to 190° C. for 10 to 120 seconds after completion of the kneading in the step X1-2 and/or the step X2-2.

It is preferable that a part or all amount of a vulcanization accelerator is kneaded in the step X1-2 and/or the step X2-2.

It is preferable that the production method is a production method of the rubber composition further comprising an anti-aging agent and an anti-aging agent is kneaded in the step X2-2.

It is preferable that the production method is a production method of the rubber composition further comprising a surfactant and the surfactant is kneaded in the step X1-2 and/or the step X2-2.

The second invention also relates to a tire having a tire component composed of the rubber composition for tire produced by the above production method of the rubber composition for tire.

According to the second invention, it is possible to produce a rubber composition for tire in which fuel efficiency, abrasion resistance and wet grip performance are improved in a good balance. Further, by use of a tire having a tire component composed of the produced rubber composition for tire, it is possible to produce a tire in which fuel efficiency, abrasion resistance and wet grip performance are improved in a good balance.

The rubber composition for tire according to the second invention is characterized by comprising a specified rubber component (A-2), silica 1 (B1-2) and silica 2 (B2-2) respectively having a specified nitrogen adsorption specific surface area, carbon black (C-2), a specified coupling agent (D-2), and a vulcanizing agent (E-2) comprising a vulcanizer and a vulcanization accelerator.

Rubber Component (A-2)

The rubber component (A-2) is characterized by comprising at least one selected from the group consisting of a natural rubber and a synthetic diene rubber, preferably comprising two or more thereof. By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The natural rubber includes a natural rubber (NR), and a modified natural rubber such as an epoxidized natural rubber (ENR), a hydrogenated natural rubber (HNR), a deproteinized natural rubber (DPNR), a high purity natural rubber (HPNR) and the like.

The NR is not limited particularly and those generally used in the tire industry such as SIR20, RSS#3, TSR20 and the like can be used.

In the case where the rubber composition comprises NR, the content thereof in the rubber component (A-2) is preferably not less than 5% by mass, more preferably not less than 10% by mass since breaking resistance of the rubber composition improves. On the other hand, the content of NR is preferably not more than 80% by mass, more preferably not more than 70% by mass, further preferably not more than 50% by mass since fuel efficiency and abrasion resistance are excellent.

Examples of the synthetic diene rubber include an isoprene rubber (IR), a styrene butadiene rubber (SBR), a butadiene rubber (BR), a styrene-isoprene-butadiene rubber (SIBR) and the like.

Among synthetic diene rubbers, it is preferable that the rubber composition comprises SBR since it is excellent in processability and grip performance. The SBR is not limited particularly and examples thereof include an unmodified solution-polymerized styrene-butadiene rubber (S-SBR), an unmodified emulsion-polymerized styrene-butadiene rubber (E-SBR), and modified SBRs of these (modified E-SBR, modified S-SBR) and the like. Examples of the modified SBR include a modified SBR in which a terminal and/or a main chain is modified, a modified SBR coupled by a tin or silicon compound (such as a condensate or one having a branched structure) and the like. Among these SBRs, S-SBR and a modified S-SBR are preferable since they can improve grip performance and abrasion resistance in a good balance, and from the viewpoint of a reaction with silica, a modified SBR having at least one selected from the group consisting of a silyl group, an amino group, an amide group, a hydroxyl group and an epoxy group is particularly preferable. While these SBRs can be used alone, a combined use of SBRs having different physical properties such as a content of styrene is also possible depending on its application. It is noted that SBRs may be appropriately selected depending on a part to which they are applied.

The styrene content of SBR is preferably not less than 5% by mass, more preferably not less than 10% by mass, further preferably not less than 20% by mass from the viewpoint of dry grip performance, wet grip performance and the rubber strength. On the other hand, the styrene content of SBR is preferably not more than 60% by mass, more preferably not more than 50% by mass, further preferably not more than 40% by mass from the viewpoint of fuel efficiency. It is noted that the styrene content of SBR herein is calculated from a $^1$H-NMR measurement.

The vinyl bond amount of SBR is preferably not less than 10 mol %, more preferably not less than 15 mol %, further preferably not less than 20 mol % from the viewpoint of dry grip performance, wet grip performance and the rubber strength. On the other hand, the vinyl bond amount of SBR is preferably not more than 65 mol %, more preferably not more than 60 mol %, further preferably not more than 30 mol % from the viewpoint of fuel efficiency. It is noted that the vinyl bond amount of SBR herein refers to a vinyl bond amount of a butadiene part and is calculated from a $^1$H-NMR measurement.

In the case where the rubber composition comprises SBR, the content thereof in the rubber component (A-2) is preferably not less than 10% by mass, more preferably not less than 20% by mass, further preferably not less than 30% by mass from the viewpoint of dry grip performance and wet grip performance. On the other hand, the content of SBR is preferably not more than 90% by mass, more preferably not more than 80% by mass from the viewpoint of abrasion resistance.

Further, it is preferable that the rubber component comprises BR since it is excellent in abrasion resistance. In general, a rubber composition in which a white filler such as silica is compounded in a BR has a problem that dispersibility of the filler is low and it is difficult to obtain desired performance. However, in the second invention, the reaction between a filler and a rubber component is improved by divisionally kneading a specified coupling agent (D-2). Accordingly, dispersibility of a filler increases and fuel efficiency and abrasion resistance are improved as well as satisfactory processability can be obtained, thereby synergistically improving a balance among these performances.

Examples of BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

In the case where the rubber composition comprises BR, the content thereof in the rubber component (A-2) is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75% by mass, further preferably not more than 70% by mass from the viewpoint of processability.

In particular, the modified SBR or modified BR, due to a strong interaction of its functional groups, coagulates itself and dispersion of a filler usually becomes all the more difficult. However, in the second invention, by divisionally kneading a specified coupling agent (D-2), the coagulation of the rubber component is prevented and the reaction with silica is promoted.

Silica

The rubber composition for tire according to the second invention is characterized by comprising silica 1 (B1-2) having a large nitrogen adsorption specific surface area ($N_2SA$) and silica 2 (B2-2) having a small $N_2SA$ as silica. By the combined use of the silica 1 and the silica 2, processability, fuel efficiency and abrasion resistance can be improved in a good balance.

The silica 1 having a large $N_2SA$ is known as particulate silica and is generally difficult to control its dispersion. However, according to the production method of the rubber composition of the second invention, it is possible to disperse the silica well and express excellent rubber performance in a good balance.

The $N_2SA$ of the silica 1 (B1-2) is more than 140 $m^2/g$, preferably not less than 150 $m^2/g$, more preferably not less than 160 $m^2/g$. If the $N_2SA$ of the silica 1 is less than 140 $m^2/g$, the effect of improving abrasion resistance tends to be insufficient. On the other hand, the $N_2SA$ of the silica 1 is preferably not more than 500 $m^2/g$, more preferably not more than 300 $m^2/g$, further preferably not more than 250 $m^2/g$, most preferably not more than 200 $m^2/g$ from the viewpoint of low heat build-up property and processability. It is noted that the $N_2SA$ of silica herein is a value as measured with the BET method in accordance with ATSM D3037-81.

The content of the silica 1 (B1-2) based on 100 parts by mass of the rubber component is preferably not less than 10 parts by mass, more preferably not less than 15 parts by mass, further preferably not less than 20 parts by mass from the viewpoint of abrasion resistance. On the other hand, the content of the silica 1 is preferably not more than 200 parts by mass, more preferably not more than 150 parts by mass, further preferably not more than 130 parts by mass from the viewpoint of the improvement of dispersibility and the prevention of deterioration of fuel efficiency.

The $N_2SA$ of the silica 2 (B2-2) is not more than 140 $m^2/g$, preferably not more than 130 $m^2/g$, more preferably not more than 120 $m^2/g$, further preferably not more than 110 $m^2/g$ from the viewpoint of the excellent effect of improving fuel efficiency. On the other hand, the $N_2SA$ of the silica 2 is preferably not less than 40 $m^2/g$, more preferably not less than 50 $m^2/g$, further preferably not less than 60 $m^2/g$, particularly preferably not less than 70 $m^2/g$, most preferably not less than 80 $m^2/g$ from the viewpoint of the braking strength after vulcanization.

The content of the silica 2 (B2-2) based on 100 parts by mass of the rubber component is preferably not less than 3 parts by mass, more preferably not less than 5 parts by mass, further preferably not less than 10 parts by mass from the viewpoint of wet grip performance. On the other hand, the content of the silica 2 is preferably not more than 200 parts by mass, more preferably not more than 150 parts by mass, further preferably not more than 130 parts by mass from the viewpoint of the improvement of dispersibility and the prevention of deterioration of fuel efficiency.

The total content of silica is preferably not less than 10 parts by mass, more preferably not less than 20 parts by mass, further preferably not less than 30 parts by mass, particularly preferably not less than 40 parts by mass based on 100 parts by mass of the rubber component (A-2) from the viewpoint of fuel efficiency and wet grip performance. On the other hand, the total content of silica is preferably not more than 200 parts by mass, more preferably not more than 150 parts by mass, further preferably not more than 130 parts by mass from the viewpoint of dispersibility of a filler into the rubber component and processability.

The content of the silica 1 (B1-2) in the total silica is preferably not less than 10% by mass, more preferably not less than 15% by mass, further preferably not less than 20% by mass from the viewpoint of abrasion resistance and the effect of kneading in the step X1-2 as described below. On the other hand, the content of the silica 1 in the total silica is preferably not more than 95% by mass, more preferably not more than 90% by mass, further preferably not more than 80% by mass from the viewpoint of the effect of improving fuel efficiency by the silica 2.

Carbon Black (C-2)

The carbon black (C-2) is not limited particularly and ones generally used in the tire industry such as GPF, FEF, HAF, ISAF, SAF and the like can be used, and these carbon black may be used alone, or may be used in combination with two or more thereof.

The nitrogen adsorption specific surface area ($N_2SA$) of carbon black (C-2) is preferably not less than 80 m$^2$/g, more preferably not less than 100 m$^2$/g from the viewpoint of weather resistance and antistatic performance. On the other hand, the $N_2SA$ of carbon black (C-2) is preferably not more than 200 m$^2$/g, more preferably not more than 150 m$^2$/g from the viewpoint of processability. It is noted that the $N_2SA$ of carbon black (C-2) herein is a value as measured in accordance with JIS K6217, method A.

The content (total added amount) of carbon black (C-2) is preferably not less than 1 part by mass, more preferably not less than 3 parts by mass based on 100 parts by mass of the rubber component (A-2). If the content of carbon black (C-2) is less than 1 part by mass, the effect obtained by inclusion of carbon black (C-2) may not be obtained sufficiently. On the other hand, the content of carbon black (C-2) is preferably not more than 30 parts by mass, more preferably not more than 10 parts by mass from the viewpoint of fuel efficiency and processability.

Coupling Agent (D-2)

The specified coupling agent (D-2) is a compound represented by the following chemical formula (1).

Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D-2) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and cost. It is also possible that the coupling agent is used together with a general coupling agent other than the coupling agent (D) represented by the chemical formula (1).

The total content of the coupling agent (D-2) represented by the chemical formula (1) is preferably not less than 4 parts by mass, more preferably not less than 5 parts by mass, further preferably not less than 6 parts by mass based on 100 parts by mass of the total content of the silica from the viewpoint of the effect of improvement of a reaction with a filler and processability. On the other hand, the content of the coupling agent (D-2) is preferably not more than 20 parts by mass, more preferably not more than 10 parts by mass, further preferably not more than 9 parts by mass from the viewpoint of the effect of improving dispersibility of silica that is compatible with the increase of cost.

Vulcanizing Agent (E-2)

The vulcanizing agent (E-2) comprises a vulcanizer (E1-2) and a vulcanization accelerator (E2-2). Vulcanizing agents generally used in the rubber industry such as a vulcanization accelerator auxiliary agent can be also used.

Vulcanizer (E1-2)

The vulcanizer (E1-2) is not limited particularly and ones generally used in the tire industry can be used. Since the effect of the second invention can be successfully obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of the vulcanizer (E1-2) is preferably not less than 0.1 part by mass, more preferably not less than 0.5 part by mass based on 100 parts by mass of the rubber component (A-2). On the other hand, the content of the vulcanizer (E1-2) is preferably not more than 15 parts by mass, more preferably not more than 5 parts by mass. If the content of the vulcanizer (E1-2) is within the above range, satisfactory tensile strength, abrasion resistance and heat resistance can be obtained.

Vulcanization Accelerator (E2-2)

The vulcanization accelerator (E2-2) is not limited particularly and ones generally used in the tire industry can be used. Example thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolsulfenamide, N-t-butyl-2-benzothiazolsulfenamide, N-oxyethylene-2-benzothiazolsulfenamide, and N,N'-diisopropyl-2- benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-2) is preferably not less than 0.1 part by mass, more preferably not less than 0.2 part by mass based on 100 parts by mass of the rubber component (A-2). On the other hand, the content of the vulcanization accelerator (E2-2) is preferably not more than 5 parts by mass, more preferably not more than 3 parts by mass. If the content of the vulcanization accelerator (E2-2) is within the above range, the reduction of the elastic modulus of rubber and the deterioration of breaking resistance can be prevented.

Other Compounding Agents

The rubber composition for tire of the second invention can suitably comprise, in addition to the above components, compounding agents that have been used in the rubber industry such as, for example, a plasticizer (F-2), a filler for reinforcement other than silica and carbon black, an anti-aging agent (G-2), an antioxidant, a stearic acid, wax and the like as necessary.

Plasticizer (F-2)

Since processability is improved and the strength of rubber can be increased, it is preferable that the rubber composition for tire of the second invention comprises the plasticizer (F-2). The plasticizer (F-2) is not limited particularly and ones generally used in the tire industry can be used, and examples thereof include oil, liquid polymer, liquid resin and the like. Among these, oil is preferable since cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, camellia oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as a plasticizer (F-2), the content thereof based on 100 parts by mass of the rubber component (A-2) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-2)

The anti-aging agent (G-2) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises an anti-aging agent (G-2), the content thereof based on 100 parts by mass of the rubber component (A-2) is preferably not less than 0.5 part by mass, more preferably not less than 1.0 part by mass from the viewpoint of ozone resistance and crack resistance. On the other hand, the content of an anti-aging agent is preferably not more than 10 parts by mass, more preferably not more than 5 parts by mass from the viewpoint of the prevention of discoloration.

Surfactant

In an embodiment of the second invention, it is preferable that the rubber composition further comprises a surfactant. By inclusion of a surfactant, dispersibility of the above filler comprising silica and carbon black is improved and a discoloration of the obtained rubber composition for tire due to deterioration over time can be prevented.

Examples of the surfactant include metallic soap such as a metallic salt of an organic acid, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of a surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-2) from the viewpoint of the effect of improving dispersibility of silica. On the other hand, the content of a surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

Production Method of Rubber Composition for Tire

The production method of a rubber composition for tire of the second invention is characterized by dividing a kneading step into a step X1-2, a step X2-2 and a step F-2. Known kneaders can be used in each step and examples thereof include a Banbury mixer, a kneader, an open roll and the like.

Specifically, the production method of a rubber composition for tire includes a kneading process comprising (step X1-2) of kneading A-2, B1-2, a part of D2 part of D-2 and optionally a part of E-2, (step X2-2) of kneading the kneaded product of the step X1-2, B2-2, the remaining amount of D-2 and optionally a part of E-2, and (step F-2) of kneading the kneaded product of the step X2-2 and the remaining amount of E-2, to obtain an unvulcanized rubber composition. The obtained unvulcanized rubber composition is then vulcanized (vulcanization process) and the rubber composition for tire according to the second invention can be produced. It is noted that the timing when other compounding agents such as carbon black (C-2), a plasticizer (F-2), an anti-aging agent (G-2), a zinc oxide, a stearic acid and the like are added and kneaded is not limited particularly, and these compounding agents may be added in any of the step X1-2, the step X2-2 or the step F-2, or may be added divisionally.

The production method of the second invention is characterized in that the silica 1 and the silica 2 are respectively added divisionally in the step X1-2 and the step X2-2. By kneading the silica 1 which is particulate and inferior in dispersibility in the step X1-2, the whole dispersibility of silica is improved.

In addition, the production method of the second invention is characterized in that the coupling agent (D-2) represented by the chemical formula (1) is divisionally kneaded. The coupling agent (D-2) can form homogeneous chemical bonds between the filler and the polymer without losing activity even in the kneading as in the second invention where the coupling agent is divisionally added because the coupling agent does not have a plurality of alkoxysilyl groups in the molecule and the coagulation thereof is small and also because a mercapto group suitably reacting with a polymer part becomes a fatty acid thioester, thereby non-uniformity resulting from a rapid reaction is prevented.

Step X1-2

In the step X1-2, compounding agents comprising all amount of the rubber component (A-2), silica 1 (B1-2), a part of the coupling agent (D-2) and optionally a part of the vulcanizing agent (E-2) are kneaded with a Banbury mixer and the like. In this operation, the filler disperses while forming a strong bond with a rubber component, particularly with a rubber component having high affinity with the filler. Further, by use of a coupling agent (D-2) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane is used, then it releases sulfur even in this phase, thereby processability is deteriorated, dispersion of the filler is prevented and the activity of a coupling agent itself is lowered. The coupling agent (D-2) represented by the chemical formula (1) does not release sulfur, thereby being able to continue kneading while maintaining processability according to the production method of the second invention.

The added amount of the coupling agent (D-2) represented by the chemical formula (1) in the step X1-2 is preferably not less than 4 parts by mass, more preferably not less than 5 parts by mass, further preferably not less than 6 parts by mass based on 100 parts by mass of the added amount of the silica 1 (B1-2) in the step X1-2, since a reaction with the filler becomes sufficient and the excellent effect of improving processability of the coupling agent (D-2) can be brought out. On the other hand, the added amount of the coupling agent (D-2) represented by the chemical formula (1) in the step X1-2 is preferably not more than 20 parts by mass, more preferably not more than 10 parts by mass, further preferably not more than 9 parts by mass from the viewpoint of the effect of improving dispersibility of silica that is compatible with the increase of the cost.

It is preferable that the carbon black (C-2) is added in the step X1-2 and/or the step X2-2. The added amount of the carbon black (C-2) in the step X1-2 is preferably not less than 10% by mass, more preferably not less than 50% by mass, further preferably not less than 80% by mass, most preferably 100% by mass of the total added amount of the carbon black (C-2) from the viewpoint of the improvement of dispersibility of carbon black and efficiency of the step. If the added amount of the carbon black (C-2) in the step X1-2 is less than 100% by mass, it is preferable that the remaining amount is added in the step X2-2.

While the step in which the plasticizer (F-2) is added is not limited particularly, it is preferable that not less than 50% by mass, more preferably not less than 70% by mass, further preferably not less than 80% by mass of the total added amount of the plasticizer (F-2) is added in the step X1-2. If the added amount of the plasticizer (F-2) in the step X1-2 is less than 100% by mass, it is preferable that the remaining amount is added in the step X2-2 since dispersibility of the silica which is added in the step X2-2 is more improved.

It is preferable that the surfactant is added in the step X1-2 and/or the step X2-2 from the viewpoint of promoting the effect of dispersing silica, and is preferably added in the step X1-2 since the effect of dispersing silica is more promoted and a gelation of the coupling agent can be prevented.

Step X2-2

In the step X2-2, the compounding agents comprising the silica 2 (B2-2), the remaining amount of the coupling agent (D-2) and optionally a part of the vulcanizing agent (E-2) are added to the kneaded product of the step X1-2 and the mixture is kneaded. If the all amount of the silica is added in the step X1-2, the silica tends to be localized in a polymer portion having high affinity with silica such as a modified polymer and/or an interface portion of the polymer, however, in the production method of the second invention, since the silica 1 and the silica 2 are respectively added divisionally in the step X1-2 and the step X2-2, the silica becomes easily dispersed through the entire rubber component. Further, the later added silica 2 (added in the step X2-2) itself has an effect of promoting kneading by applying shear to the rubber component. Moreover, in the production method of the second invention, since the coupling agent (D-2) represented by the chemical formula (1) is divisionally added, an initial reduction of the activity of the coupling agent is prevented and processability throughout the kneading operation can be maintained.

The added amount of the coupling agent (D-2) represented by the chemical formula (1) in the step X2-2 is preferably not less than 4 parts by mass, more preferably not less than 5 parts by mass, further preferably not less than 6 parts by mass based on 100 parts by mass of the added amount of the silica 2 (B2-2) in the step X2-2 since the reaction with a filler can be made sufficient and the effect of improving excellent processability of the coupling agent (D-2) can be brought out. On the other hand, the added amount of the coupling agent (D-2) represented by the chemical formula (1) in the step X2-2 is preferably not more than 20 parts by mass, more preferably not more than 10 parts by mass, further preferably not more than 9 parts by mass from the viewpoint of the effect of improving dispersibility of silica that is compatible with the increase of the cost.

The step in which the anti-aging agent (G-2) is added is not limited particularly, but from the viewpoint of operation efficiency and prevention of activity reduction of the anti-aging agent, it is preferable that all amount is added in the step X2-2.

The temperature at discharge of kneading in the step X1-2 and the step X2-2 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-2 and the step X2-2 is within the above range, the kneaded product in which silica is well dispersed tends to be obtained efficiently.

The highest temperature during kneading in the step X1-2 and the step X2-2 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, by divisionally adding the coupling agent (D-2), a defect does not arise even if the kneading temperature becomes high and it is possible to promote the reaction of the coupling agent and promote the dispersion of the silica.

The kneading time in the step X1-2 and the step X2-2 is not limited particularly, but the kneading time in each step is preferably not less than 3.0 minutes, more preferably not less than 4.0 minutes, further preferably not less than 4.5 minutes since the kneaded product in which silica is well dispersed can be obtained efficiently. On the other hand, the respective kneading time in each step is preferably not more than 9 minutes, more preferably not more than 8 minutes, further preferably not more than 7 minutes.

In one embodiment of the second invention, it is preferable to keep the kneaded product at 150 to 190° C. for 10 to 120 seconds after the temperature reaches the highest temperature in the step X1-2 and/or the step X2-2 and the kneading is finished since the reaction between the coupling agent and the silica is completely performed.

Step F-2

In the step F-2, the kneaded product obtained in the step X2-2 is cooled and then the vulcanizing agent (E-2) containing a vulcanizer and a vulcanization accelerator is added and the mixture is kneaded with an open roll and the like to obtain an unvulcanized rubber composition.

While the vulcanizing agent (E2-2) may be added in the step F-2 at a time, it is preferable that a part or all amount is added in the step X1-2 and/or the step X2-2 and then the remaining amount is added in the step F-2. By adding a part or all amount in the step X1-2 and/or the step X2-2, dispersion between the silica and the rubber component can be promoted. It is more preferable that a part or all amount of the guanidine vulcanization accelerator is added in the step X1-2 and/or the step X2-2 since dispersibility of the silica can be more promoted.

It is preferable that the kneaded product obtained in the step X2-2 is normally cooled to 100° C. or less, preferably to 20 to 80° C.

The temperature at discharge of kneading in the step F-2 is preferably not higher than 110° C., more preferably not higher than 100° C. If the temperature at discharge exceeds 110° C., a rubber burning (scorch) tends to easily arise. On the other hand, the lower limit of the temperature at discharge of kneading in the step F-2 is not limited particularly, but is preferably not lower than 80° C.

The kneading time in the step F-2 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-2 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the second invention can be obtained successfully.

Rubber Composition for Tire

The rubber composition for tire according to the second invention can be used for any component of a tire and among these, can be suitably used for a tread or a sidewall since it is the rubber composition for tire in which processability, fuel efficiency and abrasion resistance are improved in a good balance.

Tire

In addition, a tire of the second invention can be produced with a normal method by use of the rubber composition for tire according to the second invention. That is, the rubber composition for tire produced by the production method of the second invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the second invention can be produced. It is noted that the tire of the second invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars.

<Third Invention>

The third invention is a production method of a rubber composition for tire comprising a rubber component comprising a butadiene rubber (A1-3) and a styrene butadiene rubber (A2-3), silica (B-3), carbon black (C-3), a coupling agent (D1-3) represented by the following chemical formula (1), a coupling agent (D2-3) having a sulfide group and a vulcanizing agent (E-3) comprising a vulcanizer and a vulcanization accelerator, the method comprising:

(step X1-3) a step X1-3 of kneading A1-3, a part of B-3, D1-3 and optionally a part of E-3, (step X2-3) a step X2-3 of kneading the kneaded product of step X1-3, A2-3, the remaining amount of B-3, D2-3 and optionally a part of E-3, and (step F-3) a step F-3 of kneading the kneaded product of step X2-3 and the remaining amount of E-3.

$(C_pH_{2p+1}O)_3$—Si—$(CH_2)_q$—S—CO—$C_kH_{2k+1}$    Chemical formula (1):

In the chemical formula (1), p represents an integer of 1 to 3, q represents an integer of 1 to 5, and k represents an integer of 5 to 12.

It is preferable that the butadiene rubber (A1-3) comprises a butadiene rubber which has a functional group that reacts with silica and/or a styrene butadiene rubber (A2-3) comprises a styrene butadiene rubber which has a functional group that reacts with silica.

It is preferable that the nitrogen adsorption specific surface area of silica is not less than 160 m$^2$/g and the total added amount of silica is not less than 40 parts by mass based on 100 parts by mass of the rubber component.

It is preferable that the added amount of a coupling agent in each of the step X1-3 and the step X2-3 is 4 to 10 parts by mass based on 100 parts by mass of the silica added in each step.

It is preferable that the added amount of silica in the step X1-3 is 10 to 90% by mass of the total added amount of silica.

It is preferable that the production method is a production method of the rubber composition further comprising a plasticizer and not less than 50% by mass of the total added amount of the plasticizer is kneaded in the step X1-3.

It is preferable that the highest temperature in the step X1-3 is 140 to 200° C.

It is preferable that after the kneading in the step X1-3 is finished, the production method comprises a step of keeping the kneaded product at 150 to 190° C. for 10 to 120 seconds.

It is preferable that a part or all amount of the vulcanization accelerator is kneaded in the step X1-3 and/or the step X2-3.

It is preferable that the production method is a production method of the rubber composition further comprising an anti-aging agent and the anti-aging agent is kneaded in the step X2-3.

It is preferable that the production method is a production method of the rubber composition further comprising a surfactant and the surfactant is kneaded in the step X1-3 and/or the step X2-3.

The third invention also relates to a tire having a tire component composed of the rubber composition for tire produced by the above production method of the rubber composition for tire.

According to the third invention, it is possible to produce a rubber composition for tire in which fuel efficiency, abrasion resistance and wet grip performance are improved in a good balance. Further, by use of a tire having a tire component composed of the produced rubber composition for tire, it is possible to produce a tire in which fuel efficiency, abrasion resistance and wet grip performance are improved in a good balance.

The rubber composition according to the third invention is characterized by comprising a rubber component comprising a butadiene rubber (A1-3) and a styrene butadiene rubber (A2-3), silica (B-3), carbon black (C-3), coupling agents (D1-3) and (D2-3), and a vulcanizing agent (E-3) comprising a vulcanizer and a vulcanization accelerator.

Rubber Component (A-3)

The rubber component (A-3) is characterized by comprising a butadiene rubber (A1-3) and a styrene butadiene rubber (A2-3). By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The above rubber component comprises a butadiene rubber (BR) since it is excellent in abrasion resistance. In general, a rubber composition in which a white filler such as silica (B-3) is compounded in a BR has a problem that dispersibility of the filler is low and it is difficult to obtain desired performance. However, in the third invention, the reaction between a filler and a rubber component is improved by divisionally kneading a specified coupling agent (D-3). Accordingly, dispersibility of a filler increases and fuel efficiency and abrasion resistance are improved as well as satisfactory processability can be obtained, thereby synergistically improving a balance among these performances.

Examples of the BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of the achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

The content of BR in the rubber component is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75%, further preferably not more than 70% by mass from the viewpoint of processability.

The styrene butadiene rubber (SBR) is not limited particularly and examples thereof include an unmodified solution-polymerized styrene-butadiene rubber (S-SBR), an unmodified emulsion-polymerized styrene-butadiene rubber (E-SBR), and modified SBRs of these (modified E-SBR, modified S-SBR) and the like. Examples of the modified SBR include a modified SBR in which a terminal and/or a main chain is modified, a modified SBR coupled by a tin or silicon compound (such as a condensate or one having a branched structure) and the like. Among these SBRs, S-SBR and a modified S-SBR are preferable since they can improve grip performance and abrasion resistance in a good balance, and from the viewpoint of the reaction with silica, a modified SBR having at least one selected from the group consisting of a silyl group, an amino group, an amide group, a hydroxyl group and an epoxy group is particularly preferable. While these SBRs can be used alone, a combined use of SBRs having different physical properties such as a content of styrene is also possible depending on its application. It is noted that SBRs may be appropriately selected depending on a part to which they are applied.

The styrene content of SBR is preferably not less than 5% by mass, more preferably not less than 10% by mass, further preferably not less than 20% by mass from the viewpoint of dry grip performance, wet grip performance and rubber strength. On the other hand, the styrene content of SBR is preferably not more than 60% by mass, more preferably not more than 50% by mass, further preferably not more than 40% by mass from the viewpoint of fuel efficiency. It is noted that the styrene content of the SBR herein is calculated from a $^1$H-NMR measurement.

The vinyl bond amount of SBR is preferably not less than 10 mol %, more preferably not less than 15 mol %, further preferably not less than 20 mol % from the viewpoint of dry grip performance, wet grip performance and rubber strength. On the other hand, the vinyl bond amount of SBR is preferably not more than 65 mol %, more preferably not more than 60 mol %, further preferably not more than 30 mol % from the viewpoint of fuel efficiency. It is noted that the vinyl bond amount of the SBR herein refers to a vinyl bond amount of a butadiene part and is calculated from a $^1$H-NMR measurement.

The content of SBR in the rubber component is preferably not less than 10% by mass, more preferably not less than 20% by mass, further preferably not less than 30% by mass from the viewpoint of dry grip performance and wet grip performance. On the other hand, the content of SBR is preferably not more than 90% by mass, more preferably not more than 80% by mass from the viewpoint of abrasion resistance.

In particular, the modified SBR or modified BR, due to a strong interaction of its functional groups, coagulates itself and dispersion of a filler usually becomes all the more difficult. However, in the third invention, by divisionally kneading a specified coupling agent, the coagulation of the rubber component is prevented and the reaction with silica is promoted.

The rubber component may comprise, in addition to the above BR and SBR, a natural rubber (NR), an epoxidized natural rubber (ENR), an isoprene rubber (IR), a styrene-isoprene-butadiene rubber (SIBR) and the like as necessary. If the rubber composition comprises a rubber component other than SBR and BR, the rubber component is preferably added in the step X2-3 as described below.

Silica (B-3)

The silica (B-3) is not limited particularly and ones generally used in the tire industry can be used. Examples thereof include dry processed silica (silicic anhydride) and wet processed silica (hydrous silicic acid) and the like, and wet processed silica is preferable because it has more silanol groups.

The nitrogen adsorption specific surface area ($N_2SA$) of the silica (B-3) is preferably not less than 40 m$^2$/g, more preferably not less than 50 m$^2$/g, further preferably not less than 100 m$^2$/g, particularly preferably not less than 130 m$^2$/g, most preferably not less than 160 m$^2$/g from the viewpoint of the breaking strength. On the other hand, the $N_2SA$ of the silica (B-3) is preferably not more than 500 m$^2$/g, more preferably not more than 300 m$^2$/g, further preferably not more than 250 m$^2$/g, particularly preferably not more than 200 m$^2$/g from the viewpoint of fuel efficiency and processability. It is noted that the $N_2SA$ of the silica (B-3) herein is a value as measured with the BET method in accordance with ATSM D3037-81.

The content (total added amount) of the silica (B-3) is preferably not less than 10 parts by mass, more preferably not less than 20 parts by mass, further preferably not less than 30 parts by mass, particularly preferably not less than 40 parts by mass based on 100 parts by mass of the rubber component (A-3) from the viewpoint of fuel efficiency and wet grip performance. On the other hand, the total content of the silica (B-3) is preferably not more than 200 parts by mass, more preferably not more than 150 parts by mass, further preferably not more than 120 parts by mass from the viewpoint of dispersibility of a filler into the rubber component and processability.

Carbon Black (C-3)

The carbon black (C-3) is not limited particularly and ones generally used in the tire industry such as GPF, FEF, HAF, ISAF, SAF and the like can be used, and these carbon black may be used alone, or may be used in combination with two or more thereof.

The nitrogen adsorption specific surface area ($N_2SA$) of the carbon black (C-3) is preferably not less than 80 m$^2$/g, more preferably not less than 100 m$^2$/g from the viewpoint of weather resistance and antistatic performance. On the other hand, the $N_2SA$ of the carbon black (C-3) is preferably not more than 200 m$^2$/g, more preferably not more than 150 m$^2$/g from the viewpoint of processability. It is noted that the $N_2SA$ of the carbon black (C-3) herein is a value as measured in accordance with JIS K6217, method A.

The content (total added amount) of the carbon black (C-3) is preferably not less than 1 part by mass, more preferably not less than 3 parts by mass based on 100 parts by mass of the rubber component (A-3). If the content of the carbon black (C-3) is less than 1 part by mass, the effect obtained by inclusion of the carbon black may not be obtained sufficiently. On the other hand, the content of the carbon black (C-3) is preferably not more than 30 parts by mass, more preferably not more than 10 parts by mass from the viewpoint of fuel efficiency and processability.

Coupling Agent

The coupling agent (D1-3) is a compound represented by the following chemical formula (1).

Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D1-3) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and cost.

The coupling agent (D2-3) is a coupling agent having a sulfide group and examples thereof include bis(3-triethoxysilylpropyl)tetrasulfide, bis(2-triethoxysilylethyl)tetrasulfide, bis(3-trimethoxysilylpropyl)tetrasulfide, bis(2-trimethoxysilylethyl)tetrasulfide, bis(3-triethoxysilylpropyl)trisulfide, bis(3-trimethoxysilylpropyl)trisulfide, bis(3-triethoxysilylpropyl)disulfide, bis(3-trimethoxysilylpropyl)disulfide, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 2-trimethoxysilylethyl-N,N-dimethylthiocarbamoyl tetrasulfide, 3-trimethoxysilylpropylbenzothiazolyl tetrasulfide, 3-triethoxysilylpropylbenzothiazole tetrasulfide, 3-triethoxysilylpropyl methacrylate monosulfide, 3-trimethoxysilylpropyl methacrylate monosulfide and the like. Suitable examples of these coupling agents include Si75 (bis(3-triethoxysilylpropyl)disulfide), Si69 (bis(3-triethoxysilylpropyl)tetrasulfide) manufactured by Evonik Industries, which are available as a mixture that generally has a certain distribution, and the like.

The total content of the coupling agents (D1-3) and (D2-3) is preferably not less than 4 parts by mass, more preferably not less than 5 parts by mass, further preferably not less than 6 parts by mass based on 100 parts by mass of the total content of the silica from the viewpoint of the effect of improvement of a reaction with a filler and processability. On the other hand, the total content of the coupling agents is preferably not more than 20 parts by mass, more preferably not more than 10 parts by mass, further preferably not more than 9 parts by mass from the viewpoint of the effect of improving dispersibility of silica that is compatible with the increase of cost.

Vulcanizing Agent (E-3)

The vulcanizing agent (E-3) comprises a vulcanizer (E1-3) and a vulcanization accelerator (E2-3). Vulcanizing agents generally used in the rubber industry such as a vulcanization accelerator auxiliary agent can be also used.

Vulcanizer (E1-3)

The vulcanizer (E1-3) is not limited particularly and ones generally used in the tire industry can be used. Since the effect of the third invention can be successfully obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of the vulcanizer (E1-3) is preferably not less than 0.1 part by mass, more preferably not less than 0.5 part by mass based on 100 parts by mass of the rubber component (A-3). On the other hand, the content of the vulcanizer (E1-3) is preferably not more than 15 parts by mass, more preferably not more than 5 parts by mass. If the content of the vulcanizer (E1-3) is within the above range, satisfactory tensile strength, abrasion resistance and heat resistance can be obtained.

Vulcanization Accelerator (E2-3)

The vulcanization accelerator (E2-3) is not limited particularly and ones generally used in the tire industry can be used. Example thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolsulfenamide, N-t-butyl-2-benzothiazolsulfenamide, N-oxyethylene-2-benzothiazolsulfenamide, and N,N'-diisopropyl-2-benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-3) is preferably not less than 0.1 part by mass, more preferably not less than 0.2 part by mass based on 100 parts by mass of the rubber component (A-3). On the other hand, the content of the vulcanization accelerator (E2-3) is preferably not more than 5 parts by mass, more preferably not more than 3 parts by mass. If the content of the vulcanization accelerator (E2-3) is within the above range, the reduction of the elastic modulus of rubber and the deterioration of breaking resistance can be prevented.

Other Compounding Agents

The rubber composition for tire of the third invention can suitably comprise, in addition to the above components, compounding agents that have been used in the rubber industry such as, for example, a plasticizer (F-3), a filler for reinforcement other than silica and carbon black, an anti-aging agent (G-3), an antioxidant, a stearic acid, wax and the like as necessary.

Plasticizer (F)

Since processability is improved and the strength of rubber is increased, it is preferable that the rubber composition for tire of the third invention comprises the plasticizer (F-3). The plasticizer (F-3) is not limited particularly and ones generally used in the tire industry can be used, and examples thereof include oil, liquid polymer, liquid resin and the like. Among these, oil is preferable since cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as the plasticizer (F-3), the content thereof based on 100 parts by mass of the rubber component (A-3) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-3)

The anti-aging agent (G-3) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises an anti-aging agent (G-3), the content thereof based on 100 parts by mass of the rubber component (A-3) is preferably not less than 0.5 part by mass, more preferably not less than 1.0 part by mass from the viewpoint of ozone resistance and crack resistance. On the other hand, the content of an anti-aging agent is preferably not more than 10 parts by mass, more preferably not more than 5 parts by mass from the viewpoint of prevention of discoloration.

Surfactant

In an embodiment of the third invention, it is preferable that the rubber composition further comprises a surfactant. By inclusion of the surfactant, dispersibility of the above fillers comprising silica and carbon black is improved and a discoloration of the obtained rubber composition for tire due to deterioration over time can be prevented.

Examples of the surfactant include metallic soap such as a metallic salt of an organic acid, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of the surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-3) from the viewpoint of the effect of improving dispersibility of silica. On the other hand, the content of the surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

Production Method of Rubber Composition for Tire

The production method of a rubber composition for tire of the third invention is characterized by dividing a kneading step into a step X1-3, a step X2-3 and a step F-3. Known kneaders can be used in each step and examples thereof include a Banbury mixer, a kneader, an open roll and the like.

Specifically, the production method of a rubber composition for tire includes a kneading process comprising a step X1-3 of kneading A1-3, a part of B-3, D1-3 and optionally a part of E-3, a step X2-3 of kneading the kneaded product of the step X1-3, A2-3, the remaining amount of B-3, D2-3 and optionally a part of E-3, and a step F-3 of kneading the kneaded product of the step X2-3 and the remaining amount of E-3, to obtain an unvulcanized rubber composition. The obtained unvulcanized rubber composition is then vulcanized (vulcanization process) and the rubber composition for tire according to the third invention can be produced. It is noted that the timing when other compounding agents such as carbon black (C-3), a plasticizer (F-3), an anti-aging agent (G-3), a zinc oxide, a stearic acid and the like are added and kneaded is not limited particularly, and these compounding agents may be added in any of the step X1-3, the step X2-3 or the step F-3, or may be added divisionally.

Particularly, the production method of the third invention is characterized in that the coupling agent (D1-3) is kneaded in the preceding step (step X1-3) before the coupling agent (D2-3) having a sulfide group is kneaded. The coupling agent (D1-3) can form homogeneous chemical bonds between the filler and the polymer without losing activity even in the kneading in the prior input as in the third invention because the coupling agent does not have a plurality of alkoxysilyl groups in the molecule and the coagulation thereof is small and also because a mercapto group suitably reacting with a polymer part becomes a fatty acid thioester, thereby non-uniformity resulting from a rapid reaction is prevented.

Step X1-3

In the step X1-3, compounding agents comprising the butadiene rubber (A1-3), a part of silica (B-3), the coupling agent (D1-3) and optionally a part of the vulcanizing agent (E-3) are kneaded with a Banbury mixer and the like. In this step, the filler disperses while forming a strong bond with a rubber component, particularly with a rubber component having high affinity with the filler. Further, by use of a coupling agent (D1-3) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane (coupling agent (D2-3)) is added in the step X1, then it releases sulfur even in this phase, thereby processability is deteriorated, dispersion of the filler is prevented and the activity of a coupling agent itself is lowered. The coupling agent (D1-3) represented by the chemical formula (1) does not release sulfur, thereby being able to continue kneading while maintaining processability according to the production method of the third invention.

The added amount of the silica (B-3) in the step X1-3 is preferably not less than 10% by mass, more preferably not less than 30% by mass, further preferably not less than 40% by mass, further preferably not less than 50% by mass of the total added amount of the silica (B-3) from the viewpoint of improvement of the effect of kneading silica, sufficient dispersion of silica and abrasion resistance. On the other hand, the added amount of the silica (B-3) in the step X1-3 is preferably not more than 95% by mass, more preferably not more than 90% by mass, further preferably not more than 85% by mass of the total added amount of the silica (B-3) from the viewpoint of the effect of adding silica divisionally in the step X2-3 as described below, fuel efficiency and abrasion resistance.

The added amount of the coupling agent (D1-3) represented by the chemical formula (1) in the step X1-3 is preferably not less than 4 parts by mass, more preferably not less than 5 parts by mass, further preferably not less than 6 parts by mass based on 100 parts by mass of the added amount of the silica (B-3) in the step X1-3, since a reaction with the filler becomes sufficient and the excellent effect of improving processability of the coupling agent (D1-3) can be brought out. On the other hand, the added amount of the coupling agent (D1-3) represented by the chemical formula (1) in the step X1-3 is preferably not more than 20 parts by mass, more preferably not more than 10 parts by mass, further preferably not more than 9 parts by mass from the viewpoint of the effect of improving dispersibility of silica that is compatible with the increase of the cost.

It is preferable that the carbon black (C-3) is added in the step X1-3 and/or the step X2-3. The added amount of the carbon black (C-3) in the step X1-3 is preferably not less than 10% by mass, more preferably not less than 50% by mass, further preferably not less than 80% by mass, most preferably 100% by mass of the total added amount of the carbon black (C-3) from the viewpoint of the improvement of dispersibility of carbon black and efficiency of the step. If the added amount of the carbon black (C-3) in the step X1-3 is less than 100% by mass, it is preferable that the remaining amount is added in the step X2-3.

While the step in which the plasticizer (F-3) is added is not limited particularly, it is preferable that not less than 50% by mass, more preferably not less than 70% by mass, further preferably not less than 80% by mass of the total added amount of the plasticizer (F-3) is added in the step X1-3. If the added amount of the plasticizer (F-3) in the step X1-3 is less than 100% by mass, it is preferable that the remaining amount is added in the step X2-3 since dispersibility of the silica which is added in the step X2-3 is more improved.

It is preferable that the surfactant is added in the step X1-3 and/or the step X2-3 from the viewpoint of promoting the effect of dispersing silica, and is preferably added in the step X1-3 since the effect of dispersing silica is more promoted and a gelation of the coupling agent can be prevented.

The temperature at discharge of kneading in the step X1-3 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-3 is within the above range, the kneaded product in which silica (B-3) is well dispersed tends to be obtained efficiently.

The highest temperature during kneading in the step X1-3 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, polysulfide silane is not added as a vulcanization accelerator in the step X1-3 according to the third invention and thus a defect does not arise even if the kneading temperature becomes high and it is possible to promote the reaction of the coupling agent and promote the dispersion of the silica.

The kneading time in the step X1-3 is not limited particularly, but the kneading time in each step is preferably not less than 3.0 minutes, more preferably not less than 4.0 minutes, further preferably not less than 4.5 minutes since the kneaded product in which silica is well dispersed can be obtained efficiently. On the other hand, the respective kneading time is preferably not more than 9 minutes, more preferably not more than 8 minutes, further preferably not more than 7 minutes.

In one embodiment of the third invention, it is preferable to keep the kneaded product at 150 to 190° C. for 10 to 120 seconds after the temperature reaches the highest temperature in the step X1-3 and the kneading is finished since the reaction between the coupling agent (D1-3) and the silica is completely performed.

Step X2-3

In the step X2-3, the compounding agents comprising the styrene butadiene rubber (A2-3), the remaining amount of the silica (B-3), the coupling agent (D2-3) and optionally a part of the vulcanizing agent (E-3) are added to the kneaded product of the step X1-3 and the mixture is kneaded. If the all amount of the silica is added in the step X1-3, the silica tends to be localized in a polymer portion having high affinity with silica such as SBR and/or an interface portion of the polymer, however, in the production method of the third invention, since the silica is respectively added divisionally in the step X1-3 and the step X2-3, the silica is easily dispersed through the entire rubber component. Further, the later added silica (added in the step X2-3) itself has an effect of promoting kneading by applying shear to the rubber component. Moreover, in the production method of the third invention, since the coupling agent (D1-3) represented by the chemical formula (1) is kneaded in the step X1-3, an initial reduction of the activity of the coupling agent is prevented and processability throughout the kneading operation can be maintained.

In addition, by kneading the coupling agent (D2-3) having a sulfide group in the step X2-3, an initial reduction of the activity of the coupling agent is prevented and processability throughout the kneading operation can be maintained. Moreover, since the coupling agent (D2-3) can release sulfur that acts as a vulcanizer, a uniform crosslinking is promoted and the improvement of physical properties of the rubber can be attempted.

The added amount of the coupling agent (D2-3) in the step X2-3 is preferably not less than 4 parts by mass, more preferably not less than 5 parts by mass, further preferably not less than 6 parts by mass based on 100 parts by mass of the added amount of the silica (B-3) in the step X2-3 since the reaction with a filler can be made sufficient and the excellent effect of improving processability of the coupling agent (D2-3) can be brought out. On the other hand, the added amount of the coupling agent (D2-3) represented by the chemical formula (1) in the step X2-3 is preferably not more than 20 parts by mass, more preferably not more than 10 parts by mass, further preferably not more than 9 parts by mass from the viewpoint of the effect of improving dispersibility of silica that is compatible with the increase of the cost.

The step in which the anti-aging agent (G-3) is added is not limited particularly, but from the viewpoint of operation efficiency and prevention of activity reduction of the anti-aging agent, it is preferable that all amount is added in the step X2-3.

The temperature at discharge of kneading in the step X2-3 is not limited particularly, but is preferably not lower than 100° C., more preferably not lower than 120° C., further preferably not lower than 130° C. On the other hand, the temperature at discharge is preferably not higher than 200° C., more preferably not higher than 170° C., further preferably not higher than 160° C. If the temperature at discharge in the step X2-3 is within the above range, the kneaded product in which silica (B-3) is well dispersed tends to be obtained efficiently.

The highest temperature during kneading in the step X2-3 is not limited particularly, but is preferably not lower than 100° C., more preferably not lower than 120° C., further preferably not lower than 130° C. since the coupling agent (D2-3) is sufficiently reacted and the kneaded product in which the silica is well dispersed can be obtained efficiently. On the other hand, the highest temperature during kneading is preferably not higher than 200° C., more preferably not higher than 170° C., further preferably not higher than 160° C. for preventing a rubber burning.

The kneading time in the step X2-3 is not limited particularly, but the kneading time is preferably not less than 3.0 minutes since the kneaded product in which silica is well dispersed can be obtained efficiently. On the other hand, the respective kneading time is preferably not more than 9 minutes, more preferably not more than 8 minutes, further preferably not more than 7 minutes.

Step F-3

In the step F-3, the kneaded product obtained in the step X2-3 is cooled and then the vulcanizing agent (E-3) containing a vulcanizer and a vulcanization accelerator is added and the mixture is kneaded with an open roll or the like to obtain an unvulcanized rubber composition.

While the vulcanization accelerator may be added in the step F-3 at a time, it is preferable that a part or all amount is added in the step X1-3 and/or the step X2-3 and then the remaining amount is added in the step F-3. By adding a part or all amount in the step X1-3 and/or the step X2-3, dispersion between the silica and the rubber component can be promoted more. It is more preferable that a part or all amount of the guanidine vulcanization accelerator is added in the step X1-3 and/or the step X2-3 since dispersibility of the silica can be more promoted.

It is preferable that the kneaded product obtained in the step X2-3 is normally cooled to 100° C. or less, preferably to 20 to 80° C.

The temperature at discharge of kneading in the step F-3 is preferably not higher than 110° C., more preferably not higher than 100° C. If the temperature at discharge exceeds 110° C., a rubber burning (scorch) tends to easily arise. On the other hand, the lower limit of the temperature at discharge of kneading in the step F is not limited particularly, but is preferably not lower than 80° C.

The kneading time in the step F-3 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-3 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the third invention can be obtained successfully.

Rubber Composition for Tire

The rubber composition for tire according to the third invention can be used for any component of a tire and among these, can be suitably used for a tread or a sidewall since it is the rubber composition for tire in which processability, fuel efficiency and abrasion resistance are improved in a good balance.

Tire

In addition, a tire of the third invention can be produced with a normal method by use of the rubber composition for tire according to the third invention. That is, the rubber composition for tire produced by the production method of the third invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the third invention can be produced. It is noted that the tire of the third invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars.

<Fourth Invention>

The fourth invention is a production method of a rubber composition for tire comprising a rubber component (A-4) comprising at least one selected from the group consisting of a natural rubber and a synthetic diene rubber, silica 1 (B1-4) having a nitrogen adsorption specific surface area of more than 140 $m^2/g$, silica 2 (B2-4) having a nitrogen adsorption specific surface area of not more than 140 $m^2/g$, carbon black (C-4), a coupling agent (D1-4) represented by the following chemical formula (1), a coupling agent (D2-4) having a sulfide group and a vulcanizing agent (E-4) comprising a vulcanizer and a vulcanization accelerator, the method comprising:

(step X1-4) a step X1-4 of kneading A-4, B1-4, D1-4 and optionally a part of E-4,
(step X2-4) a step X2-4 of kneading the kneaded product of the step X1-4, B2-4, D2-4, and optionally a part of E-4, and
(step F-4) a step F-4 of kneading the kneaded product of the step X2-4 and the remaining amount of E.

   Chemical formula (1):

In the chemical formula (1), p represents an integer of 1 to 3, q represents an integer of 1 to 5, and k represents an integer of 5 to 12.

It is preferable that the rubber component comprises a styrene butadiene rubber and/or a butadiene rubber which has a functional group that reacts with silica.

It is preferable that the nitrogen adsorption specific surface area of silica 1 is not less than 160 m$^2$/g.

It is preferable that the added amount of a coupling agent in each of the step X1-4 and the step X2-4 is 4 to 10 parts by mass based on 100 parts by mass of silica added in each step.

It is preferable that the added amount of silica in the step X1-4 is 50 to 95% by mass of the total added amount of silica.

It is preferable that the production method is a production method of the rubber composition further comprising a plasticizer and not less than 50% by mass of the total added amount of a plasticizer is kneaded in the step X1-4.

It is preferable that the highest temperature in the step X1-4 is 140° C. to 200° C.

It is preferable that after the kneading in the step X1-4 is finished, the production method comprises a step of keeping the kneaded product at 150 to 190° C. for 10 to 120 seconds.

It is preferable that a part or all amount of a vulcanization accelerator is kneaded in the step X1-4 and/or the step X2-4.

It is preferable that the production method is a production method of the rubber composition further comprising an anti-aging agent and an anti-aging agent in kneaded in the step X2-4.

It is preferable that the production method is a production method of the rubber further composition comprising a surfactant and the surfactant is kneaded in the step X1-4 and/or the step X2-4.

The fourth invention also relates to a tire having a tire component composed of the rubber composition for tire produced by the above production method of the rubber composition for tire.

According to the fourth invention, it is possible to produce a rubber composition for tire in which fuel efficiency, abrasion resistance and wet grip performance are improved in a good balance. Further, by use of a tire having a tire component composed of the produced rubber composition for tire, it is possible to produce a tire in which fuel efficiency, abrasion resistance and wet grip performance are improved in a good balance.

The rubber composition according to the fourth invention is characterized by comprising a specified rubber component (A-4), silica 1 (B1-4) and silica 2 (B2-4) respectively having a specified nitrogen adsorption specific surface area, carbon black (C-4), coupling agents (D1-4) and (D2-4), and a vulcanizing agent (E-4) comprising a vulcanizer and a vulcanization accelerator.

Rubber Component (A-4)

The rubber component (A-4) is characterized by comprising at least one selected from the group consisting of a natural rubber and a synthetic diene rubber, preferably comprising two or more thereof. By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The natural rubber includes a natural rubber (NR), and a modified natural rubber such as an epoxidized natural rubber (ENR), a hydrogenated natural rubber (HNR), a deproteinized natural rubber (DPNR), a high purity natural rubber (HPNR) and the like.

The NR is not limited particularly and those generally used in the tire industry such as SIR20, RSS#3, TSR20 and the like can be used.

In the case where the rubber composition comprises NR, the content thereof in the rubber component (A-4) is preferably not less than 5% by mass, more preferably not less than 10% by mass since breaking resistance of the rubber composition improves. On the other hand, the content of NR is preferably not more than 80% by mass, more preferably not more than 70% by mass, further preferably not more than 50% by mass since fuel efficiency and abrasion resistance are excellent.

Examples of the synthetic diene rubber include an isoprene rubber (IR), a styrene butadiene rubber (SBR), a butadiene rubber (BR), a styrene-isoprene-butadiene rubber (SIBR) and the like.

Among synthetic diene rubbers, it is preferable that the rubber composition comprises SBR since it is excellent in processability, dry grip performance and wet grip performance. The SBR is not limited particularly and examples thereof include an unmodified solution-polymerized styrene-butadiene rubber (S-SBR), an unmodified emulsion-polymerized styrene-butadiene rubber (E-SBR), and modified SBRs of these (modified E-SBR, modified S-SBR) and the like. Examples of the modified SBR include a modified SBR in which a terminal and/or a main chain is modified, a modified SBR coupled by a tin or silicon compound (such as a condensate or one having a branched structure) and the like. Among these SBRs, S-SBR and a modified S-SBR are preferable since they can improve grip performance and abrasion resistance in a good balance, and from the viewpoint of a reaction with silica, a modified SBR having at least one selected from the group consisting of a silyl group, an amino group, an amide group, a hydroxyl group and an epoxy group is particularly preferable. While these SBRs can be used alone, SBRs having different physical properties such as a content of styrene may be used in combination depending on its application. It is noted that SBRs may be appropriately selected depending on a part to which they are applied.

The styrene content of SBR is preferably not less than 5% by mass, more preferably not less than 10% by mass, further preferably not less than 20% by mass from the viewpoint of dry grip performance, wet grip performance and rubber strength. On the other hand, the styrene content of SBR is preferably not more than 60% by mass, more preferably not more than 50% by mass, further preferably not more than 40% by mass from the viewpoint of fuel efficiency. It is noted that the styrene content of SBR herein is calculated from a $^1$H-NMR measurement.

The vinyl bond amount of SBR is preferably not less than 10 mol %, more preferably not less than 15 mol %, further preferably not less than 20 mol % from the viewpoint of dry grip performance, wet grip performance and rubber strength. On the other hand, the vinyl bond amount of SBR is preferably not more than 65 mol %, more preferably not more than 60 mol %, further preferably not more than 30 mol % from the viewpoint of fuel efficiency. It is noted that the vinyl bond amount of SBR herein refers to a vinyl bond amount of a butadiene part and is calculated from a $^1$H-NMR measurement.

In the case where the rubber composition comprises SBR, the content thereof in the rubber component (A-4) is preferably not less than 10% by mass, more preferably not less than 20% by mass, further preferably not less than 30% by mass from the viewpoint of dry grip performance and wet grip performance. On the other hand, the content of SBR is preferably not more than 90% by mass, more preferably not more than 80% by mass from the viewpoint of abrasion resistance.

Further, it is preferable that the rubber component comprises BR since it is excellent in abrasion resistance. In general, a rubber composition in which a white filler such as silica (B-4) is compounded in BR has a problem that dispersibility of the filler is low and it is difficult to obtain desired performance. However, in the fourth invention, the reaction between a filler and a rubber component is improved by divisionally kneading a specified coupling agent. Accordingly, dispersibility of a filler increases and fuel efficiency and abrasion resistance are improved as well as satisfactory processability can be obtained, thereby synergistically improving a balance among these performances.

Examples of BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

In the case where the rubber composition comprises BR, the content thereof in the rubber component (A-4) is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75% by mass, further preferably not more than 70% by mass from the viewpoint of processability.

In particular, the modified SBR or modified BR, due to a strong interaction of its functional groups, coagulates itself and dispersion of a filler usually becomes all the more difficult. However, in the fourth invention, by divisionally kneading a specified coupling agent, the coagulation of the rubber component is prevented and the reaction with silica is promoted.

Silica

The rubber composition for tire according to the fourth invention is characterized by comprising silica 1 (B1-4) having a large nitrogen adsorption specific surface area ($N_2SA$) and silica 2 (B2-4) having a small $N_2SA$ as silica. By the combined use of the silica 1 and the silica 2, processability, fuel efficiency and abrasion resistance can be improved in a good balance.

The silica 1 having a large $N_2SA$ is known as particulate silica and is generally difficult to control its dispersion. However, according to the production method of the rubber composition of the fourth invention, it is possible to disperse the silica well and express excellent rubber performance in a good balance.

The $N_2SA$ of the silica 1 (B1-4) is more than 140 $m^2/g$, preferably not less than 150 $m^2/g$, more preferably not less than 160 $m^2/g$. If the $N_2SA$ of the silica 1 is less than 140 $m^2/g$, the effect of improving abrasion resistance tends to be insufficient. On the other hand, the $N_2SA$ of the silica 1 is preferably not more than 500 $m^2/g$, more preferably not more than 300 $m^2/g$, further preferably not more than 250 $m^2/g$, most preferably not more than 200 $m^2/g$ from the viewpoint of low heat build-up property and processability. It is noted that the $N_2SA$ of silica herein is a value as measured with the BET method in accordance with ATSM D3037-81.

The content of the silica 1 (B1-4) based on 100 parts by mass of the rubber component is preferably not less than 10 parts by mass, more preferably not less than 15 parts by mass, further preferably not less than 20 parts by mass from the viewpoint of abrasion resistance. On the other hand, the content of the silica 1 is preferably not more than 200 parts by mass, more preferably not more than 150 parts by mass, further preferably not more than 130 parts by mass from the viewpoint of the improvement of dispersibility and the prevention of deterioration of fuel efficiency.

The $N_2SA$ of the silica 2 (B2-4) is not more than 140 $m^2/g$, preferably not more than 130 $m^2/g$, more preferably not more than 120 $m^2/g$, further preferably not more than 110 $m^2/g$ from the viewpoint of the excellent effect of improving fuel efficiency. On the other hand, the $N_2SA$ of the silica 2 is preferably not less than 40 $m^2/g$, more preferably not less than 50 $m^2/g$, further preferably not less than 60 $m^2/g$, particularly preferably not less than 70 $m^2/g$, most preferably not less than 80 $m^2/g$ from the viewpoint of the braking strength after vulcanization.

The content of the silica 2 (B2-4) based on 100 parts by mass of the rubber component is preferably not less than 3 parts by mass, more preferably not less than 5 parts by mass, further preferably not less than 10 parts by mass from the viewpoint of wet grip performance. On the other hand, the content of the silica 2 is preferably not more than 200 parts by mass, more preferably not more than 150 parts by mass, further preferably not more than 130 parts by mass from the viewpoint of the improvement of dispersibility and the prevention of deterioration of fuel efficiency.

The total content of silica is preferably not less than 10 parts by mass, more preferably not less than 20 parts by mass, further preferably not less than 30 parts by mass, particularly preferably not less than 40 parts by mass based on 100 parts by mass of the rubber component (A-4) from the viewpoint of fuel efficiency and wet grip performance. On the other hand, the total content of silica is preferably not more than 200 parts by mass, more preferably not more than 150 parts by mass, further preferably not more than 130 parts by mass from the viewpoint of dispersibility of a filler into the rubber component and processability.

The content of the silica 1 (B1-4) in the total silica is preferably not less than 10% by mass, more preferably not less than 15% by mass, further preferably not less than 20% by mass from the viewpoint of abrasion resistance and the effect of kneading in the step X1-4 as described below. On the other hand, the content of the silica 1 in the total silica is preferably not more than 95% by mass, more preferably not more than 90% by mass, further preferably not more than 80% by mass from the viewpoint of the effect of improving fuel efficiency of the silica 2.

Carbon Black (C-4)

The carbon black (C-4) is not limited particularly and ones generally used in the tire industry such as GPF, FEF, HAF, ISAF, SAF and the like can be used, and these carbon black may be used alone, or may be used in combination with two or more thereof.

The nitrogen adsorption specific surface area ($N_2SA$) of the carbon black (C-4) is preferably not less than 80 $m^2/g$, more preferably not less than 100 $m^2/g$ from the viewpoint of weather resistance and antistatic performance. On the other hand, the $N_2SA$ of the carbon black (C-4) is preferably not more than 200 $m^2/g$, more preferably not more than 150 $m^2/g$ from the viewpoint of processability. It is noted that the $N_2SA$ of the carbon black (C-4) herein is a value as measured in accordance with JIS K6217, method A.

The content (total added amount) of the carbon black (C-4) is preferably not less than 1 part by mass, more preferably not less than 3 parts by mass based on 100 parts by mass of the rubber component (A-4). If the content of the carbon black (C-4) is less than 1 part by mass, the effect obtained by inclusion of the carbon black may not be obtained sufficiently. On the other hand, the content of the carbon black (C-4) is preferably not more than 30 parts by mass, more preferably not more than 10 parts by mass from the viewpoint of fuel efficiency and processability.

Coupling Agent

The above coupling agent (D1-4) is a compound represented by the following chemical formula (1).

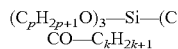
$$(C_pH_{2p+1}O)_3-Si-(CH_2)_q-S- \\ CO-C_kH_{2k+1}$$ Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D1-4) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and the cost.

The coupling agent (D2-4) is a coupling agent having a sulfide group and examples thereof include bis(3-triethoxysilylpropyl)tetrasulfide, bis(2-triethoxysilylethyl)tetrasulfide, bis(3-trimethoxysilylpropyl)tetrasulfide, bis(2-trimethoxysilylethyl)tetrasulfide, bis(3-triethoxysilylpropyl) trisulfide, bis(3-trimethoxysilylpropyl)trisulfide, bis(3-triethoxysilylpropyl)disulfide, bis(3-trimethoxysilylpropyl) disulfide, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 2-trimethoxysilylethyl-N,N-dimethylthiocarbamoyl tetrasulfide, 3-trimethoxysilylpropylbenzothiazolyl tetrasulfide, 3-triethoxysilylpropylbenzothiazole tetrasulfide, 3-triethoxysilylpropyl methacrylate monosulfide, 3-trimethoxysilylpropyl methacrylate monosulfide and the like. Suitable examples of these coupling agents include Si75 (bis(3-triethoxysilylpropyl)disulfide), Si69 (bis(3-triethoxysilylpropyl)tetrasulfide) manufactured by Evonik Industries, which are available as a mixture that generally has a certain distribution, and the like.

The total content of the coupling agents (D1-4) and (D2-4) is preferably not less than 4 parts by mass, more preferably not less than 5 parts by mass, further preferably not less than 6 parts by mass based on 100 parts by mass of the total content of silica from the viewpoint of the effect of improvement of a reaction with a filler and processability. On the other hand, the total content of the coupling agents is preferably not more than 20 parts by mass, more preferably not more than 10 parts by mass, further preferably not more than 9 parts by mass from the viewpoint of the effect of improving dispersibility of silica that is compatible with the increase of the cost.

Vulcanizing Agent (E-4)

The vulcanizing agent (E-4) comprises a vulcanizer (E1-4) and a vulcanization accelerator (E2-4). Vulcanizing agents generally used in the rubber industry such as a vulcanization accelerator auxiliary agent can be also used.

Vulcanizer (E1-4)

The vulcanizer (E1-4) is not limited particularly and ones generally used in the tire industry can be used. Since the effect of the fourth invention can be successfully obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of the vulcanizer (E1-4) is preferably not less than 0.1 part by mass, more preferably not less than 0.5 part by mass based on 100 parts by mass of the rubber component (A-4). On the other hand, the content of the vulcanizer (E1-4) is preferably not more than 15 parts by mass, more preferably not more than 5 parts by mass. If the content of the vulcanizer (E1-4) is within the above range, satisfactory tensile strength, abrasion resistance and heat resistance can be obtained.

Vulcanization Accelerator (E2-4)

The vulcanization accelerator (E2-4) is not limited particularly and ones generally used in the tire industry can be used. Examples thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2- benzothiazolsulfenamide, N-t-butyl-2-benzothiazolsulfenamide, N-oxyethylene-2-benzothiazolsulfenamide, and N,N'-diisopropyl-2-benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-4) is preferably not less than 0.1 part by mass, more preferably not less than 0.2 part by mass based on 100 parts by mass of the rubber component (A-4). On the other hand, the content of the vulcanization accelerator (E2-4) is preferably not more than 5 parts by mass, more preferably not more than 3 parts by mass. If the content of the vulcanization accelerator (E2-4) is within the above range, the reduction of the elastic modulus of rubber and the deterioration of breaking resistance can be prevented.

Other Compounding Agents

The rubber composition for tire of the fourth invention can suitably comprise, in addition to the above components, compounding agents that have been used in the rubber industry such as, for example, a plasticizer (F-4), a filler for reinforcement other than silica and carbon black, an anti-aging agent (G-4), an antioxidant, a stearic acid, wax and the like as necessary.

Plasticizer (F-4)

Since processability is improved and the strength of rubber is increased, it is preferable that the rubber composition for tire of the fourth invention comprises the plasticizer (F-4). The plasticizer (F-4) is not limited particularly and ones generally used in the tire industry can be used, and examples thereof include oil, liquid polymer, liquid resin and the like. Among these, oil is preferable since cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as the plasticizer (F-4), the content thereof based on 100 parts by mass of the rubber component (A-4) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-4)

The anti-aging agent (G-4) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises an anti-aging agent (G-4), the content thereof based on 100 parts by mass of the rubber component (A-4) is preferably not less than 0.5 part by mass, more preferably not less than 1.0 part by mass from the viewpoint of ozone resistance and crack resistance. On the other hand, the content of an anti-aging agent is preferably not more than 10 parts by mass, more preferably not more than 5 parts by mass from the viewpoint of prevention of discoloration.

Surfactant

In an embodiment of the fourth invention, it is preferable that the rubber composition further comprises a surfactant. By inclusion of a surfactant, dispersibility of the above filler comprising silica and carbon black is improved and a discoloration of the obtained rubber composition for tire due to deterioration over time can be prevented.

Examples of the surfactant include metallic soap such as a metallic salt of an organic acid, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of the surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-4) from the viewpoint of the effect of improving dispersibility of silica. On the other hand, the content of the surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

Production Method of Rubber Composition for Tire

The production method of a rubber composition for tire of the fourth invention is characterized by dividing a kneading step into a step X1-4, a step X2-4 and a step F-4. Known kneaders can be used in each step and examples thereof include a Banbury mixer, a kneader, an open roll and the like.

Specifically, the production method of a rubber composition for tire includes a kneading process comprising a step X1-4 of kneading A-4, B1-4, D1-4 and optionally a part of E-4, a step X2-4 of kneading the kneaded product of the step X1-4, B2-4, D2-4 and optionally a part of E-4, and a step F-4 of kneading the kneaded product of the step X2-4 and the remaining amount of E-4, to obtain an unvulcanized rubber composition. The obtained unvulcanized rubber composition is then vulcanized (vulcanization process) and the rubber composition for tire according to the fourth invention can be produced. It is noted that the timing when other compounding agents such as carbon black (C-4), a plasticizer (F-4), an anti-aging agent (G-4), a zinc oxide, a stearic acid and the like are added and kneaded is not limited particularly, and these compounding agents may be added in any of the step X1-4, the step X2-4 or the step F-4, or may be added divisionally.

Particularly, the production method of the fourth invention is characterized in that the silica 1 and the silica 2 are respectively added divisionally in the step X1-4 and the step X2-4. By kneading the silica 1 which is particulate and inferior in dispersibility in the step X1-4, the whole dispersibility of silica is improved. The production method is also characterized in that the coupling agent (D1-4) is kneaded in the preceding step (step X1-4) before the coupling agent (D2-4) having a sulfide group is kneaded. The coupling agent (D1-4) can form homogeneous chemical bonds between the filler and the polymer without losing activity even in the kneading in the prior input as in the fourth invention because the coupling agent does not have a plurality of alkoxysilyl groups in the molecule and the coagulation thereof is small and also because a mercapto group suitably reacting with a polymer part becomes a fatty acid thioester, thereby non-uniformity resulting from a rapid reaction is prevented.

Step X1-4

In the step X1-4, compounding agents comprising all amount of the rubber component (A-4), the silica 1 (B1-4), the coupling agent (D1-4) and optionally a part of the vulcanizing agent (E-4) are kneaded with a Banbury mixer and the like. In this step, the filler disperses while forming a strong bond with a rubber component, particularly with a rubber component having high affinity with the filler. Further, by use of a coupling agent (D1-4) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane (coupling agent (D2-4)) is input in the step X1, then it releases sulfur even in this phase, thereby processability is deteriorated, dispersion of the filler is prevented and the activity of a coupling agent itself is lowered. The coupling agent (D1-4) represented by the chemical formula (1) does not release sulfur, thereby being able to continue kneading while maintaining processability according to the production method of the fourth invention.

The added amount of the coupling agent (D1-4) represented by the chemical formula (1) in the step X1-4 is preferably not less than 4 parts by mass, more preferably not less than 5 parts by mass, further preferably not less than 6 parts by mass based on 100 parts by mass of the added amount of the silica (B-4) in the step X1-4, since a reaction with the filler becomes sufficient and the excellent effect of improving processability of the coupling agent (D1-4) can be exerted. On the other hand, the added amount of the coupling agent (D1-4) represented by the chemical formula (1) in the step X1-4 is preferably not more than 20 parts by mass, more preferably not more than 10 parts by mass, further preferably not more than 9 parts by mass from the viewpoint of the effect of improving dispersibility of silica that is compatible with the increase of the cost.

It is preferable that the carbon black (C-4) is added in the step X1-4 and/or the step X2-4. The added amount of the carbon black (C-4) in the step X1-4 is preferably not less than 10% by mass, more preferably not less than 50% by mass, further preferably not less than 80% by mass, most preferably 100% by mass of the total added amount of the carbon black (C-4) from the viewpoint of the improvement of dispersibility of carbon black and efficiency of the step. If the added amount of the carbon black (C-4) in the step X1-4 is less than 100% by mass, it is preferable that the remaining amount is added in the step X2-4.

While the step in which the plasticizer (F-4) is added is not limited particularly, it is preferable that not less than 50% by mass, more preferably not less than 70% by mass, further preferably not less than 80% by mass of the total added amount of the plasticizer (F-4) is added in the step X1-4. If the added amount of the plasticizer (F-4) in the step X1-4 is less than 100% by mass, it is preferable that the remaining amount is added in the step X2-4 since dispersibility of the silica which is added in the step X2-4 is more improved.

It is preferable that the surfactant is added in the step X1-4 and/or the step X2-4 from the viewpoint of promoting the effect of dispersing silica, and is preferably added in the step X1-4 since the effect of dispersing silica is more promoted and a gelation of the coupling agent can be prevented.

The temperature at discharge of kneading in the step X1-4 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-4 is within the above range, the kneaded product in which silica (B-4) is well dispersed tends to be obtained efficiently.

The highest temperature during kneading in the step X1-4 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, polysulfide silane is not added as a vulcanization accelerator in the step X1-4 according to the fourth invention and thus a defect does not arise even if the kneading temperature becomes high and it is possible to promote the reaction of the coupling agent and promote the dispersion of the silica.

The kneading time in the step X1-4 is not limited particularly, but the kneading time in each step is preferably not less than 3.0 minutes, more preferably not less than 4.0 minutes, further preferably not less than 4.5 minutes since the kneaded product in which silica is well dispersed can be obtained efficiently. On the other hand, the respective kneading time in each step is preferably not more than 9 minutes, more preferably not more than 8 minutes, further preferably not more than 7 minutes.

In one embodiment of the fourth invention, it is preferable to keep the kneaded product at 150 to 190° C. for 10 to 120 seconds after the temperature reaches the highest temperature in the step X1-4 and the kneading is finished since the reaction between the coupling agent (D1-4) and the silica is completely performed.

Step X2-4

In the step X2-4, the compounding agents comprising the silica 2 (B2-4), the coupling agent (D2-4) and optionally a part of the vulcanizing agent (E-4) are added to the kneaded product of the step X1-4 and the mixture is kneaded. If the all amount of the silica is input in the step X1-4, the silica tends to be localized in a polymer portion having high affinity with silica such as a modified polymer and/or an interface portion of the polymer, however, in the production method of the fourth invention, since the silica 1 and the silica 2 are respectively added divisionally in the step X1-4 and the step X2-4, the silica becomes easily dispersed through the entire rubber component. Further, the later added silica 2 (added in the step X2-4) itself has an effect of promoting kneading by applying shear to the rubber component. Moreover, in the production method of the fourth invention, since the coupling agent (D1-4) represented by the chemical formula (1) is kneaded in the step X1-4, an initial reduction of the activity of the coupling agent is prevented and processability throughout the kneading operation can be maintained.

In addition, by kneading the coupling agent (D2-4) having a sulfide group in the step X2-4, an initial reduction of the activity of the coupling agent is prevented and processability throughout the kneading operation can be maintained. Moreover, since the coupling agent (D2-4) can release sulfur that acts as a vulcanizer, a uniform crosslinking is promoted and the improvement of physical properties of the rubber can be attempted.

The added amount of the coupling agent (D2-4) in the step X2-4 is preferably not less than 4 parts by mass, more preferably not less than 5 parts by mass, further preferably not less than 6 parts by mass based on 100 parts by mass of the added amount of the silica (B-4) in the step X2-4 since the reaction with a filler can be made sufficient and the effect of improving excellent processability of the coupling agent (D2-4) can be brought out. On the other hand, the added amount of the coupling agent (D2-4) represented by the chemical formula (1) in the step X2-4 is preferably not more than 20 parts by mass, more preferably not more than 10 parts by mass, further preferably not more than 9 parts by mass from the viewpoint of the effect of improving dispersibility of silica that is compatible with the increase of the cost.

The step in which the anti-aging agent (G-4) is added is not limited particularly, but from the viewpoint of operation efficiency and prevention of activity reduction of the anti-aging agent, it is preferable that all amount is added in the step X2-4.

The temperature at discharge of kneading in the step X2-4 is not limited particularly, but is preferably not lower than 100° C., more preferably not lower than 120° C., further preferably not lower than 130° C. On the other hand, the temperature at discharge is preferably not higher than 200° C., more preferably not higher than 170° C., further preferably not higher than 160° C. If the temperature at discharge in the step X2-4 is within the above range, the kneaded product in which silica (B-4) is well dispersed tends to be obtained efficiently.

The highest temperature during kneading in the step X2-4 is not limited particularly, but is preferably not lower than 100° C., more preferably not lower than 120° C., further preferably not lower than 130° C. since the coupling agent (D2-4) is sufficiently reacted and the kneaded product in which the silica is well dispersed can be obtained efficiently. On the other hand, the highest temperature during kneading is preferably not higher than 200° C., more preferably not higher than 170° C., further preferably not higher than 160° C. for preventing a rubber burning.

The kneading time in the step X2-4 is not limited particularly, but the kneading time is preferably not less than 3.0 minutes since the kneaded product in which silica is well dispersed can be obtained efficiently. On the other hand, the respective kneading time is preferably not more than 9 minutes, more preferably not more than 8 minutes, further preferably not more than 7 minutes.

Step F-4

In the step F-4, the kneaded product obtained in the step X2-4 is cooled and then the vulcanizing agent (E-4) containing a vulcanizer and a vulcanization accelerator is added and the mixture is kneaded with an open roll and the like to obtain an unvulcanized rubber composition.

While the vulcanizing agent may be added in the step F-4 at a time, it is preferable that a part or all amount is added in the step X1-4 and/or the step X2-4 and then the remaining amount is added in the step F-4. By adding a part or all amount in the step X1-4 and/or the step X2-4, dispersion between the silica and the rubber component can be promoted. It is more preferable that a part or all amount of the guanidine vulcanization accelerator is added in the step X1-4 and/or the step X2-4 since dispersibility of the silica can be more promoted.

It is preferable that the kneaded product obtained in the step X2-4 is normally cooled to 100° C. or less, preferably to 20 to 80° C.

The temperature at discharge of kneading in the step F-4 is preferably not higher than 110° C., more preferably not higher than 100° C. If the temperature at discharge exceeds 110° C., a rubber burning (scorch) tends to easily arise. On the other hand, the lower limit of the temperature at discharge of kneading in the step F is not limited particularly, but is preferably not lower than 80° C.

The kneading time in the step F-4 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-4 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the fourth invention can be obtained successfully.

Rubber Composition for Tire

The rubber composition for tire according to the fourth invention can be used for any component of a tire and among these, can be suitably used for a tread or a sidewall since it is the rubber composition for tire in which processability, fuel efficiency and abrasion resistance are improved in a good balance.

Tire

In addition, a tire of the fourth invention can be produced with a normal method by use of the rubber composition for tire according to the fourth invention. That is, the rubber composition for tire produced by the production method of the fourth invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the fourth invention can be produced. It is noted that the tire of the fourth invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars.

<Fifth Invention>

The fifth invention is a production method of a rubber composition for tire comprising a rubber component comprising a butadiene rubber (A1-5) and an isoprene-based rubber (A2-5), silica (B-5), carbon black (C-5), a coupling agent (D1-5) represented by the following chemical formula (1), a coupling agent (D2-5) having a sulfide group and a vulcanizing agent (E-5) comprising a vulcanizer and a vulcanization accelerator, the method comprising:

(step X1-5) a step X1-5 of kneading A1-5, a part of B-5, D1-5 and optionally a part of E-5, (step X2-5) a step X2-5 of kneading the kneaded product of the step X1-5, A2-5, the remaining amount of B-5, D2-5 and optionally a part of E-5, and (step F-5) a step F of kneading the kneaded product of the step X2-5 and the remaining amount of E-5.

Chemical formula (1):

In the chemical formula (1), p represents an integer of 1 to 3, q represents an integer of 1 to 5, and k represents an integer of 5 to 12.

It is preferable that the butadiene rubber (A1-5) comprises a butadiene rubber which has a functional group that reacts with silica.

It is preferable that the nitrogen adsorption specific surface area of the silica is not less than 160 m²/g and the total added amount of the silica is not less than 40 parts by mass based on 100 parts by mass of the rubber component.

It is preferable that the added amount of the coupling agent in each of the step X1-5 and the step X2-5 is 4 to 10 parts by mass based on 100 parts by mass of the silica added in each step.

It is preferable that the added amount of the silica in the step X1-5 is 10 to 90% by mass of the total added amount of silica.

It is preferable that the production method is a production method of the rubber composition further comprising a plasticizer and not less than 50% by mass of the total added amount of a plasticizer is kneaded in the step X1-5.

It is preferable that the highest temperature in the step X1-5 is 140 to 200° C.

It is preferable that after the kneading in the step X1-5 is finished, the production method comprises a step of keeping the kneaded product at 150 to 190° C. for 10 to 120 seconds.

It is preferable that a part or all amount of the vulcanization accelerator is kneaded in the step X1-5 and/or the step X2-5.

It is preferable that the production method is a production method of the rubber composition further comprising an anti-aging agent and an anti-aging agent is kneaded in the step X2-5.

It is preferable that the production method is a production method of the rubber composition further comprising a surfactant and the surfactant is kneaded in the step X1-5 and/or the step X2-5.

The fifth invention also relates to a tire having a tire component composed of the rubber composition for tire produced by the above production method of the rubber composition for tire.

According to the fifth invention, it is possible to produce a rubber composition for tire in which fuel efficiency, abrasion resistance and wet grip performance are improved in a good balance. Further, by use of a tire having a tire component composed of the produced rubber composition for tire, it is possible to produce a tire in which fuel efficiency, abrasion resistance and wet grip performance are improved in a good balance.

The rubber composition according to the fifth invention is characterized by comprising a rubber component comprising a butadiene rubber (A1-5) and an isoprene-based rubber (A2-5), silica (B-5), carbon black (C-5), coupling agents (D1-5) and (D2-5), and a vulcanizing agent (E-5) comprising a vulcanizer and a vulcanization accelerator.

Rubber Component

The rubber component is characterized by comprising a butadiene rubber (A1-5) and an isoprene-based rubber (A2-5). By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, tin tetrachloride and silicon tetrachloride. It is noted that a type or compounded amount of a rubber component can be appropriately selected depending on a part to which the rubber component is applied.

The above rubber component comprises a butadiene rubber (BR) since it is excellent in abrasion resistance. In general, a rubber composition in which a white filler such as silica (B-5) is compounded in BR has a problem that dispersibility of the filler is low and it is difficult to obtain desired performance. However, in the fifth invention, the reaction between a filler and a rubber component is improved by divisionally kneading a specified coupling agent (D-5). Accordingly, dispersibility of a filler increases and fuel efficiency and abrasion resistance are improved as well as satisfactory processability can be obtained, thereby synergistically improving a balance among these performances.

Examples of the BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of the achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

The content of BR in the rubber component is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75%, further preferably not more than 70% by mass from the viewpoint of processability.

Examples of the isoprene-based rubber include a chemically synthesized polyisoprene rubber (IR), a natural rubber (NR), an epoxidized natural rubber (ENR) and the like. Among these, NR and ENR are preferable from the viewpoint of easy availability and the rubber strength.

In particular, the isoprene-based rubber or modified BR, due to a strong interaction of its functional groups, coagulates itself and dispersion of a filler usually becomes all the more difficult. However, in the fifth invention, by divisionally kneading a specified coupling agent, the coagulation of the rubber component is prevented and the reaction with silica is promoted.

The rubber component may comprise, in addition to the above BR and the isoprene-based rubber, a styrene butadiene rubber (SBR), a styrene-isoprene-butadiene rubber (SIBR) and the like as necessary. If the rubber composition comprises a rubber component other than BR and the isoprene-based rubber, the rubber component is preferably added in the step X2-5 as described below.

Silica (B-5)

The silica (B-5) is not limited particularly and ones generally used in the tire industry can be used. Examples thereof include dry processed silica (silicic anhydride) and wet processed silica (hydrous silicic acid) and the like, and wet processed silica is preferable because it has more silanol groups.

The nitrogen adsorption specific surface area ($N_2SA$) of the silica (B-5) is preferably not less than 40 $m^2/g$, more preferably not less than 50 $m^2/g$, further preferably not less than 100 $m^2/g$, particularly preferably not less than 130 $m^2/g$, most preferably not less than 160 $m^2/g$ from the viewpoint of the breaking strength. On the other hand, the $N_2SA$ of the silica (B-5) is preferably not more than 500 $m^2/g$, more preferably not more than 300 $m^2/g$, further preferably not more than 250 $m^2/g$, particularly preferably not more than 200 $m^2/g$ from the viewpoint of fuel efficiency and processability. It is noted that the $N_2SA$ of the silica (B-5) herein is a value as measured with the BET method in accordance with ATSM D3037-81.

The content (total added amount) of the silica (B-5) is preferably not less than 10 parts by mass, more preferably not less than 20 parts by mass, further preferably not less than 30 parts by mass, particularly preferably not less than 40 parts by mass based on 100 parts by mass of the rubber component (A-5) from the viewpoint of fuel efficiency and wet grip performance. On the other hand, the total content of the silica (B-5) is preferably not more than 200 parts by mass, more preferably not more than 150 parts by mass, further preferably not more than 120 parts by mass from the viewpoint of dispersibility of a filler into the rubber component and processability.

Carbon Black (C-5)

The carbon black (C-5) is not limited particularly and ones generally used in the tire industry such as GPF, FEF, HAF, ISAF, SAF and the like can be used, and these carbon black may be used alone, or may be used in combination with two or more thereof.

The nitrogen adsorption specific surface area ($N_2SA$) of the carbon black (C-5) is preferably not less than 80 $m^2/g$, more preferably not less than 100 $m^2/g$ from the viewpoint of weather resistance and antistatic performance. On the other hand, the $N_2SA$ of the carbon black (C-5) is preferably not more than 200 $m^2/g$, more preferably not more than 150 $m^2/g$ from the viewpoint of processability. It is noted that the $N_2SA$ of the carbon black (C) herein is a value as measured in accordance with JIS K6217, method A.

The content (total added amount) of the carbon black (C-5) is preferably not less than 1 part by mass, more preferably not less than 3 parts by mass based on 100 parts by mass of the rubber component (A-5). If the content of the carbon black (C-5) is less than 1 part by mass, the effect obtained by inclusion of the carbon black may not be obtained sufficiently. On the other hand, the content of the carbon black (C-5) is preferably not more than 30 parts by mass, more preferably not more than 10 parts by mass from the viewpoint of fuel efficiency and processability.

Coupling Agent

The coupling agent (D1-5) is a compound represented by the following chemical formula (1).

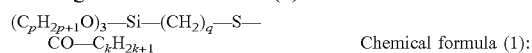

Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D1-5) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and the cost.

The coupling agent (D2-5) is a coupling agent having a sulfide group and examples thereof include bis(3-triethoxysilylpropyl)tetrasulfide, bis(2-triethoxysilylethyl)tetrasulfide, bis(3-trimethoxysilylpropyl)tetrasulfide, bis(2-trimethoxysilylethyl)tetrasulfide, bis(3-triethoxysilylpropyl) trisulfide, bis(3-trimethoxysilylpropyl)trisulfide, bis(3-triethoxysilylpropyl)disulfide, bis(3-trimethoxysilylpropyl) disulfide, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 2-trimethoxysilylethyl-N,N-dimethylthiocarbamoyl tetrasulfide, 3-trimethoxysilylpropylbenzothiazolyl tetrasulfide, 3-triethoxysilylpropylbenzothiazole tetrasulfide, 3-triethoxysilylpropyl methacrylate monosulfide, 3-trimethoxysilylpropyl methacrylate monosulfide and the like. Suitable examples of these coupling agents include Si75 (bis(3-triethoxysilylpropyl)disulfide), Si69 (bis(3-triethoxysilylpropyl)tetrasulfide) manufactured by Evonik Industries, which are available as a mixture that generally has a certain distribution, and the like.

The total content of the coupling agents (D1-5) and (D2-5) is preferably not less than 4 parts by mass, more preferably not less than 5 parts by mass, further preferably not less than 6 parts by mass based on 100 parts by mass of the total content of the silica from the viewpoint of the effect of improving a reaction with a filler and processability. On the other hand, the total content of the coupling agents is preferably not more than 20 parts by mass, more preferably not more than 10 parts by mass, further preferably not more than 9 parts by mass from the viewpoint of the effect of improving dispersibility of silica that is compatible with the increase of the cost.

Vulcanizing Agent (E-5)

The vulcanizing agent (E-5) comprises a vulcanizer (E1-5) and a vulcanization accelerator (E2-5). Vulcanizing agents generally used in the rubber industry such as a vulcanization accelerator auxiliary agent can be also used.

Vulcanizer (E1-5)

The vulcanizer (E1-5) is not limited particularly and ones generally used in the tire industry can be used. Since the effect of the fifth invention can be successfully obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of the vulcanizer (E1-5) is preferably not less than 0.1 part by mass, more preferably not less than 0.5 part by mass based on 100 parts by mass of the rubber component (A-5). On the other hand, the content of the vulcanizer (E1-5) is preferably not more than 15 parts by mass, more preferably not more than 5 parts by mass. If the content of the vulcanizer (E1-5) is within the above range, satisfactory tensile strength, abrasion resistance and heat resistance can be obtained.

Vulcanization Accelerator (E2-5)

The vulcanization accelerator (E2-5) is not limited particularly and ones generally used in the tire industry can be used. Examples thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolsulfenamide, N-t-butyl-2-benzothiazolsulfenamide, N-oxyethylene-2-benzothiazolsulfenamide, and N,N'-diisopropyl-2-benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-5) is preferably not less than 0.1 part by mass, more preferably not less than 0.2 part by mass based on 100 parts by mass of the rubber component (A-5). On the other hand, the content of the vulcanization accelerator (E2-5) is preferably not more than 5 parts by mass, more preferably not more than 3 parts by mass. If the content of the vulcanization accelerator (E2-5) is within the above range, the reduction of the elastic modulus of rubber and the deterioration of breaking resistance can be prevented.

Other Compounding Agents

The rubber composition for tire of the fifth invention can suitably comprise, in addition to the above components, compounding agents that have been used in the rubber industry such as, for example, a plasticizer (F-5), a filler for reinforcement other than silica and carbon black, an anti-aging agent (G-5), an antioxidant, a stearic acid, wax and the like as necessary.

Plasticizer (F-5)

Since processability is improved and the strength of rubber is increased, it is preferable that the rubber composition for tire of the fifth invention comprises the plasticizer (F-5). The plasticizer (F-5) is not limited particularly and ones generally used in the tire industry can be used, and examples thereof include oil, liquid polymer, liquid resin and the like. Among these, oil is preferable since the cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), heavy naphthene oil and the like.

In the case where the rubber composition comprise oil as the plasticizer (F-5), the content thereof based on 100 parts by mass of the rubber component (A-5) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-5)

The anti-aging agent (G-5) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises the anti-aging agent (G-5), the content thereof based on 100 parts by mass of the rubber component (A-5) is preferably not less than 0.5 part by mass, more preferably not less than 1.0 part by mass from the viewpoint of ozone resistance and crack resistance. On the other hand, the content of the anti-aging agent is preferably not more than 10 parts by mass, more preferably not more than 5 parts by mass from the viewpoint of prevention of discoloration.

Surfactant

In an embodiment of the fifth invention, it is preferable that the rubber composition further comprises a surfactant. By inclusion of a surfactant, dispersibility of the above fillers comprising silica and carbon black is improved and a discoloration of the obtained rubber composition for tire due to deterioration over time can be prevented.

Examples of the surfactant include metallic soap such as a metallic salt of an organic acid, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of the surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-5) from the viewpoint of the effect of improving dispersibility of silica. On the other hand, the content of the surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

Production Method of Rubber Composition for Tire

The production method of a rubber composition for tire of the fifth invention is characterized by dividing a kneading step into a step X1-5, a step X2-5 and a step F-5. Known kneaders can be used in each step and examples thereof include a Banbury mixer, a kneader, an open roll and the like.

Specifically, the production method of a rubber composition for tire includes a kneading process comprising a step X1-5 of kneading A1-5, a part of B-5, D1-5 and optionally a part of E-5, a step X2-5 of kneading the kneaded product of the step X1-5, A2-5, the remaining amount of B-5, D2-5 and optionally a part of E-5, and a step F-5 of kneading the kneaded product of the step X2-5 and the remaining amount of E-5, to obtain an unvulcanized rubber composition. The obtained unvulcanized rubber composition is then vulcanized (vulcanization process) and the rubber composition for tire according to the fifth invention can be produced. It is noted that the timing when other compounding agents such as carbon black (C-5), a plasticizer (F-5), an anti-aging agent (G-5), a zinc oxide, a stearic acid and the like are added and kneaded is not limited particularly, and these compounding agents may be added in any of the step X1-5, the step X2-5 or the step F-5, or may be added divisionally.

Particularly, the production method of the fifth invention is characterized in that the coupling agent (D1-5) is kneaded in the preceding step (step X1-5) before the coupling agent (D2-5) having a sulfide group is kneaded. The coupling agent (D1-5) can form homogeneous chemical bonds between the filler and the polymer without losing activity even in the kneading in the prior input as in the fifth invention because the coupling agent does not have a plurality of alkoxylsilyl groups in the molecule and the coagulation thereof is small and also because a mercapto group suitably reacting with a polymer part becomes a fatty acid thioester, thereby non-uniformity resulting from a rapid reaction is prevented.

Step X1-5

In the step X1-5, compounding agents comprising the butadiene rubber (A1-5), a part of the silica (B-5), the coupling agent (D1-5) and optionally a part of the vulcanizing agent (E-5) are kneaded with a Banbury mixer and the like. In this step, the filler disperses while forming a strong bond with a rubber component, particularly with a rubber component having high affinity with the filler. Further, by use of a coupling agent (D1-5) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane (coupling agent (D2-5)) is input in the step X1, then it releases sulfur even in this phase, thereby processability is deteriorated, dispersion of the filler is prevented and the activity of a coupling agent itself is lowered. The coupling agent (D1-5) represented by the chemical formula (1) does not release sulfur, thereby being able to continue kneading while maintaining processability according to the production method of the fifth invention.

In the rubber composition comprising BR and an isoprene-based rubber as a rubber component, the silica tends to be localized in the isoprene-based rubber and/or an interface. However, in the production method of the fifth invention, by previously kneading the BR, silica and a specified coupling agent in the step X1-5, the silica is allowed to also exist in the BR well.

The added amount of the silica (B-5) in the step X1-5 is preferably not less than 10% by mass, more preferably not less than 30% by mass, further preferably not less than 40% by mass, further preferably not less than 50% by mass of the total added amount of the silica (B-5) from the viewpoint of improvement of the effect of kneading silica, sufficient dispersion of silica and abrasion resistance. On the other hand, the added amount of the silica (B-5) in the step X1-5 is preferably not more than 95% by mass, more preferably not more than 90% by mass, further preferably not more than 85% by mass of the total added amount of the silica (B-5) from the viewpoint of the effect of adding the silica divisionally in the step X2-5 as described below, fuel efficiency and abrasion resistance.

The added amount of the coupling agent (D1-5) represented by the chemical formula (1) in the step X1-5 is preferably not less than 4 parts by mass, more preferably not less than 5 parts by mass, further preferably not less than 6 parts by mass based on 100 parts by mass of the added amount of the silica (B-5) in the step X1-5, since a reaction with the filler becomes sufficient and the excellent effect of improving processability of the coupling agent (D1-5) can be brought out. On the other hand, the added amount of the coupling agent (D1-5) represented by the chemical formula (1) in the step X1-5 is preferably not more than 20 parts by mass, more preferably not more than 10 parts by mass, further preferably not more than 9 parts by mass from the viewpoint of the effect of improving dispersibility of silica that is compatible with the increase of the cost.

It is preferable that the carbon black (C-5) is added in the step X1-5 and/or the step X2-5. The added amount of the carbon black (C-5) in the step X1-5 is preferably not less than 10% by mass, more preferably not less than 50% by mass, further preferably not less than 80% by mass, most preferably 100% by mass of the total added amount of the carbon black (C-5) from the viewpoint of the improvement of dispersibility of carbon black and efficiency of the step. If the added amount of the carbon black (C-5) in the step X1-5 is less than 100% by mass, it is preferable that the remaining amount is added in the step X2-5.

While the step in which the plasticizer (F-5) is added is not limited particularly, it is preferable that not less than 50% by mass, more preferably not less than 70% by mass, further preferably not less than 80% by mass of the total added amount of the plasticizer (F-5) is added in the step X1-5. If the added amount of the plasticizer (F-5) in the step X1-5 is less than 100% by mass, it is preferable that the remaining amount is added in the step X2-5 since dispersibility of the silica which is added in the step X2-5 is more improved.

It is preferable that the surfactant is added in the step X1-5 and/or the step X2-5 from the viewpoint of promoting the effect of dispersing silica, and is preferably added in the step X1-5 since the effect of dispersing silica is more promoted and a gelation of the coupling agent can be prevented.

The temperature at discharge of kneading in the step X1-5 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-5 is within the above range, the kneaded product in which silica (B-5) is well dispersed tends to be obtained efficiently.

The highest temperature during kneading in the step X1-5 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, polysulfide silane is not added as a vulcanization accelerator in the step X1-5 according to the fifth invention and thus a defect does not arise even if the kneading temperature becomes high and it is possible to promote the reaction of the coupling agent and promote the dispersion of the silica.

The kneading time in the step X1-5 is not limited particularly, but the kneading time in each step is preferably not less than 3.0 minutes, more preferably not less than 4.0 minutes, further preferably not less than 4.5 minutes since the kneaded product in which silica is well dispersed can be obtained efficiently. On the other hand, the respective kneading time in each step is preferably not more than 9 minutes, more preferably not more than 8 minutes, further preferably not more than 7 minutes.

In one embodiment of the fifth invention, it is preferable to keep the kneaded product at 150 to 190° C. for 10 to 120 seconds after the temperature reaches the highest temperature in the step X1-5 and the kneading is finished since the reaction between the coupling agent (D1-5) and the silica is completely performed.

Step X2-5

In the step X2-5, the compounding agents comprising the isoprene-based rubber (A2-5), the remaining amount of the silica (B-5), the coupling agent (D2-5) and optionally a part of the vulcanizing agent (E-5) are added to the kneaded product of the step X1-5 and the mixture is kneaded. If the all amount of the silica is added in the step X1-5, the silica tends to be localized in a polymer portion having high affinity with silica such as an isoprene rubber and/or an interface portion of the polymer, however, in the production method of the fifth invention, since the silica is respectively input divisionally in the step X1-5 and the step X2-5, the silica becomes easily dispersed through the entire rubber component. Further, the later added silica (added in the step X2-5) itself has an effect of promoting kneading by applying shear to the rubber component. Moreover, in the production method of the fifth invention, since the coupling agent (D1-5) represented by the chemical formula (1) is kneaded in the step X1-5, an initial reduction of the activity of the coupling agent is prevented and processability throughout the kneading operation can be maintained.

In addition, by kneading the coupling agent (D2-5) having a sulfide group in the step X2-5, an initial reduction of the activity of the coupling agent is prevented and processability throughout the kneading operation can be maintained. Moreover, since the coupling agent (D2-5) can release sulfur that acts as a vulcanizer, a uniform crosslinking is promoted and the improvement of physical properties of the rubber can be attempted.

The added amount of the coupling agent (D2-5) in the step X2-5 is preferably not less than 4 parts by mass, more preferably not less than 5 parts by mass, further preferably not less than 6 parts by mass based on 100 parts by mass of the added amount of the silica (B-5) in the step X2-5 since the reaction with a filler can be made sufficient and the effect of improving excellent processability of the coupling agent (D2-5) can be brought out. On the other hand, the added amount of the coupling agent (D2-5) represented by the chemical formula (1) in the step X2-5 is preferably not more than 20 parts by mass, more preferably not more than 10 parts by mass, further preferably not more than 9 parts by mass from the viewpoint of the effect of improving dispersibility of silica that is compatible with the increase of the cost.

The step in which the anti-aging agent (G-5) is added is not limited particularly, but from the viewpoint of operation efficiency and prevention of activity reduction of the anti-aging agent, it is preferable that all amount is added in the step X2-5.

The temperature at discharge of kneading in the step X2-5 is not limited particularly, but is preferably not lower than 100° C., more preferably not lower than 120° C., further preferably not lower than 130° C. On the other hand, the temperature at discharge is preferably not higher than 200° C., more preferably not higher than 170° C., further preferably not higher than 160° C. If the temperature at discharge in the step X2-5 is within the above range, the kneaded product in which silica (B-5) is well dispersed tends to be obtained efficiently.

The highest temperature during kneading in the step X2-5 is not limited particularly, but is preferably not lower than 100° C., more preferably not lower than 120° C., further preferably not lower than 130° C. since the coupling agent (D2-5) is sufficiently reacted and the kneaded product in which the silica is well dispersed can be obtained efficiently. On the other hand, the highest temperature during kneading is preferably not higher than 200° C., more preferably not higher than 170° C., further preferably not higher than 160° C. for preventing a rubber burning.

The kneading time in the step X2-5 is not limited particularly, but the kneading time is preferably not less than 3.0 minutes since the kneaded product in which silica is well dispersed can be obtained efficiently. On the other hand, the respective kneading time is preferably not more than 9 minutes, more preferably not more than 8 minutes, further preferably not more than 7 minutes.

Step F

In the step F-5, the kneaded product obtained in the step X2-5 is cooled and then the vulcanizing agent (E-5) containing a vulcanizer and a vulcanization accelerator is added and the mixture is kneaded with an open roll and the like to obtain an unvulcanized rubber composition.

While the vulcanizing agent may be added in the step F-5 at a time, it is preferable that a part or all amount is added in the step X1-5 and/or the step X2-5 and then the remaining amount is added in the step F. By adding a part or all amount in the step X1-5 and/or the step X2-5, dispersion between the silica and the rubber component can be promoted. It is more preferable that a part or all amount of the guanidine vulcanization accelerator is added in the step X1-5 and/or the step X2-5 since dispersibility of the silica can be more promoted.

It is preferable that the kneaded product obtained in the step X2-5 is normally cooled to 100° C. or less, preferably to 20 to 80° C.

The temperature at discharge of kneading in the step F-5 is preferably not higher than 110° C., more preferably not higher than 100° C. If the temperature at discharge exceeds 110° C., a rubber burning (scorch) tends to easily arise. On the other hand, the lower limit of the temperature at discharge of kneading in the step F is not limited particularly, but is preferably not lower than 80° C.

The kneading time in the step F-5 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-5 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the fifth invention can be obtained successfully.

Rubber Composition for Tire

The rubber composition for tire according to the fifth invention can be used for any component of a tire and among these, can be suitably used for a tread or a sidewall since it is the rubber composition for tire in which processability, fuel efficiency and abrasion resistance are improved in a good balance.

Tire

In addition, a tire of the fifth invention can be produced with a normal method by use of the rubber composition for tire according to the fifth invention. That is, the rubber composition for tire produced by the production method of the fifth invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the fifth invention can be produced. It is noted that the tire of the fifth invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars.

<Sixth Invention>

The sixth invention is a production method of a rubber composition for tire comprising a rubber component comprising a butadiene rubber (A1-6) and a styrene butadiene rubber (A2-6), silica (B-6), carbon black (C-6), a coupling agent (D-6) represented by the following chemical formula (1) and a vulcanizing agent (E-6) comprising a vulcanizer and a vulcanization accelerator, the method comprising:
(step X1-6) a step X1-6 of kneading A1-6, a part of B-6, a part of D-6 and optionally a part of E-6, (step X2-6) a step X2-6 of kneading the kneaded product of the step X1-6, A2-6, the remaining amount of B-6, the remaining amount of D-6 and optionally a part of E-6, and (step F-6) a step F-6 of kneading the kneaded product of the step X2-6 and the remaining amount of E-6.

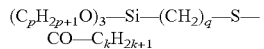

Chemical formula (1):

In the chemical formula (1), p represents an integer of 1 to 3, q represents an integer of 1 to 5, and k represents an integer of 5 to 12.

It is preferable that the butadiene rubber (A1-6) comprises a butadiene rubber which has a functional group that reacts with silica and/or a styrene butadiene rubber (A2-6) comprises a styrene butadiene rubber which has a functional group that reacts with silica.

It is preferable that the nitrogen adsorption specific surface area of the silica is not less than 160 m$^2$/g and the total added amount of the silica is not less than 40 parts by mass based on 100 parts by mass of the rubber component.

It is preferable that the added amount of the coupling agent in each of the step X1-6 and the step X2-6 is 4 to 10 parts by mass based on 100 parts by mass of the silica added in each step.

It is preferable that the added amount of the silica in the step X1-6 is 10 to 90% by mass of the total added amount of silica.

It is preferable that the production method is a production method of the rubber composition further comprising a plasticizer and not less than 50% by mass of the total added amount of a plasticizer is kneaded in the step X1-6.

It is preferable that the highest temperature in the step X1-6 and/or the step X2-6 is 140 to 200° C.

It is preferable that after the kneading in the step X1-6 and/or the step X2-6 is finished, the production method comprises a step of keeping the kneaded product at 150 to 190° C. for 10 to 120 seconds.

It is preferable that a part or all amount of the vulcanization accelerator is kneaded in the step X1-6 and/or the step X2-6.

It is preferable that the production method is a production method of the rubber composition further comprising an anti-aging agent and an anti-aging agent is kneaded in the step X2-6.

It is preferable that the production method is a production method of the rubber composition further comprising a surfactant and the surfactant is kneaded in the step X1-6 and/or the step X2-6.

The sixth invention also relates to a tire having a tire component composed of the rubber composition for tire produced by the above production method of the rubber composition for tire.

According to the sixth invention, it is possible to produce a rubber composition for tire in which fuel efficiency, abrasion resistance and wet grip performance are improved in a good balance. Further, by use of a tire having a tire component composed of the produced rubber composition for tire, it is possible to produce a tire in which fuel efficiency, abrasion resistance and wet grip performance are improved in a good balance.

The rubber composition according to the sixth invention is characterized by comprising a rubber component comprising a butadiene rubber (A1-6) and a styrene butadiene rubber (A2-6), silica (B-6), carbon black (C-6), a specified coupling agent (D-6) and a vulcanizing agent (E-6) comprising a vulcanizer and a vulcanization accelerator.

Rubber Component

The rubber component is characterized by comprising a butadiene rubber (A1-6) and a styrene butadiene rubber (A2-6). By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The above rubber component comprises a butadiene rubber (BR) since it is excellent in abrasion resistance. In general, a rubber composition in which a white filler such as silica (B-6) is compounded in BR has a problem that dispersibility of the filler is low and it is difficult to obtain desired performance. However, in the sixth invention, the reaction between a filler and a rubber component is improved by divisionally kneading a specified coupling agent (D-6). Accordingly, dispersibility of a filler increases and fuel efficiency and abrasion resistance are improved as well as satisfactory processability can be obtained, thereby synergistically improving a balance among these performances.

Examples of the BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of the achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

The content of BR in the rubber component is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75%, further preferably not more than 70% by mass from the viewpoint of processability.

The styrene butadiene rubber (SBR) is not limited particularly and examples thereof include an unmodified solution-polymerized styrene-butadiene rubber (S-SBR), an unmodified emulsion-polymerized styrene-butadiene rubber (E-SBR), and modified SBRs of these (modified E-SBR, modified S-SBR) and the like. Examples of the modified SBR include a modified SBR in which a terminal and/or a main chain is modified, a modified SBR coupled by a tin or silicon compound (such as a condensate or one having a branched structure) and the like. Among these SBRs, S-SBR and modified S-SBR are preferable since they can improve grip performance and abrasion resistance in a good balance, and from the viewpoint of the reaction with silica, a modified SBR having at least one selected from the group consisting of a silyl group, an amino group, an amide group, a hydroxyl group and an epoxy group is particularly preferable. While these SBRs can be used alone, a combined use of SBRs having different physical properties such as a content of styrene is also possible depending on its application. It is noted that SBRs may be appropriately selected depending on a part to which they are applied.

The styrene content of SBR is preferably not less than 5% by mass, more preferably not less than 10% by mass, further preferably not less than 20% by mass from the viewpoint of dry grip performance, wet grip performance and rubber strength. On the other hand, the styrene content of SBR is preferably not more than 60% by mass, more preferably not more than 50% by mass, further preferably not more than 40% by mass from the viewpoint of fuel efficiency. It is noted that the styrene content of SBR herein is calculated from a $^1$H-NMR measurement.

The vinyl bond amount of SBR is preferably not less than 10 mol %, more preferably not less than 15 mol %, further preferably not less than 20 mol % from the viewpoint of dry grip performance, wet grip performance and rubber strength. On the other hand, the vinyl bond amount of SBR is preferably not more than 65 mol %, more preferably not more than 60 mol %, further preferably not more than 30 mol % from the viewpoint of fuel efficiency. It is noted that the vinyl bond amount of SBR herein refers to a vinyl bond amount of a butadiene part and is calculated from a $^1$H-NMR measurement.

The content of SBR in the rubber component is preferably not less than 10% by mass, more preferably not less than 20% by mass, further preferably not less than 30% by mass from the viewpoint of dry grip performance and wet grip performance. On the other hand, the content of SBR is preferably not more than 90% by mass, more preferably not more than 80% by mass from the viewpoint of abrasion resistance.

In particular, the modified SBR or modified BR, due to a strong interaction of its functional groups, coagulates itself and dispersion of a filler usually becomes all the more difficult. However, in the sixth invention, by divisionally kneading a specified coupling agent (D-6), the coagulation of the rubber component is prevented and the reaction with silica is promoted.

The rubber component may comprise, in addition to the above BR and SBR, a natural rubber (NR), an epoxidized natural rubber (ENR), an isoprene rubber (IR), a styrene-isoprene-butadiene rubber (SIBR) and the like as necessary. If the rubber composition comprises a rubber component other than SBR and BR, the rubber component is preferably added in the step X2-6 as described below.

Silica (B)

The silica (B-6) is not limited particularly and ones generally used in the tire industry can be used. Examples thereof include dry processed silica (silicic anhydride) and wet processed silica (hydrous silicic acid) and the like, and wet processed silica is preferable because it has more silanol groups.

The nitrogen adsorption specific surface area (N$_2$SA) of the silica (B-6) is preferably not less than 40 m$^2$/g, more preferably not less than 50 m$^2$/g, further preferably not less than 100 m$^2$/g, particularly preferably not less than 130 m$^2$/g, most preferably not less than 160 m$^2$/g from the viewpoint of breaking strength. On the other hand, the N$_2$SA of the silica (B-6) is preferably not more than 500 m$^2$/g, more preferably not more than 300 m$^2$/g, further preferably not more than 250 m$^2$/g, particularly preferably not more than 200 m$^2$/g from the viewpoint of fuel efficiency and processability. It is noted that the N$_2$SA of the silica (B-6) herein is a value as measured with the BET method in accordance with ATSM D3037-81.

The content (total added amount) of the silica (B-6) is preferably not less than 10 parts by mass, more preferably not less than 20 parts by mass, further preferably not less than 30 parts by mass, particularly preferably not less than 40 parts by mass based on 100 parts by mass of the rubber component (A-6) from the viewpoint of fuel efficiency and wet grip performance. On the other hand, the total content of the silica (B-6) is preferably not more than 200 parts by mass, more preferably not more than 150 parts by mass, further preferably not more than 120 parts by mass from the viewpoint of dispersibility of a filler into the rubber component and processability.

Carbon Black (C-6)

The carbon black (C-6) is not limited particularly and ones generally used in the tire industry such as GPF, FEF, HAF, ISAF, SAF and the like can be used, and these carbon black may be used alone, or may be used in combination with two or more thereof.

The nitrogen adsorption specific surface area (N$_2$SA) of the carbon black (C-6) is preferably not less than 80 m$^2$/g, more preferably not less than 100 m$^2$/g from the viewpoint of weather resistance and antistatic performance. On the other hand, the N$_2$SA of the carbon black (C-6) is preferably not more than 200 m$^2$/g, more preferably not more than 150 m$^2$/g from the viewpoint of processability. It is noted that the N$_2$SA of the carbon black (C-6) herein is a value as measured in accordance with JIS K6217, method A.

The content (total added amount) of the carbon black (C-6) is preferably not less than 1 part by mass, more preferably not less than 3 parts by mass based on 100 parts by mass of the rubber component (A-6). If the content of the carbon black (C-6) is less than 1 part by mass, the effect obtained by inclusion of the carbon black may not be obtained sufficiently. On the other hand, the content of the carbon black (C-6) is preferably not more than 30 parts by mass, more preferably not more than 10 parts by mass from the viewpoint of fuel efficiency and processability.

Coupling Agent (D-6)

The coupling agent (D-6) is a compound represented by the following chemical formula (1).

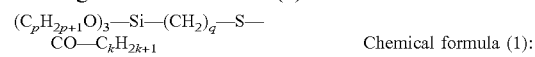

Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and cost. It is also possible that the coupling agent is used together with a general coupling agent other than the coupling agent (D) represented by the chemical formula (1).

The total content of the coupling agents (D-6) is preferably not less than 4 parts by mass, more preferably not less than 5 parts by mass, further preferably not less than 6 parts by mass based on 100 parts by mass of the total content of the silica from the viewpoint of the effect of improvement of a reaction with a filler and processability. On the other hand, the total content of the coupling agents (D-6) is preferably not more than 20 parts by mass, more preferably not more than 10 parts by mass, further preferably not more than 9 parts by mass from the viewpoint of the effect of improving dispersibility of silica that is compatible with the increase of cost.

Vulcanizing Agent (E-6)

The vulcanizing agent (E) comprises a vulcanizer (E1-6) and a vulcanization accelerator (E2-6). Vulcanizing agents generally used in the rubber industry such as a vulcanization accelerator auxiliary agent can be also used.

Vulcanizer (E1-6)

The vulcanizer (E1-6) is not limited particularly and ones generally used in the tire industry can be used. Since the effect of the sixth invention can be successfully obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of the vulcanizer (E1-6) is preferably not less than 0.1 part by mass, more preferably not less than 0.5 part by mass based on 100 parts by mass of the rubber component (A-6). On the other hand, the content of the vulcanizer (E1-6) is preferably not more than 15 parts by mass, more preferably not more than 5 parts by mass. If the content of the vulcanizer (E1-6) is within the above range, satisfactory tensile strength, abrasion resistance and heat resistance can be obtained.

Vulcanization Accelerator (E2-6)

The vulcanization accelerator (E2-6) is not limited particularly and ones generally used in the tire industry can be used. Examples thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolsulfenamide, N-t-butyl-2-benzothiazolsulfenamide, N-oxyethylene-2-benzothiazolsulfenamide, and N,N'-diisopropyl-2-benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-6) is preferably not less than 0.1 part by mass, more preferably not less than 0.2 part by mass based on 100 parts by mass of the rubber component (A-6). On the other hand, the content of the vulcanization accelerator (E2-6) is preferably not more than 5 parts by mass, more preferably not more than 3 parts by mass. If the content of the vulcanization accelerator (E2-6) is within the above range, the reduction of the elastic modulus of rubber and the deterioration of breaking resistance can be prevented.

Other Compounding Agents

The rubber composition for tire of the sixth invention can suitably comprise, in addition to the above components, compounding agents that have been used in the rubber industry such as, for example, a plasticizer (F-6), a filler for reinforcement other than silica and carbon black, an anti-aging agent (G-6), an antioxidant, a stearic acid, wax and the like as necessary.

Plasticizer (F-6)

Since processability is improved and the strength of rubber is increased, it is preferable that the rubber composition for tire of the sixth invention comprises the plasticizer (F-6). The plasticizer (F-6) is not limited particularly and ones generally used in the tire industry can be used, and examples thereof include oil, liquid polymer, liquid resin and the like. Among these, oil is preferable since the cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as the plasticizer (F-6), the content thereof based on 100 parts by mass of the rubber component (A-6) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-6)

The anti-aging agent (G-6) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises the anti-aging agent (G-6), the content thereof based on 100 parts by mass of the rubber component (A-6) is preferably not less than 0.5 part by mass, more preferably not less than 1.0 part by mass from the viewpoint of ozone resistance and crack resistance. On the other hand, the content of the anti-aging agent is preferably not more than 10 parts by mass, more preferably not more than 5 parts by mass from the viewpoint of prevention of discoloration.

Surfactant

In an embodiment of the sixth invention, it is preferable that the rubber composition further comprises a surfactant. By inclusion of a surfactant, dispersibility of the above fillers comprising silica and carbon black is improved and a discoloration of the obtained rubber composition for tire due to deterioration over time can be prevented.

Examples of the surfactant include metallic soap such as a metallic salt of an organic acid, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of the surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-6) from the viewpoint of the effect of improving dispersibility of silica. On the other hand, the content of the surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

Production Method of Rubber Composition for Tire

The production method of a rubber composition for tire of the sixth invention is characterized by dividing a kneading step into a step X1-6, a step X2-6 and a step F-6. Known kneaders can be used in each step and examples thereof include a Banbury mixer, a kneader, an open roll and the like.

Specifically, the production method of a rubber composition for tire includes a kneading process comprising a step X1-6 of kneading A1-6, a part of B-6, a part of D-6 and optionally a part of E-6, a step X2-6 of kneading the kneaded product of the step X1-6, A2-6, the remaining amount of B-6, the remaining amount of D-6 and optionally a part of E-6, and a step F-6 of kneading the kneaded product of the step X2-6 and the remaining amount of E-6, to obtain an unvulcanized rubber composition. The obtained unvulcanized rubber composition is then vulcanized (vulcanization process) and the rubber composition for tire according to the sixth invention can be produced. It is noted that the timing when other compounding agents such as carbon black (C-6), a plasticizer (F-6), an anti-aging agent (G-6), a zinc oxide, a stearic acid and the like are added and kneaded is not limited particularly, and these compounding agents may be added in any of the step X1-6, the step X2-6 or the step F-6, or may be added divisionally.

The production method of the sixth invention is also characterized in that the coupling agent (D-6) represented by the chemical formula (1) is divisionally kneaded. The coupling agent (D-6) can form homogeneous chemical bonds between the filler and the polymer without losing activity even in the kneading in the prior input as in the sixth invention because the coupling agent does not have a plurality of alkoxysilyl groups in the molecule and the coagulation thereof is small and also because a mercapto group suitably reacting with a polymer part becomes a fatty acid thioester, thereby non-uniformity resulting from a rapid reaction is prevented.

Step X1-6

In the step X1-6, compounding agents comprising the butadiene rubber (A1-6), a part of the silica (B-6), a part of the coupling agent (D-6) and optionally a part of the vulcanizing agent (E-6) are kneaded with a Banbury mixer or the like. In this step, the filler disperses while forming a strong bond with a rubber component, particularly with a rubber component having high affinity with the filler. Further, by use of a coupling agent (D-6) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane is used, then it releases sulfur even in this phase, thereby processability is deteriorated, dispersion of the filler is prevented and the activity of a coupling agent itself is lowered. The coupling agent (D-6) represented by the chemical formula (1) does not release sulfur, thereby being able to continue kneading while maintaining processability according to the production method of the sixth invention.

In the rubber composition comprising BR and SBR as a rubber component, the silica tends to be localized in SBR. However, in the production method of the sixth invention, by previously kneading BR, silica and a specified coupling agent in the step X1-6, the silica is allowed to also exist in the BR well.

The added amount of the silica (B-6) in the step X1-6 is preferably not less than 10% by mass, more preferably not less than 30% by mass, further preferably not less than 40% by mass, further preferably not less than 50% by mass of the total added amount of the silica (B-6) from the viewpoint of improvement of the effect of kneading silica, sufficient dispersion of silica and abrasion resistance. On the other hand, the added amount of the silica (B-6) in the step X1-6 is preferably not more than 95% by mass, more preferably not more than 90% by mass, further preferably not more than 85% by mass of the total added amount of the silica (B-6) from the viewpoint of the effect of adding the silica divisionally in the step X2-6 as described below, fuel efficiency and abrasion resistance.

The added amount of the coupling agent (D-6) represented by the chemical formula (1) in the step X1-6 is preferably not less than 4 parts by mass, more preferably not less than 5 parts by mass, further preferably not less than 6 parts by mass based on 100 parts by mass of the added amount of the silica (B-6) in the step X1-6, since a reaction with the filler becomes sufficient and the excellent effect of improving processability of the coupling agent (D-6) can be brought out. On the other hand, the added amount of the coupling agent (D-6) represented by the chemical formula (1) in the step X1-6 is preferably not more than 20 parts by mass, more preferably not more than 10 parts by mass, further preferably not more than 9 parts by mass from the viewpoint of the effect of improving dispersibility of silica that is compatible with the increase of the cost.

It is preferable that the carbon black (C) is added in the step X1-6 and/or the step X2-6. The added amount of the carbon black (C-6) in the step X1-6 is preferably not less than 10% by mass, more preferably not less than 50% by mass, further preferably not less than 80% by mass, most preferably 100% by mass of the total added amount of the carbon black (C-6) from the viewpoint of the improvement of dispersibility of carbon black and efficiency of the step. If the added amount of the carbon black (C-6) in the step X1-6 is less than 100% by mass, it is preferable that the remaining amount is added in the step X2-6.

While the step in which the plasticizer (F-6) is added is not limited particularly, it is preferable that not less than 50% by mass, more preferably not less than 70% by mass, further preferably not less than 80% by mass of the total added amount of the plasticizer (F-6) is added in the step X1-6. If the added amount of the plasticizer (F-6) in the step X1-6 is less than 100% by mass, it is preferable that the remaining amount is added in the step X2-6 since dispersibility of the silica which is added in the step X2-6 is more improved.

It is preferable that the surfactant is added in the step X1-6 and/or the step X2-6 from the viewpoint of promoting the effect of dispersing silica, and is preferably added in the step X1-6 since the effect of dispersing silica is more promoted and a gelation of the coupling agent can be prevented.

Step X2-6

In the step X2-6, the compounding agents comprising the styrene butadiene rubber (A2-6), the remaining amount of the silica (B-6), the remaining amount of the coupling agent (D-6) and optionally a part of the vulcanizing agent (E-6) are added to the kneaded product of the step X1-6 and the mixture is kneaded. If the all amount of the silica is added in the step X1-6, the silica tends to be localized in a polymer portion having high affinity with silica such as SBR and/or an interface portion of the polymer, however, in the production method of the sixth invention, since the silica is respectively input divisionally in the step X1-6 and the step X2-6, the silica is easily dispersed through the entire rubber component. Further, the later added silica (added in the step X2-6) itself has an effect of promoting kneading by applying shear to the rubber component. Moreover, in the production method of the sixth invention, since the coupling agent (D-6) represented by the chemical formula (1) is divisionally kneaded, an initial reduction of the activity of the coupling agent is prevented and processability throughout the kneading operation can be maintained.

The added amount of the coupling agent (D-6) represented by the chemical formula (1) in the step X2-6 is preferably not less than 4 parts by mass, more preferably not less than 5 parts by mass, further preferably not less than 6 parts by mass based on 100 parts by mass of the added amount of the silica (B-6) in the step X2-6 since the reaction with a filler can be made sufficient and the effect of improving excellent processability of the coupling agent (D-6) can be brought out. On the other hand, the added amount of the coupling agent (D-6) represented by the chemical formula (1) in the step X2-6 is preferably not more than 20 parts by mass, more preferably not more than 10 parts by mass, further preferably not more than 9 parts by mass from the viewpoint of the effect of improving dispersibility of silica that is compatible with the increase of cost.

The step in which the anti-aging agent (G-6) is added is not limited particularly, but from the viewpoint of operation efficiency and prevention of activity reduction of the anti-aging agent, it is preferable that all amount is added in the step X2-6.

The temperature at discharge of kneading in the step X1-6 and the step X2-6 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-6 and the step X2-6 is within the above range, the kneaded product in which silica (B) is well dispersed tends to be obtained efficiently.

The highest temperature during kneading in the step X1-6 and the step X2-6 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, by divisionally adding the coupling agent (D-6), a defect does not arise even if the kneading temperature becomes high and it is possible to promote the reaction of the coupling agent and promote the dispersion of the silica.

The kneading time in the step X1-6 and the step X2-6 is not limited particularly, but the kneading time is respectively preferably not less than 3.0 minutes, more preferably not less than 4.0 minutes, further preferably not less than 4.5 minutes since the kneaded product in which silica is well dispersed can be obtained efficiently. On the other hand, the respective kneading time is preferably not more than 9 minutes, more preferably not more than 8 minutes, further preferably not more than 7 minutes.

In one embodiment of the sixth invention, it is preferable to keep the kneaded product at 150 to 190° C. for 10 to 120 seconds after the temperature reaches the highest temperature in the step X1-6 and/or the step X2-6 and the kneading is finished since the reaction between the coupling agent and the silica is completely performed.

Step F-6

In the step F-6, the kneaded product obtained in the step X2-6 is cooled and then the vulcanizing agent (E-6) containing a vulcanizer and a vulcanization accelerator is added and the mixture is kneaded with an open roll and the like to obtain an unvulcanized rubber composition.

While the vulcanizing agent may be added in the step F-6 at a time, it is preferable that a part or all amount is added in the step X1-6 and/or the step X2-6 and then the remaining amount is added in the step F. By adding a part or all amount in the step X1-6 and/or the step X2-6, dispersion between the silica and the rubber component can be promoted. It is more preferable that a part or all amount of the guanidine vulcanization accelerator is added in the step X1-6 and/or the step X2-6 since dispersibility of the silica can be more promoted.

It is preferable that the kneaded product obtained in the step X2-6 is normally cooled to 100° C. or less, preferably to 20 to 80° C.

The temperature at discharge of kneading in the step F-6 is preferably not higher than 110° C., more preferably not higher than 100° C. If the temperature at discharge exceeds 110° C., a rubber burning (scorch) tends to easily arise. On the other hand, the lower limit of the temperature at discharge of kneading in the step F-6 is not limited particularly, but is preferably not lower than 80° C.

The kneading time in the step F-6 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-6 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the sixth invention can be obtained successfully.

Rubber Composition for Tire

The rubber composition for tire according to the sixth invention can be used for any component of a tire and among these, can be suitably used for a tread or a sidewall since it is the rubber composition for tire in which processability, fuel efficiency and abrasion resistance are improved in a good balance.

Tire

In addition, a tire of the sixth invention can be produced with a normal method by use of the rubber composition for tire according to the sixth invention. That is, the rubber composition for tire produced by the production method of the sixth invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the sixth invention can be produced. It is noted that the tire of the sixth invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars.

<Seventh Invention>

The seventh invention is a production method of a rubber composition for tire comprising a rubber component (A-7) comprising at least one selected from the group consisting of a natural rubber and a synthetic diene rubber, silica (B-7), carbon black 1 (C1-7) having a nitrogen adsorption specific surface area of not more than 200 m²/g, carbon black 2 (C2-7) having a nitrogen adsorption specific surface area of not less than 900 m²/g, a coupling agent (D1-7) represented by the following chemical formula (1), a coupling agent (D2-7) having a sulfide group, and a vulcanizing agent (E-7) comprising a vulcanizer and a vulcanization accelerator, the method comprising:

(step X1-7) a step X1-7 of kneading A-7, a part or all amount of B-7, C1-7, D1-7 and optionally a part of E, (step X2-7) a step X2-7 of kneading the kneaded product of the step X1-7, the remaining amount of B-7, C2-7, D2-7 and optionally a part of E-7, and (step F-7) a step F-7 of kneading the kneaded product of the step X2-7 and the remaining amount of E-7.

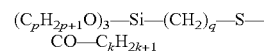

Chemical formula (1):

In the chemical formula (1), p represents an integer of 1 to 3, q represents an integer of 1 to 5, and k represents an integer of 5 to 12.

It is preferable that the rubber component comprises a styrene butadiene rubber and/or a butadiene rubber which has a functional group that reacts with silica.

It is preferable that the DBP oil absorption amount of the carbon black 2 (C2-7) is not less than 300 ml/100 g.

It is preferable that the volume specific resistivity of the rubber composition is less than $1.0 \times 10^7$ Ω·cm.

It is preferable that the added amount of silica in the step X1-7 is 50 to 95% by mass of the total added amount of silica.

It is preferable that the production method is a production method of the rubber composition further comprising a plasticizer and not less than 50% by mass of the total added amount of a plasticizer is kneaded in the step X1-7.

It is preferable that the highest temperature in the step X1-7 is 140 to 200° C.

It is preferable that after the kneading in the step X1-7 is finished, the production method comprises a step of keeping the kneaded product at 150 to 190° C. for 10 to 120 seconds.

It is preferable that a part or all amount of the vulcanization accelerator is kneaded in the step X1-7 and/or the step X2-7.

It is preferable that the production method is a production method of the rubber composition further comprising an anti-aging agent and the anti-aging agent is kneaded in the step X2-7.

It is preferable that the production method is a production method of the rubber composition further comprising a surfactant and the surfactant is kneaded in the step X1-7 and/or the step X2-7.

The seventh invention also relates to a tire having a tire component composed of the rubber composition for tire produced by the above production method of the rubber composition for tire.

According to the seventh invention, it is possible to produce a rubber composition for tire in which fuel efficiency, abrasion resistance, wet grip performance and electrical conductivity are improved in a good balance. Further, by use of a tire having a tire component composed of the produced rubber composition for tire, it is possible to produce a tire in which fuel efficiency, abrasion resistance, wet grip performance and electrical conductivity are improved in a good balance.

The rubber composition according to the seventh invention is characterized by comprising a specified rubber component (A-7), silica (B-7), carbon black (C1-7) and (C2-7) respectively having a specified nitrogen adsorption specific surface area, coupling agents (D1-7) and (D2-7), and a vulcanizing agent (E-7) comprising a vulcanizer and a vulcanization accelerator.

Rubber Component (A-7)

The rubber component (A-7) is characterized by comprising at least one selected from the group consisting of a natural rubber and a synthetic diene rubber, preferably comprising two or more thereof. By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The natural rubber includes a natural rubber (NR), and a modified natural rubber such as an epoxidized natural rubber (ENR), a hydrogenated natural rubber (HNR), a deproteinized natural rubber (DPNR), a high purity natural rubber (HPNR) and the like.

The NR is not limited particularly and those generally used in the tire industry such as SIR20, RSS#3, TSR20 and the like can be used.

In the case where the rubber composition comprises NR, the content thereof in the rubber component (A-7) is preferably not less than 5% by mass, more preferably not less than 10% by mass since breaking resistance of the rubber composition improves. On the other hand, the content of NR is preferably not more than 80% by mass, more preferably not more than 70% by mass, further preferably not more than 50% by mass since fuel efficiency and abrasion resistance of the rubber composition are excellent.

Examples of the synthetic diene rubber include an isoprene rubber (IR), a styrene butadiene rubber (SBR), a butadiene rubber (BR), a styrene-isoprene-butadiene rubber (SIBR) and the like.

Among synthetic diene rubbers, it is preferable that the rubber composition comprises SBR since it is excellent in processability, dry grip performance and wet grip performance. The SBR is not limited particularly and examples thereof include an unmodified solution-polymerized styrene-butadiene rubber (S-SBR), an unmodified emulsion-polymerized styrene-butadiene rubber (E-SBR), and modified SBRs of these (modified E-SBR, modified S-SBR) and the like. Examples of the modified SBR include a modified SBR in which a terminal and/or a main chain is modified, a modified SBR coupled by a tin or silicon compound (such as a condensate or one having a branched structure) and the like. Among these SBRs, S-SBR and modified S-SBR are preferable since they can improve grip performance and abrasion resistance in a good balance, and from the viewpoint of a reaction with silica, a modified SBR having at least one selected from the group consisting of a silyl group, an amino group, an amide group, a hydroxyl group and an epoxy group is particularly preferable. While these SBRs can be used alone, a use of SBRs having different physical properties such as a content of styrene is also possible depending on its application. It is noted that SBRs may be appropriately selected depending on a part to which they are applied.

The styrene content of SBR is preferably not less than 5% by mass, more preferably not less than 10% by mass, further preferably not less than 20% by mass from the viewpoint of dry grip performance, wet grip performance and rubber strength. On the other hand, the styrene content of SBR is preferably not more than 60% by mass, more preferably not more than 50% by mass, further preferably not more than 40% by mass from the viewpoint of fuel efficiency. It is noted that the styrene content of SBR herein is calculated from a $^1$H-NMR measurement.

The vinyl bond amount of SBR is preferably not less than 10 mol %, more preferably not less than 15 mol %, further preferably not less than 20 mol % from the viewpoint of dry grip performance, wet grip performance and rubber strength. On the other hand, the vinyl bond amount of SBR is preferably not more than 65 mol %, more preferably not more than 60 mol %, further preferably not more than 30 mol % from the viewpoint of fuel efficiency. It is noted that the vinyl bond amount of SBR herein refers to a vinyl bond amount of a butadiene part and is calculated from a measurement of dry grip performance and wet grip performance.

In the case where the rubber composition comprises SBR, the content thereof in the rubber component (A-7) is preferably not less than 10% by mass, more preferably not less than 20% by mass, further preferably not less than 30% by mass from the viewpoint of dry grip performance and wet grip performance. On the other hand, the content of SBR is preferably not more than 90% by mass, more preferably not more than 80% by mass from the viewpoint of abrasion resistance.

Further, it is preferable that the rubber component comprises BR since it is excellent in abrasion resistance. In general, a rubber composition in which a white filler such as silica (B-7) is compounded in BR has a problem that dispersibility of the filler is low and it is difficult to obtain desired performance. However, in the seventh invention, the reaction between a filler and a rubber component is improved by divisionally kneading a specified coupling agent. Accordingly, dispersibility of a filler increases and fuel efficiency and abrasion resistance are improved as well as satisfactory processability can be obtained, thereby synergistically improving a balance among these performances.

Examples of the BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

In the case where the rubber composition comprises BR, the content thereof in the rubber component (A-7) is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75% by mass, further preferably not more than 70% by mass from the viewpoint of processability.

In particular, the modified SBR or modified BR, due to a strong interaction of its functional groups, coagulates itself and dispersion of a filler usually becomes all the more difficult. However, in the seventh invention, by divisionally kneading a specified coupling agent (D-7), the coagulation of the rubber component is prevented and the reaction with silica is promoted.

Silica (B-7)

The silica (B-7) is not limited particularly and ones generally used in the tire industry can be used. Examples thereof include dry processed silica (silicic anhydride) and wet processed silica (hydrous silicic acid) and the like, and wet processed silica is preferable because it has more silanol groups.

The nitrogen adsorption specific surface area ($N_2SA$) of the silica (B-7) is preferably not less than 40 $m^2/g$, more preferably not less than 50 $m^2/g$, further preferably not less than 100 $m^2/g$, particularly preferably not less than 130 $m^2/g$, most preferably not less than 160 $m^2/g$ from the viewpoint of breaking strength. On the other hand, the $N_2SA$ of the silica (B-7) is preferably not more than 500 $m^2/g$, more preferably not more than 300 $m^2/g$, further preferably not more than 250 $m^2/g$, particularly preferably not more than 200 $m^2/g$ from the viewpoint of fuel efficiency and processability. It is noted that the $N_2SA$ of the silica (B-7) herein is a value as measured with the BET method in accordance with ATSM D3037-81.

The content (total added amount) of the silica (B-7) is preferably not less than 10 parts by mass, more preferably not less than 20 parts by mass, further preferably not less than 30 parts by mass, particularly preferably not less than 40 parts by mass based on 100 parts by mass of the rubber component (A-7) from the viewpoint of fuel efficiency and wet grip performance. On the other hand, the content of the silica (B-7) is preferably not more than 200 parts by mass, more preferably not more than 150 parts by mass, further preferably not more than 120 parts by mass from the viewpoint of dispersibility of a filler into the rubber component and processability.

Carbon Black

The rubber composition for tire according to the seventh invention is characterized by comprising carbon black 1 (C1-7) having a nitrogen adsorption specific surface area ($N_2SA$) of not more than 200 $m^2/g$ and carbon black 2 (C2-7) having a $N_2SA$ of not less than 900 $m^2/g$ as carbon black. By the combined use of the carbon black 1 and the carbon black 2, fuel efficiency, abrasion resistance, wet grip performance and electrical conductivity can be improved in a good balance. It is noted that carbon black other than the carbon black 1 (C1-7) and the carbon black 2 (C2-7) may be also used in combination.

The carbon black 1 (C1-7) is not limited particularly as long as it has a nitrogen adsorption specific surface area ($N_2SA$) of not more than 200 $m^2/g$ and ones generally used in the tire industry such as GPF, FEF, HAF, ISAF, SAF and the like can be used, and these carbon black may be used alone, or may be used in combination with two or more thereof.

The nitrogen adsorption specific surface area ($N_2SA$) of the carbon black 1 (C1-7) is preferably not less than 80 $m^2/g$, more preferably not less than 100 $m^2/g$ from the viewpoint of weather resistance and electrical conductivity. On the other hand, the $N_2SA$ of the carbon black 1 (C1-7) is not more than 200 $m^2/g$, preferably not more than 150 $m^2/g$. If the $N_2SA$ of the carbon black 1 (C1-7) exceeds 200 $m^2/g$, processability tends to deteriorate. It is noted that the $N_2SA$ of the carbon black herein is a value as measured in accordance with JIS K6217, method A.

The dibutyl phthalate (DBP) oil adsorption amount of the carbon black 1 (C1-7) is preferably not less than 60 ml/100 g, more preferably not less than 70 ml/100 g from the viewpoint of reinforcing property and braking resistance. On the other hand, the dibutyl phthalate (DBP) oil adsorption amount of the carbon black 1 (C1-7) is preferably not more than 130 ml/100 g, more preferably not more than 120 ml/100 g from the viewpoint of the tensile elongation at break, braking resistance and durability. It is noted that the DBP oil adsorption amount herein is a value calculated from a measurement method of JIS K6217-4.

The content of the carbon black 1 (C1-7) is preferably not less than 1 part by mass, more preferably not less than 5 parts by mass, further preferably not less than 8 parts by mass based on 100 parts by mass of the rubber component (A-7) from the viewpoint of the effect obtained by inclusion of the carbon black. On the other hand, the content of the carbon black 1 (C1-7) is preferably not more than 30 parts by mass, more preferably not more than 20 parts by mass from the viewpoint of fuel efficiency.

The carbon black 2 (C2-7) is what is called electrically conductive carbon black and according to the production method of the rubber composition of the seventh invention which comprises the carbon black 2 (C2-7), it is possible to easily improve fuel efficiency and electrical conductivity in a good balance.

The nitrogen adsorption specific surface area ($N_2SA$) of the carbon black 2 (C2-7) is not less than 900 $m^2/g$, preferably not less than 1,000 $m^2/g$, more preferably not less than 1,050 $m^2/g$. If the $N_2SA$ is less than 900 $m^2/g$, sufficient electrical conductivity tends not to be obtained. On the other hand, the $N_2SA$ of the carbon black 2 (C2-7) is preferably not more than 1,200 $m^2/g$, more preferably not more than 1,150 $m^2/g$, further preferably not more than 1,100 $m^2/g$ from the viewpoint of fuel efficiency, dispersibility, breaking resistance and durability.

The DBP oil adsorption amount of the carbon black 2 (C2-7) is preferably not less than 300 ml/100 g, more preferably not less than 350 ml/100 g from the viewpoint of electrical conductivity. On the other hand, the DBP oil adsorption amount of the carbon black 2 (C2-7) is preferably not more than 600 ml/100 g, more preferably not more than 500 ml/100 g, further preferably not more than 450 ml/100 g from the viewpoint of braking resistance and durability.

Examples of a suitable commercially available product of carbon black 2 (C2-7) include LIONITE ($N_2SA$: 1,052 $m^2/g$, DBP: 378 ml/100 g) manufactured by Lion Corporation, KETJENBLACK EC300J ($N_2SA$: 800 $m^2/g$, DBP: 365 ml/100 g) manufactured by Lion Corporation, PRINTEX XE2B ($N_2SA$: 1,000 $m^2/g$, DBP: 420 ml/100 g) manufactured by Evonik Industries and the like.

The content of the carbon black 2 (C2-7) is preferably not less than 0.5 part by mass, more preferably not less than 1.0 part by mass, further preferably not less than 2.0 parts by mass based on 100 parts by mass of the rubber component (A-7) from the viewpoint of electrical conductivity. On the other hand, the content of the carbon black 2 (C2-7) is preferably not more than 20 parts by mass, more preferably not more than 10 parts by mass from the viewpoint of fuel efficiency and the cost.

Coupling Agent

The coupling agent (D1-7) is a compound represented by the following chemical formula (1).

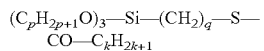

$(C_pH_{2p+1}O)_3$—Si—$(CH_2)_q$—S—CO—$C_kH_{2k+1}$  Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D1-7) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and the cost.

The coupling agent (D2-7) is a coupling agent having a sulfide group and examples thereof include bis(3-triethoxysilylpropyl)tetrasulfide, bis(2-triethoxysilylethyl)tetrasulfide, bis(3-trimethoxysilylpropyl)tetrasulfide, bis(2-trimethoxysilylethyl)tetrasulfide, bis(3-triethoxysilylpropyl)trisulfide, bis(3-trimethoxysilylpropyl)trisulfide, bis(3-triethoxysilylpropyl)disulfide, bis(3-trimethoxysilylpropyl)disulfide, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 2-trimethoxysilylethyl-N,N-dimethylthiocarbamoyl tetrasulfide, 3-trimethoxysilylpropylbenzothiazolyl tetrasulfide, 3-triethoxysilylpropylbenzothiazole tetrasulfide, 3-triethoxysilylpropyl methacrylate monosulfide, 3-trimethoxysilylpropyl methacrylate monosulfide and the like. Suitable examples of these coupling agents include Si75 (bis(3-triethoxysilylpropyl)disulfide), Si69 (bis(3-triethoxysilylpropyl)tetrasulfide) manufactured by Evonik Industries, which are available as a mixture that generally has a certain distribution, and the like.

The total content of the coupling agents (D1-7) and (D2-7) is preferably not less than 4 parts by mass, more preferably not less than 5 parts by mass, further preferably not less than 6 parts by mass based on 100 parts by mass of the total content of the silica from the viewpoint of the effect of improvement of a reaction with a filler and processability. On the other hand, the total content of the coupling agents is preferably not more than 20 parts by mass, more preferably not more than 10 parts by mass, further preferably not more than 9 parts by mass from the viewpoint of the effect of improving dispersibility of silica that is compatible with the increase of cost.

Vulcanizing Agent (E-7)

The vulcanizing agent (E-7) comprises a vulcanizer (E1-7) and a vulcanization accelerator (E2-7). Vulcanizing agents generally used in the rubber industry such as a vulcanization accelerator auxiliary agent can be also used.

Vulcanizer (E1-7)

The vulcanizer (E1-7) is not limited particularly and ones generally used in the tire industry can be used. Since the effect of the seventh invention can be successfully obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of the vulcanizer (E1-7) is preferably not less than 0.1 part by mass, more preferably not less than 0.5 part by mass based on 100 parts by mass of the rubber component (A-7). On the other hand, the content of the vulcanizer (E1-7) is preferably not more than 15 parts by mass, more preferably not more than 5 parts by mass. If the content of the vulcanizer (E1-7) is within the above range, satisfactory tensile strength, abrasion resistance and heat resistance can be obtained.

Vulcanization Accelerator (E2-7)

The vulcanization accelerator (E2-7) is not limited particularly and ones generally used in the tire industry can be used. Examples thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolsulfenamide, N-t-butyl-2-benzothiazolsulfenamide, N-oxyethylene-2-benzothiazolsulfenamide, and N,N'-diisopropyl-2-benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-7) is preferably not less than 0.1 part by mass, more preferably not less than 0.2 part by mass based on 100 parts by mass of the rubber component (A-7). On the other hand, the content of the vulcanization accelerator (E2-7) is preferably not more than 5 parts by mass, more preferably not more than 3 parts by mass. If the content of the vulcanization accelerator (E2-7) is within the above range, the reduction of the elastic modulus of rubber and the deterioration of breaking resistance can be prevented.

Other Compounding Agents

The rubber composition for tire of the seventh invention can suitably comprise, in addition to the above components, compounding agents that have been used in the rubber industry such as, for example, a plasticizer (F-7), a filler for reinforcement other than silica and carbon black, an anti-aging agent (G-7), an antioxidant, a stearic acid, wax and the like as necessary.

Plasticizer (F-7)

Since processability is improved and the strength of rubber is increased, it is preferable that the rubber composition for tire of the seventh invention comprises the plasticizer (F-7). The plasticizer (F-7) is not limited particularly and ones generally used in the tire industry can be used, and examples thereof include oil, liquid polymer, liquid resin and the like. Among these, oil is preferable since the cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as the plasticizer (F-7), the content thereof based on 100 parts by mass of the rubber component (A-7) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-7)

The anti-aging agent (G-7) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises the anti-aging agent (G-7), the content thereof based on 100 parts by mass of the rubber component (A-7) is preferably not less than 0.5 part by mass, more preferably not less than 1.0 part by mass from the viewpoint of ozone resistance and crack resistance. On the other hand, the content of the anti-aging agent is preferably not more than 10 parts by mass, more preferably not more than 5 parts by mass from the viewpoint of prevention of discoloration.

Surfactant

In an embodiment of the seventh invention, it is preferable that the rubber composition further comprises a surfactant. By inclusion of a surfactant, dispersibility of the above fillers comprising silica and carbon black is improved and a discoloration of the obtained rubber composition for tire due to deterioration over time can be prevented.

Examples of the surfactant include metallic soap such as a metallic salt of an organic acid, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of the surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-7) from the viewpoint of the effect of improving dispersibility of silica. On the other hand, the content of the surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

It is preferable that the volume specific resistivity of the rubber composition according to the seventh invention is less than $1.0 \times 10^7$ Ω·cm, more preferably not more than $1.0 \times 10^6$ Ω·cm since electrical conductivity can be obtained and a noise or spark due to static electricity can be prevented. It is noted that the volume specific resistivity herein is a value calculated by a measurement method of JIS K6271.

Production Method of Rubber Composition for Tire

The production method of a rubber composition for tire of the seventh invention is characterized by dividing a kneading step into a step X1-7, a step X2-7 and a step F. Known kneaders can be used in each step and examples thereof include a Banbury mixer, a kneader, an open roll and the like.

Specifically, the production method of a rubber composition for tire includes a kneading process comprising a step X1-7 of kneading A-7, a part or all amount of B-7, C1-7, D1-7 and optionally a part of E-7, a step X2-7 of kneading the kneaded product of the step X1-7, the remaining amount of B-7, C2-7, D2-7 and optionally a part of E-7, and a step F-7 of kneading the kneaded product of the step X2-7 and the remaining amount of E-7, to obtain an unvulcanized rubber composition. The obtained unvulcanized rubber composition is then vulcanized (vulcanization process) and the rubber composition for tire according to the seventh invention can be produced. It is noted that the timing when other compounding agents such as a plasticizer (F-7), an anti-aging agent (G-7), a zinc oxide, a stearic acid and the like are added and kneaded is not limited particularly, and these compounding agents may be added in any of the step X1-7, the step X2-7 or the step F-7, or may be added divisionally.

Particularly, the production method of the seventh invention is characterized in that the coupling agent (D1-7) is kneaded in the preceding step (step X1-7) before the coupling agent (D2-7) having a sulfide group is kneaded. The coupling agent (D1-7) can form homogeneous chemical bonds between the filler and the polymer without losing activity even in the kneading in the prior input as in the seventh invention because the coupling agent does not have a plurality of alkoxysilyl groups in the molecule and the coagulation thereof is small and also because a mercapto group suitably reacting with a polymer part becomes a fatty acid thioester, thereby non-uniformity resulting from a rapid reaction is prevented.

Step X1-7

In the step X1-7, compounding agents comprising all amount of the rubber component (A-7), a part or all amount of the silica (B-7), the carbon black 1 (C1-7), the coupling agent (D1-7) and optionally a part of the vulcanizing agent (E-7) are kneaded with a Banbury mixer or the like. In this step, the filler disperses while forming a strong bond with a rubber component, particularly with a rubber component having high affinity with the filler. Further, by use of a coupling agent (D1-7) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane (coupling agent (D2-7)) is added in the step X1, then it releases sulfur even in this phase, thereby processability is deteriorated, dispersion of the filler is prevented and the activity of a coupling agent itself is lowered. The coupling agent (D1-7) represented by the chemical formula (1) does not release sulfur, thereby being able to continue kneading while maintaining processability according to the production method of the seventh invention.

The added amount of the silica (B-7) in the step X1-7 is preferably not less than 10% by mass, more preferably not less than 30% by mass, further preferably not less than 40% by mass, further preferably not less than 50% by mass of the total added amount of the silica (B-7) from the viewpoint of improvement of the effect of kneading silica, sufficient dispersion of silica and abrasion resistance. On the other hand, the added amount of the silica (B-7) in the step X1-7 is preferably not more than 95% by mass, more preferably not more than 90% by mass, further preferably not more than 85% by mass of the total added amount of the silica (B-7) from the viewpoint of the effect of adding the silica divisionally in the step X2-7 as described below, fuel efficiency and abrasion resistance.

The added amount of the coupling agent (D1-7) represented by the chemical formula (1) in the step X1-7 is preferably not less than 4 parts by mass, more preferably not less than 5 parts by mass, further preferably not less than 6 parts by mass based on 100 parts by mass of the added amount of the silica (B-7) in the step X1-7, since a reaction with the filler becomes sufficient and the excellent effect of improving processability of the coupling agent (D1-7) can be exerted. On the other hand, the added amount of the coupling agent (D1-7) represented by the chemical formula (1) in the step X1-7 is preferably not more than 20 parts by mass, more preferably not more than 10 parts by mass, further preferably not more than 9 parts by mass from the viewpoint of the effect of improving dispersibility of silica that is compatible with the increase of the cost.

While the step in which the plasticizer (F-7) is added is not limited particularly, it is preferable that not less than 50% by mass, more preferably not less than 70% by mass, further preferably not less than 80% by mass of the total added amount of the plasticizer (F-7) is added in the step X1-7. If the added amount of the plasticizer (F-7) in the step X1-7 is less than 100% by mass, it is preferable that the remaining amount is added in the step X2-7 since dispersibility of the silica which is added in the step X2-7 is more improved.

It is preferable that the surfactant is added in the step X1-7 and/or the step X2-7 from the viewpoint of promoting the effect of dispersing silica, and is preferably added in the step X1-7 since the effect of dispersing silica is more promoted and a gelation of the coupling agent can be prevented.

The temperature at discharge of kneading in the step X1-7 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-7 is within the above range, the kneaded product in which silica (B-7) is well dispersed tends to be obtained efficiently.

The highest temperature during kneading in the step X1-7 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, polysulfide silane is not added as a vulcanization accelerator in the step X1-7 according to the seventh invention and thus a defect does not arise even if the kneading temperature becomes high and it is possible to promote the reaction of the coupling agent and promote the dispersion of the silica.

The kneading time in the step X1-7 is not limited particularly, but the kneading time in each step is preferably not less than 3.0 minutes, more preferably not less than 4.0 minutes, further preferably not less than 4.5 minutes since the kneaded product in which silica is well dispersed can be obtained efficiently. On the other hand, the respective kneading time in each step is preferably not more than 9 minutes, more preferably not more than 8 minutes, further preferably not more than 7 minutes.

In one embodiment of the seventh invention, it is preferable to keep the kneaded product at 150 to 190° C. for 10 to 120 seconds after the temperature reaches the highest temperature in the step X1-7 and the kneading is finished since the reaction between the coupling agent (D1-7) and the silica is completely performed.

Step X2-7

In the step X2-7, the compounding agents comprising the remaining amount of the silica (B-7), the carbon black 2 (C2-7), the coupling agent (D2-7) and optionally a part of the vulcanizing agent (E-7) are added to the kneaded product of the step X1-7 and the mixture is kneaded. If the carbon black 1 (C1-7) and the carbon black 2 (C2-7) are kneaded at the same time, there is a tendency that a kneading shear is excessively applied to the carbon black 2 and the network of electrically conductive carbon black is broken, thereby making electric conductivity and abrasion resistance insufficient. However, by adding the carbon black 2 (C2-7) after adding the carbon black 1 (C1-7), that is, by adding the carbon black 2 (C2-7) in the step X2-7, the dispersion of the carbon black 2 does not become excessive and a suitable network can be formed. Moreover, in the production method of the seventh invention, since the coupling agent (D1-7) represented by the chemical formula (1) is kneaded in the step X1-7, an initial reduction of the activity of the coupling agent is prevented and processability throughout the kneading operation can be maintained.

In addition, by kneading the coupling agent (D2-7) having a sulfide group in the step X2-7, an initial reduction of the activity of the coupling agent is prevented and processability throughout the kneading operation can be maintained. Moreover, since the coupling agent (D2-7) can release sulfur that acts as a vulcanizer, a uniform crosslinking is promoted and the improvement of physical properties of the rubber can be attempted.

The added amount of the coupling agent (D2-7) in the step X2-7 is preferably not less than 4 parts by mass, more preferably not less than 5 parts by mass, further preferably not less than 6 parts by mass based on 100 parts by mass of the added amount of the silica (B-7) in the step X2-7 since the reaction with the filler can be made sufficient and the excellent effect of improving processability of the coupling agent (D2-7) can be brought out. On the other hand, the added amount of the coupling agent (D2-7) represented by the chemical formula (1) in the step X2-7 is preferably not more than 20 parts by mass, more preferably not more than 10 parts by mass, further preferably not more than 9 parts by mass from the viewpoint of the effect of improving dispersibility of silica that is compatible with the increase of the cost.

The step in which the anti-aging agent (G-7) is added is not limited particularly, but from the viewpoint of operation efficiency and prevention of activity reduction of the anti-aging agent during the kneading, it is preferable that all amount is added in the step X2-7.

The temperature at discharge of kneading in the step X2-7 is not limited particularly, but is preferably not lower than 100° C., more preferably not lower than 120° C., further preferably not lower than 130° C. On the other hand, the temperature at discharge is preferably not higher than 200° C., more preferably not higher than 170° C., further preferably not higher than 160° C. If the temperature at discharge in the step X2-7 is within the above range, the kneaded product in which silica (B-7) is well dispersed tends to be obtained efficiently.

The highest temperature during kneading in the step X2-7 is not limited particularly, but is preferably not lower than 100° C., more preferably not lower than 120° C., further preferably not lower than 130° C. since the coupling agent (D2-7) is sufficiently reacted and the kneaded product in which the silica is well dispersed can be obtained efficiently. On the other hand, the highest temperature during kneading is preferably not higher than 200° C., more preferably not higher than 170° C., further preferably not higher than 160° C. for preventing a rubber burning.

The kneading time in the step X2-7 is not limited particularly, but the kneading time is preferably not less than 3.0 minutes since the kneaded product in which silica is well dispersed can be obtained efficiently. On the other hand, the respective kneading time is preferably not more than 9 minutes, more preferably not more than 8 minutes, further preferably not more than 7 minutes.

Step F-7

In the step F-7, the kneaded product obtained in the step X2-7 is cooled and then the vulcanizing agent (E-7) containing the vulcanizer and the vulcanization accelerator is added and the mixture is kneaded with an open roll or the like to obtain an unvulcanized rubber composition.

While the vulcanization accelerator may be added in the step F-7 at a time, it is preferable that a part or all amount is added in the step X1-7 and/or the step X2-7 and then the remaining amount is added in the step F-7. By adding a part or all amount in the step X1-7 and/or the step X2-7, dispersion between the silica and the rubber component can be promoted. It is more preferable that a part or all amount of the guanidine vulcanization accelerator is added in the step X1-7 and/or the step X2-7 since dispersibility of the silica can be more promoted.

It is preferable that the kneaded product obtained in the step X2-7 is normally cooled to 100° C. or less, preferably to 20 to 80° C.

The temperature at discharge of kneading in the step F-7 is preferably not higher than 110° C., more preferably not higher than 100° C. If the temperature at discharge exceeds 110° C., a rubber burning (scorch) tends to easily arise. On the other hand, the lower limit of the temperature at discharge of kneading in the step F-7 is not limited particularly, but is preferably not lower than 80° C.

The kneading time in the step F-7 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-7 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the seventh invention can be obtained successfully.

Rubber Composition for Tire

The rubber composition for tire according to the seventh invention can be used for any component of a tire and among these, can be suitably used for a tread or a sidewall since it is the rubber composition for tire in which processability, fuel efficiency, abrasion resistance, wet grip performance and electrical conductivity are improved in a good balance.

Tire

In addition, a tire of the seventh invention can be produced with a normal method by use of the rubber composition for tire according to the seventh invention. That is, the rubber composition for tire produced by the production method of the seventh invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the seventh invention can be produced.

It is noted that the tire of the seventh invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars. Additionally, examples of a non-pneumatic tire include a solid tire, an airless tire, a truck belt and the like.

One suitable embodiment of the seventh invention is an airless tire having a tread composed of the rubber composition for tire according to the seventh invention. In an airless tire, electrical conductivity throughout the tire tends to be inferior since an electrically conductive component such as a steel cord does not exist or a wheel is made of a resin, however, by using a tread comprising the rubber composition according to the seventh invention for an airless tire, satisfactory electrical conductivity can be obtained.

<Eighth Invention>

The eighth invention is a production method of a rubber composition for tire comprising a rubber component (A-8) comprising at least one selected from the group consisting of a natural rubber and a synthetic diene rubber, silica (B-8), carbon black (C-8), a coupling agent (D-8) represented by the following chemical formula (1), and a vulcanizing agent (E-8) comprising a vulcanizer and a vulcanization accelerator, the method comprising:

(step X1-8) a step X1-8 of kneading A-8, a part of B-8, a part of D-8 and optionally a part of E-8,
(step X2-8) a step X2-8 of kneading the kneaded product of the step X1-8, the remaining amount of B-8, the remaining amount of D-8 and optionally a part of E-8, and
(step F-8) a step F-8 of kneading the kneaded product of the step X2-8 and the remaining amount of E-8, wherein a part or all amount of the vulcanization accelerator is kneaded in the step X1-8 and/or the step X2-8.

Chemical formula (1):

In the chemical formula (1), p represents an integer of 1 to 3, q represents an integer of 1 to 5, and k represents an integer of 5 to 12.

It is preferable that the rubber component comprises a styrene butadiene rubber and/or a butadiene rubber which has a functional group that reacts with silica.

It is preferable that the nitrogen adsorption specific surface area of silica is not less than 160 $m^2/g$ and the total added amount of silica is not less than 40 parts by mass based on 100 parts by mass of the rubber component.

It is preferable that the added amount of the coupling agent in each of the step X1-8 and the step X2-8 is 4 to 10 parts by mass based on 100 parts by mass of the silica added in each step.

It is preferable that the added amount of silica in the step X1-8 is 50 to 95% by mass of the total added amount of silica.

It is preferable that the production method is a production method of the rubber composition further comprising a plasticizer and not less than 50% by mass of the total added amount of a plasticizer is kneaded in the step X1-8.

It is preferable that the highest temperature in the step X1-8 and/or the step X2-8 is 140° C. to 200° C.

It is preferable that after the kneading in the step X1-8 and/or the step X2-8 is finished, the production method comprises a step of keeping the kneaded product at 150 to 190° C. for 10 to 120 seconds.

It is preferable that a part of the vulcanization accelerator is kneaded in the step X1-8 and/or the step X2-8.

It is preferable that the production method is a production method of the rubber composition further comprising an anti-aging agent and an anti-aging agent is kneaded in the step X2-8.

It is preferable that the production method is a production method of the rubber composition further comprising a surfactant and a surfactant is kneaded in the step X1-8 and/or the step X2-8.

The eighth invention also relates to a tire having a tire component composed of the rubber composition for tire produced by the above production method of the rubber composition for tire.

According to the eighth invention, it is possible to produce a rubber composition for tire in which fuel efficiency, abrasion resistance and wet grip performance are improved in a good balance. Further, by use of a tire having a tire component composed of the produced rubber composition for tire, it is possible to produce a tire in which fuel efficiency, abrasion resistance and wet grip performance are improved in a good balance.

The rubber composition according to the eighth invention is characterized by comprising a specified rubber component (A-8), silica (B-8), carbon black (C-8), a specified coupling agent (D-8), and a vulcanizing agent (E-8) comprising a vulcanizer and a vulcanization accelerator.

Rubber Component (A-8)

The rubber component (A-8) is characterized by comprising at least one selected from the group consisting of a natural rubber and a synthetic diene rubber, preferably comprising two or more thereof. By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The natural rubber includes a natural rubber (NR), and a modified natural rubber such as an epoxidized natural rubber (ENR), a hydrogenated natural rubber (HNR), a deproteinized natural rubber (DPNR), a high purity natural rubber (HPNR) and the like.

The NR is not limited particularly and those generally used in the tire industry such as SIR20, RSS#3, TSR20 and the like can be used.

In the case where the rubber composition comprises NR, the content thereof in the rubber component (A-8) is preferably not less than 5% by mass, more preferably not less than 10% by mass since breaking resistance of the rubber composition improves. On the other hand, the content of NR is preferably not more than 80% by mass, more preferably not more than 70% by mass, further preferably not more than 50% by mass since fuel efficiency and abrasion resistance of the rubber composition are excellent.

Examples of the synthetic diene rubber include an isoprene rubber (IR), a styrene butadiene rubber (SBR), a butadiene rubber (BR), a styrene-isoprene-butadiene rubber (SIBR) and the like.

Among synthetic diene rubbers, it is preferable that the rubber composition comprises SBR since it is excellent in processability and grip performance. The SBR is not limited particularly and examples thereof include an unmodified solution-polymerized styrene-butadiene rubber (S-SBR), an unmodified emulsion-polymerized styrene-butadiene rubber (E-SBR), and modified SBRs of these (modified E-SBR, modified S-SBR) and the like. Examples of the modified SBR include a modified SBR in which a terminal and/or a main chain is modified, a modified SBR coupled by a tin or silicon compound (such as a condensate or one having a branched structure) and the like. Among these SBRs, S-SBR and modified S-SBR are preferable since they can improve grip performance and abrasion resistance in a good balance, and from the viewpoint of the reaction with silica, a modified SBR having at least one selected from the group consisting of a silyl group, an amino group, an amide group, a hydroxyl group and an epoxy group is particularly preferable. While these SBRs can be used alone, a use of SBRs having different physical properties such as a content of styrene is also possible depending on its application. It is noted that SBRs may be appropriately selected depending on a part to which they are applied.

The styrene content of SBR is preferably not less than 5% by mass, more preferably not less than 10% by mass, further preferably not less than 20% by mass from the viewpoint of dry grip performance, wet grip performance and rubber strength. On the other hand, the styrene content of SBR is preferably not more than 60% by mass, more preferably not more than 50% by mass, further preferably not more than 40% by mass from the viewpoint of fuel efficiency. It is noted that the styrene content of SBR herein is calculated from a $^1$H-NMR measurement.

The vinyl bond amount of SBR is preferably not less than 10 mol %, more preferably not less than 15 mol %, further preferably not less than 20 mol % from the viewpoint of dry grip performance, wet grip performance and rubber strength. On the other hand, the vinyl bond amount of SBR is preferably not more than 65 mol %, more preferably not more than 60 mol %, further preferably not more than 30 mol % from the viewpoint of fuel efficiency. It is noted that the vinyl bond amount of SBR herein refers to a vinyl bond amount of a butadiene part and is calculated from a $^1$H-NMR measurement.

In the case where the rubber composition comprises SBR, the content thereof in the rubber component (A-8) is preferably not less than 10% by mass, more preferably not less than 20% by mass, further preferably not less than 30% by mass from the viewpoint of dry grip performance and wet grip performance. On the other hand, the content of SBR is preferably not more than 90% by mass, more preferably not more than 80% by mass from the viewpoint of abrasion resistance.

Further, it is preferable that the rubber component comprises BR since it is excellent in abrasion resistance. In general, a rubber composition in which a white filler such as silica (B) is compounded in BR has a problem that dispersibility of the filler is low and it is difficult to obtain desired performance. However, in the eighth invention, the reaction between a filler and a rubber component is improved by divisionally kneading a specified coupling agent (D-8). Accordingly, dispersibility of a filler increases and fuel efficiency and abrasion resistance are improved as well as satisfactory processability can be obtained, thereby synergistically improving a balance among these performances.

Examples of the BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of the achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

In the case where the rubber composition comprises BR, the content thereof in the rubber component (A-8) is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75% by mass, further preferably not more than 70% by mass from the viewpoint of processability.

In particular, the modified SBR or modified BR, due to a strong interaction of its functional groups, coagulates itself and dispersion of a filler usually becomes all the more difficult. However, in the eighth invention, by divisionally kneading a specified coupling agent (D-8), the coagulation of the rubber component is prevented and the reaction with silica is promoted.

Silica (B-8)

The silica (B-8) is not limited particularly and ones generally used in the tire industry can be used. Examples thereof include dry processed silica (silicic anhydride) and wet processed silica (hydrous silicic acid) and the like, and wet processed silica is preferable because it has more silanol groups.

The nitrogen adsorption specific surface area ($N_2SA$) of the silica (B-8) is preferably not less than 40 m$^2$/g, more preferably not less than 50 m$^2$/g, further preferably not less than 100 m$^2$/g, particularly preferably not less than 130 m$^2$/g, most preferably not less than 160 m$^2$/g from the viewpoint of breaking resistance. On the other hand, the $N_2SA$ of the silica (B-8) is preferably not more than 500 m$^2$/g, more preferably not more than 300 m$^2$/g, further preferably not more than 250 m$^2$/g, particularly preferably not more than 200 m$^2$/g from the viewpoint of fuel efficiency and processability. It is noted that the $N_2SA$ of the silica (B-8) herein is a value as measured with the BET method in accordance with ATSM D3037-81.

The total content of the silica (B-8) is preferably not less than 10 parts by mass, more preferably not less than 20 parts by mass, further preferably not less than 30 parts by mass, particularly preferably not less than 40 parts by mass based on 100 parts by mass of the rubber component (A-8) from the viewpoint of fuel efficiency and wet grip performance. On the other hand, the total content of the silica (B-8) is preferably not more than 200 parts by mass, more preferably not more than 150 parts by mass, further preferably not more than 120 parts by mass from the viewpoint of dispersibility of a filler into the rubber component and processability.

Carbon Black (C-8)

The carbon black (C-8) is not limited particularly and ones generally used in the tire industry such as GPF, FEF, HAF, ISAF, SAF and the like can be used, and these carbon black may be used alone, or may be used in combination with two or more thereof.

The nitrogen adsorption specific surface area ($N_2SA$) of the carbon black (C-8) is preferably not less than 80 m$^2$/g, more preferably not less than 100 m²/g from the viewpoint of weather resistance and antistatic performance. On the other hand, the N₂SA of the carbon black (C-8) is preferably not more than 200 m²/g, more preferably not more than 150 m²/g from the viewpoint of processability. It is noted that the N₂SA of the carbon black (C-8) herein is a value as measured in accordance with JIS K6217, method A.

The content (total added amount) of the carbon black (C-8) is preferably not less than 1 part by mass, more preferably not less than 3 parts by mass based on 100 parts by mass of the rubber component (A-8). If the content of the carbon black (C) is less than 1 part by mass, the effect obtained by inclusion of the carbon black (C-8) may not be obtained sufficiently. On the other hand, the content of the carbon black (C-8) is preferably not more than 30 parts by mass, more preferably not more than 10 parts by mass from the viewpoint of fuel efficiency and processability.

Coupling Agent (D-8)

The specified coupling agent (D-8) is a compound represented by the following chemical formula (1).

Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D-8) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and cost. It is also possible that the coupling agent is used together with a general coupling agent other than the coupling agent (D) represented by the chemical formula (1).

The total content of the coupling agent (D-8) represented by the chemical formula (1) is preferably not less than 4 parts by mass, more preferably not less than 5 parts by mass, further preferably not less than 6 parts by mass based on 100 parts by mass of the total content of the silica from the viewpoint of the effect of improvement of a reaction with a filler and processability. On the other hand, the content of the coupling agent (D-8) is preferably not more than 20 parts by mass, more preferably not more than 10 parts by mass, further preferably not more than 9 parts by mass from the viewpoint of the effect of improving dispersibility of silica that is compatible with the increase of the cost.

Vulcanizing Agents (E-8)

The vulcanizing agents (E-8) comprise a vulcanizer (E1-8) and a vulcanization accelerator (E2-8). Vulcanizing agents generally used in the rubber industry such as a vulcanization accelerator auxiliary agent can be also used.

Vulcanizer (E1-8)

The vulcanizer (E1-8) is not limited particularly and ones generally used in the tire industry can be used. Since the effect of the eighth invention can be sufficiently obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of the vulcanizer (E1-8) is preferably not less than 0.1 part by mass, more preferably not less than 0.5 part by mass based on 100 parts by mass of the rubber component (A-8). On the other hand, the content of the vulcanizer (E1-8) is preferably not more than 15 parts by mass, more preferably not more than 5 parts by mass. If the content of the vulcanizer (E1-8) is within the above range, satisfactory tensile strength, abrasion resistance and heat resistance can be obtained.

Vulcanization Accelerator (E2-8)

The vulcanization accelerator (E2-8) is not limited particularly and ones generally used in the tire industry can be used. Examples thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolsulfenamide, N-t-butyl-2-benzothiazolsulfenamide, N-oxyethylene-2-benzothiazolsulfenamide, and N,N'-diisopropyl-2-benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-8) is preferably not less than 0.1 part by mass, more preferably not less than 0.2 part by mass based on 100 parts by mass of the rubber component (A-8). On the other hand, the content of the vulcanization accelerator (E2-8) is preferably not more than 5 parts by mass, more preferably not more than 3 parts by mass. If the content of the vulcanization accelerator (E2-8) is within the above range, the reduction of the rubber elastic modulus and the deterioration of breaking resistance can be prevented.

Other Compounding Agents

The rubber composition for tire of the eighth can suitably comprise, in addition to the above components, compounding agents that have been used in the rubber industry such as, for example, a plasticizer (F-8), a filler for reinforcement other than silica and carbon black, an anti-aging agent (G-8), an antioxidant, a stearic acid, wax and the like as necessary.

Plasticizer (F-8)

Since processability is improved and the strength of rubber is increased, it is preferable that the rubber composition for tire of the eighth invention comprises the plasticizer (F-8). The plasticizer (F-8) is not limited particularly and ones generally used in the tire industry can be used, and examples thereof include oil, liquid polymer, liquid resin and the like. Among these, oil is preferable since cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as the plasticizer (F-8), the content thereof based on 100 parts by mass of the rubber component (A-8) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-8)

The anti-aging agent (G-8) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises the anti-aging agent (G-8), the content thereof based on 100 parts by mass of the rubber component (A-8) is preferably not less than 0.5 part by mass, more preferably not less than 1.0 part by mass from the viewpoint of ozone resistance and crack resistance. On the other hand, the content of the anti-aging agent is preferably not more than 10 parts by mass, more preferably not more than 5 parts by mass from the viewpoint of prevention of discoloration.

Surfactant

In an embodiment of the eighth invention, it is preferable that the rubber composition further comprises a surfactant. By inclusion of a surfactant, dispersibility of the above fillers comprising silica and carbon black is improved and a discoloration of the obtained rubber composition for tire due to deterioration over time can be prevented.

Examples of the surfactant include metallic soap such as an organic acid of a metallic salt, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of the surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-8) from the viewpoint of the effect of improving dispersibility of silica. On the other hand, the content of the surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

Production Method of Rubber Composition for Tire

The production method of a rubber composition for tire of the eighth invention is characterized by dividing a kneading step into a step X1-8, a step X2-8 and a step F-8. Known kneaders can be used in each step and examples thereof include a Banbury mixer, a kneader, an open roll and the like.

Specifically, the production method of a rubber composition for tire includes a kneading process comprising a step X1-8 of kneading A-8, a part of B-8, a part of D-8 and optionally a part of E-8, a step X2-8 of kneading the kneaded product of the step X1-8, the remaining amount of B-8, the remaining amount of D-8 and optionally a part of E-8, and a step F-8 of kneading the kneaded product of the step X2-8 and the remaining amount of the vulcanizing agent E-8, to obtain an unvulcanized rubber composition, wherein a part or all amount of the vulcanization accelerator is kneaded in the step X1-8 and/or the step X2-8. The obtained unvulcanized rubber composition is then vulcanized (vulcanization process) and the rubber composition for tire according to the eighth invention can be produced. It is noted that the timing when other compounding agents such as carbon black (C-8), a plasticizer (F-8), an anti-aging agent (G-8), a zinc oxide, a stearic acid and the like are added and kneaded is not limited particularly, and these compounding agents may be added in any of the step X1-8, the step X2-8 or the step F-8, or may be added divisionally.

In the production method of the eighth invention, it is particularly characteristic that the coupling agent (D-8) represented by the chemical formula (1) is divisionally kneaded. Since a plurality of alkoxysilyl groups do not exist in the molecule of the coupling agent (D-8), the coagulation of the coupling agent is small and a mercapto group that suitably reacts with a polymer part becomes a fatty acid thioester, thereby non-uniformity involved in a rapid reaction is prevented and even in the kneading as in the eighth invention where the coupling agent is divisionally input, it is possible to form a uniform chemical bond between the filler and the polymer without losing activity.

Step X1-8

In the step X1-8, compounding agents comprising all amount of the rubber component (A-8), a part of the silica (B-8), a part of the coupling agent (D-8) and optionally a part of the vulcanizing agent (E-8) are kneaded with a Banbury mixer and the like. From this step, the filler disperses while forming a strong bond with a rubber component, particularly with a rubber component having high affinity with the filler. Further, by use of a coupling agent (D-8) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane is used, then it releases sulfur even in this phase, thereby processability is deteriorated, dispersion of the filler is prevented and the activity of a coupling agent itself is lowered. The coupling agent (D-8) represented by the chemical formula (1) does not release sulfur, thereby being able to continue kneading while maintaining processability according to the production method of the eighth invention.

The added amount of the silica (B-8) in the step X1-8 is preferably not less than 50% by mass, more preferably not less than 60% by mass, further preferably not less than 70% by mass, particularly preferably not less than 80% by mass of the total added amount of the silica (B-8) from the viewpoint of improvement of the effect of kneading silica, sufficient dispersion of silica and abrasion resistance. On the other hand, the added amount of the silica (B-8) in the step X1-8 is preferably not more than 95% by mass, more preferably not more than 90% by mass of the total added amount of the silica (B-8) from the viewpoint of the effect of adding the silica divisionally in the step X2-8 described below, fuel efficiency and abrasion resistance.

The added amount of the coupling agent (D-8) in the step X1-8 is preferably not less than 4 parts by mass, more preferably not less than 5 parts by mass, further preferably not less than 6 parts by mass based on 100 parts by mass of the added amount of the silica (B-8) in the step X1-8, since a reaction with the filler becomes sufficient and the excellent effect of improving processability of the coupling agent (D-8) can be exerted. On the other hand, the added amount of the coupling agent (D-8) in the step X1-8 is preferably not more than 20 parts by mass, more preferably not more than 10 parts by mass, further preferably not more than 9 parts by mass from the viewpoint of the effect of improving dispersibility of silica that is compatible with the increase of cost.

It is preferable that the carbon black (C-8) is added in the step X1-8 and/or in the step X2-8. The added amount of the carbon black (C-8) in the step X1-8 is preferably not less than 10% by mass, more preferably not less than 50% by mass, further preferably not less than 80% by mass, most preferably 100% by mass of the total added amount of the carbon black (C-8) from the viewpoint of improvement of dispersibility of carbon black and efficiency of the step. If the added amount of the carbon black (C-8) in the step X1-8 is less than 100% by mass, it is preferable that the remaining amount is added in the step X2-8.

By kneading a part or all amount of the vulcanization accelerator (E2-8) in the step X1-8 and/or the step X2-8, the dispersion between the silica and the rubber component can be more promoted. It is more preferably that particularly a part or all amount of the guanidine vulcanization accelerator is added in the step X1-8 and/or the step X2-8 since dispersibility of the silica can be more promoted. A part of the vulcanization accelerator (E2-8) is preferably kneaded in the step X1-8 or the step X2-8, more preferably kneaded in the step X1-8.

While the step in which the plasticizer (F-8) is added is not limited particularly, it is preferable that not less than 50% by mass, more preferably not less than 70% by mass, further preferably not less than 80% by mass of the total added amount of the plasticizer (F-8) is added in the step X1-8. If the added amount of the plasticizer (F-8) in the step X1-8 is less than 100% by mass, it is preferable that the remaining amount is added in the step X2-8 since dispersibility of the silica which is added in the step X2-8 is more improved.

It is preferable that the surfactant is added in the step X1-8 and/or the step X2-8 from the viewpoint of promoting the effect of dispersing silica, and is preferably added in the step X1-8 since the effect of dispersing silica is more promoted and a gelation of the coupling agent can be prevented.

Step X2-8

In the step X2-8, the remaining amount of the silica (B-8), the remaining amount of the coupling agent (D-8), optionally a part of the vulcanizing agent (E-8) and other compounding agents are added to the kneaded product of the step X1-8 and the mixture is kneaded. If the all amount of the silica (B-8) is added in the step X1-1, the silica tends to be localized in a polymer portion having high affinity with silica such as a modified polymer and/or an interface portion of the polymer, however, in the production method of the eighth invention, since the silica is divisionally input in each of the step X1-8 and the step X2-8, the silica becomes easily dispersed through the entire rubber component. Further, the later added silica (added in the step X2-8) itself has an effect of promoting kneading by applying shear to the rubber component. Moreover, in the production method of the eighth invention, since the coupling agent (D-8) represented by the chemical formula (1) is divisionally put, an initial reduction of the activity of the coupling agent is prevented and processability throughout the kneading operation can be maintained.

The added amount of the coupling agent (D-8) represented by the chemical formula (1) in the step X2-8 is preferably not less than 4 parts by mass, more preferably not less than 5 parts by mass, further preferably not less than 6 parts by mass based on 100 parts by mass of the added amount of the silica (B-8) in the step X2-8 since the reaction with a filler can be made sufficient and the effect of improving excellent processability of the coupling agent (D-8) can be brought out. On the other hand, the added amount of the coupling agent (D-8) represented by the chemical formula (1) in the step X2-8 is preferably not more than 20 parts by mass, more preferably not more than 10 parts by mass, further preferably not more than 9 parts by mass from the viewpoint of the effect of improving dispersibility of silica that is compatible with the increase of the cost.

The step in which the anti-aging agent (G-8) is added is not limited particularly, but from the viewpoint of operation efficiency and prevention of activity reduction of the anti-aging agent, it is preferable that all amount is added in the step X2-8.

The temperature at discharge of kneading in the step X1-8 and the step X2-8 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-8 and the step X2-8 is within the above range, the kneaded product in which silica (B-8) is well dispersed tends to be obtained efficiently.

The highest temperature during kneading in the step X1-8 and the step X2-8 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, by divisionally adding the coupling agent (D-8), a defect does not arise even if the kneading temperature becomes high and it is possible to promote the reaction of the coupling agent and promote the dispersion of the silica.

The kneading time in the step X1-8 and the step X2-8 is not limited particularly, but the kneading time in each step is preferably not less than 3.0 minutes, more preferably not less than 4.0 minutes, further preferably not less than 4.5 minutes since the kneaded product in which silica is well dispersed tends to be obtained efficiently. On the other hand, the kneading time in each step is preferably not more than 9 minutes, more preferably not more than 8 minutes, further preferably not more than 7 minutes.

In one embodiment of the eighth invention, it is preferable to keep the kneaded product at 150° C. to 190° C. for 10 to 120 seconds after the temperature reaches the highest temperature in the step X1-8 and/or the step X2-8 and the kneading is finished since the reaction between the coupling agent and the silica is completely performed.

Step F-8

In the step F-8, the kneaded product obtained in the step X2-8 is cooled and then the remaining amount of the vulcanizing agent (E-8) containing a vulcanizer and a vulcanization accelerator is added and the mixture is kneaded with an open roll and the like to obtain an unvulcanized rubber composition.

It is preferable that the kneaded product obtained in the step X2-8 is normally cooled to 100° C. or less, preferably to 20 to 80° C.

The temperature at discharge of kneading in the step F-8 is preferably not higher than 110° C., more preferably not higher than 100° C. If the temperature at discharge exceeds 110° C., rubber burning (scorching) tends to easily arise. On the other hand, the lower limit of the temperature at discharge of kneading in the step F-8 is not limited particularly, but is preferably not lower than 80° C.

The kneading time in the step F-8 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-8 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the eighth invention can be obtained successfully.

Rubber Composition for Tire

The rubber composition for tire according to the eighth invention can be used for any component of a tire and among these, can be suitably used for a tread or a sidewall since it is the rubber composition for tire in which processability, fuel efficiency and abrasion resistance are improved in a good balance.

Tire

In addition, a tire of the eighth invention can be produced with a normal method by use of the rubber composition for tire according to the eighth invention. That is, the rubber composition for tire produced by the production method of the eighth invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the eighth invention can be produced. It is noted that the tire of the eighth invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars.

<Ninth Invention>

The ninth invention is a production method of a rubber composition for tire comprising a rubber component comprising a butadiene rubber (A1-9) and an isoprene-based rubber (A2-9), silica (B-9), carbon black (C-9), a coupling agent (D-9) represented by the following chemical formula (1) and a vulcanizing agent (E-9) comprising a vulcanizer and a vulcanization accelerator, the method comprising:

(step X1-9) a step X1-9 of kneading A1-9, a part of B-9, a part of D-9 and optionally a part of E-9, (step X2-9) a step X2-9 of kneading the kneaded product of the step X1-9, A2-9, the remaining amount of B-9, the remaining amount of D-9 and optionally a part of E-9, and (step F-9) a step F-9 of kneading the kneaded product of the step X2-9 and the remaining amount of E-9.

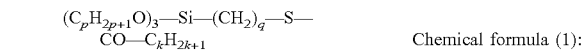
Chemical formula (1):

In the chemical formula (1), p represents an integer of 1 to 3, q represents an integer of 1 to 5, and k represents an integer of 5 to 12.

It is preferable that the butadiene rubber (A1-9) comprises a butadiene rubber which has a functional group that reacts with silica.

It is preferable that the nitrogen adsorption specific surface area of the silica is not less than 160 m$^2$/g and the total added amount of the silica is not less than 40 parts by mass based on 100 parts by mass of the rubber component.

It is preferable that the added amount of the coupling agent in each of the step X1-9 and the step X2-9 is 4 to 10 parts by mass based on 100 parts by mass of the silica added in each step.

It is preferable that the added amount of the silica in the step X1-9 is 10 to 90% by mass of the total added amount of silica.

It is preferable that the production method is a production method of the rubber composition further comprising a plasticizer and not less than 50% by mass of the total added amount of a plasticizer is kneaded in the step X1-9.

It is preferable that the highest temperature in the step X1-9 and/or the step X2-9 is 140° C. to 200° C.

It is preferable that after the kneading in the step X1-9 and/or the step X2-9 is finished, the production method comprises a step of keeping the kneaded product at 150 to 190° C. for 10 to 120 seconds.

It is preferable that a part or all amount of the vulcanization accelerator is kneaded in the step X1-9 and/or the step X2-9.

It is preferable that the production method is a production method of the rubber composition further comprising an anti-aging agent and an anti-aging agent is kneaded in the step X2-9.

It is preferable that the production method is a production method of the rubber composition further comprising a surfactant and a surfactant is kneaded in the step X1-9 and/or the step X2-9.

The ninth invention also relates to a tire having a tire component composed of the rubber composition for tire produced by the above production method of the rubber composition for tire.

According to the ninth invention, it is possible to produce a rubber composition for tire in which fuel efficiency, abrasion resistance and wet grip performance are improved in a good balance. Further, by use of a tire having a tire component composed of the produced rubber composition for tire, it is possible to produce a tire in which fuel efficiency, abrasion resistance and wet grip performance are improved in a good balance.

The rubber composition according to the ninth invention is characterized by comprising a rubber component comprising a butadiene rubber (A1-9) and an isoprene-based rubber (A2-9), silica (B-9), carbon black (C-9), a specified coupling agent (D-9), and a vulcanizing agent (E-9) comprising a vulcanizer and a vulcanization accelerator.

Rubber Component

The rubber component is characterized by comprising a butadiene rubber (A1-9) and an isoprene-based rubber (A2-9). By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The above rubber component comprises a butadiene rubber (BR) since it is excellent in abrasion resistance. In general, a rubber composition in which a white filler such as silica (B-9) is compounded in BR has a problem that dispersibility of the filler is low and it is difficult to obtain desired performance. However, in the ninth invention, the reaction between a filler and a rubber component is improved by divisionally kneading a specified coupling agent (D-9). Accordingly, dispersibility of a filler increases and fuel efficiency and abrasion resistance are improved as well as satisfactory processability can be obtained, thereby synergistically improving a balance among these performances.

Examples of the BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of the achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

The content of BR in the rubber component is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75%, further preferably not more than 70% by mass from the viewpoint of processability.

Examples of the isoprene-based rubber include a chemically synthesized polyisoprene rubber (IR), a natural rubber (NR), an epoxidized natural rubber (ENR) and the like. Among these, NR and ENR are preferable from the viewpoint of easy availability and the rubber strength.

In particular, the isoprene-based rubber or modified BR, due to a strong interaction of its functional groups, coagulates itself and dispersion of a filler usually becomes all the more difficult. However, in the ninth invention, by divisionally kneading a specified coupling agent (D-9), the coagulation of the rubber component is prevented and the reaction with silica is promoted.

The rubber component may comprise, in addition to the above BR and isoprene-based rubber, a styrene butadiene rubber (SBR), a styrene-isoprene-butadiene rubber (SIBR) and the like as necessary. If the rubber composition comprises a rubber component other than BR and an isoprene-based rubber, the rubber component is preferably added in the step X2-9 as described below.

Silica (B-9)

The silica (B-9) is not limited particularly and ones generally used in the tire industry can be used. Examples thereof include dry processed silica (silicic anhydride) and wet processed silica (hydrous silicic acid) and the like, and wet processed silica is preferable because it has more silanol groups.

The nitrogen adsorption specific surface area (N$_2$SA) of the silica (B-9) is preferably not less than 40 m$^2$/g, more preferably not less than 50 m$^2$/g, further preferably not less than 100 m$^2$/g, particularly preferably not less than 130 m$^2$/g, most preferably not less than 160 m$^2$/g from the viewpoint of breaking resistance. On the other hand, the N$_2$SA of the silica (B-9) is preferably not more than 500 m$^2$/g, more preferably not more than 300 m$^2$/g, further preferably not more than 250 m$^2$/g, particularly preferably not more than 200 m²/g from the viewpoint of fuel efficiency and processability. It is noted that the N₂SA of the silica (B-9) herein is a value as measured with the BET method in accordance with ATSM D3037-81.

The content (total added amount) of the silica (B-9) is preferably not less than 10 parts by mass, more preferably not less than 20 parts by mass, further preferably not less than 30 parts by mass, particularly preferably not less than 40 parts by mass based on 100 parts by mass of the rubber component (A-9) from the viewpoint of fuel efficiency, wet grip performance and on-ice performance. On the other hand, the total content of the silica (B-9) is preferably not more than 200 parts by mass, more preferably not more than 150 parts by mass, further preferably not more than 120 parts by mass from the viewpoint of dispersibility of a filler into the rubber component and processability.

Carbon Black (C-9)

The carbon black (C-9) is not limited particularly and ones generally used in the tire industry such as GPF, FEF, HAF, ISAF, SAF and the like can be used, and these carbon black may be used alone, or may be used in combination with two or more thereof.

The nitrogen adsorption specific surface area (N₂SA) of the carbon black (C-9) is preferably not less than 80 m²/g, more preferably not less than 100 m²/g from the viewpoint of weather resistance and antistatic performance. On the other hand, the N₂SA of the carbon black (C-9) is preferably not more than 200 m²/g, more preferably not more than 150 m²/g from the viewpoint of processability. It is noted that the N₂SA of the carbon black (C-9) herein is a value as measured in accordance with JIS K6217, method A.

The content (total added amount) of the carbon black (C-9) is preferably not less than 1 part by mass, more preferably not less than 3 parts by mass based on 100 parts by mass of the rubber component (A-9). If the content of the carbon black (C-9) is less than 1 part by mass, the effect obtained by inclusion of the carbon black may not be obtained sufficiently. On the other hand, the content of the carbon black (C-9) is preferably not more than 30 parts by mass, more preferably not more than 10 parts by mass from the viewpoint of fuel efficiency and processability.

Coupling Agent (D-9)

The specified coupling agent (D-9) is a compound represented by the following chemical formula (1).

Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D-9) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and cost. It is also possible that the coupling agent is used together with a general coupling agent other than the coupling agent (D-9) represented by the chemical formula (1).

The total content of the coupling agent (D-9) is preferably not less than 4 parts by mass, more preferably not less than 5 parts by mass, further preferably not less than 6 parts by mass based on 100 parts by mass of the total content of the silica from the viewpoint of the effect of improvement of a reaction with a filler and processability. On the other hand, the total content of the coupling agent (D-9) is preferably not more than 20 parts by mass, more preferably not more than 10 parts by mass, further preferably not more than 9 parts by mass from the viewpoint of the effect of improving dispersibility of silica that is compatible with the increase of the cost.

Vulcanizing Agent (E-9)

The vulcanizing agent (E-9) comprises a vulcanizer (E1-9) and a vulcanization accelerator (E2-9). Vulcanizing agents generally used in the rubber industry such as a vulcanization accelerator auxiliary agent can be also used.

Vulcanizer (E1-9)

The vulcanizer (E1-9) is not limited particularly and ones generally used in the tire industry can be used. Since the effect of the ninth invention can be successfully obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of the vulcanizer (E1-9) is preferably not less than 0.1 part by mass, more preferably not less than 0.5 part by mass based on 100 parts by mass of the rubber component (A-9). On the other hand, the content of the vulcanizer (E1-9) is preferably not more than 15 parts by mass, more preferably not more than 5 parts by mass. If the content of the vulcanizer (E1-9) is within the above range, satisfactory tensile strength, abrasion resistance and heat resistance can be obtained.

Vulcanization Accelerator (E2-9)

The vulcanization accelerator (E2-9) is not limited particularly and ones generally used in the tire industry can be used. Examples thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolsulfenamide, N-t-butyl-2-benzothiazolsulfenamide, N-oxyethylene-2-benzothiazolsulfenamide, and N,N'-diisopropyl-2-benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-9) is preferably not less than 0.1 part by mass, more preferably not less than 0.2 part by mass based on 100 parts by mass of the rubber component (A-9). On the other hand, the content of the vulcanization accelerator (E2-9) is preferably not more than 5 parts by mass, more preferably not more than 3 parts by mass. If the content of the vulcanization accelerator (E2-9) is within the above range, the reduction of the elastic modulus of rubber and the deterioration of breaking resistance can be prevented.

Other Compounding Agents

The rubber composition for tire of the ninth invention can suitably comprise, in addition to the above components, compounding agents that have been used in the rubber industry such as, for example, a plasticizer (F-9), a filler for reinforcement other than silica and carbon black, an anti-aging agent (G-9), an antioxidant, a stearic acid, wax and the like as necessary.

Plasticizer (F-9)

Since processability is improved and the strength of rubber is increased, it is preferable that the rubber composition for tire of the ninth invention comprises the plasticizer (F-9). The plasticizer (F-9) is not limited particularly and ones generally used in the tire industry can be used, and examples thereof include oil, liquid polymer, liquid resin and the like. Among these, oil is preferable since cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as the plasticizer (F-9), the content thereof based on 100 parts by mass of the rubber component (A-9) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-9)

The anti-aging agent (G-9) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises the anti-aging agent (G-9), the content thereof based on 100 parts by mass of the rubber component (A-9) is preferably not less than 0.5 part by mass, more preferably not less than 1.0 part by mass from the viewpoint of ozone resistance and crack resistance. On the other hand, the content of the anti-aging agent is preferably not more than 10 parts by mass, more preferably not more than 5 parts by mass from the viewpoint of prevention of discoloration.

Surfactant

In an embodiment of the ninth invention, it is preferable that the rubber composition further comprises a surfactant. By inclusion of a surfactant, dispersibility of the above fillers comprising silica and carbon black is improved and a discoloration of the obtained rubber composition for tire due to deterioration over time can be prevented.

Examples of the surfactant include metallic soap such as an organic acid of a metallic salt, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of the surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-9) from the viewpoint of the effect of improving dispersibility of silica. On the other hand, the content of the surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

Production Method of Rubber Composition for Tire

The production method of a rubber composition for tire of the ninth invention is characterized by dividing a kneading step into a step X1-9, a step X2-9 and a step F-9. Known kneaders can be used in each step and examples thereof include a Banbury mixer, a kneader, an open roll and the like.

Specifically, the production method of a rubber composition for tire includes a kneading process comprising a step X1-9 of kneading A1-9, a part of B-9, a part of D and optionally a part of E-9, a step X2-9 of kneading the kneaded product of the step X1-9, A2-9, the remaining amount of B-9, the remaining amount of D-9 and optionally a part of E-9, and a step F-9 of kneading the kneaded product of the step X2-9 and the remaining amount of E-9, to obtain an unvulcanized rubber composition. The obtained unvulcanized rubber composition is then vulcanized (vulcanization process) and the rubber composition for tire according to the ninth invention can be produced. It is noted that the timing when other compounding agents such as carbon black (C-9), a plasticizer (F-9), an anti-aging agent (G-9), a zinc oxide, a stearic acid and the like are added and kneaded is not limited particularly, and these compounding agents may be added in any of the step X1-9, the step X2-9 or the step F-9, or may be added divisionally.

Particularly, the production method of the ninth invention is characterized in that the coupling agent (D-9) represented by the chemical formula (1) is divisionally kneaded. The coupling agent (D9) can form homogeneous chemical bonds between the filler and the polymer without losing activity even in the kneading in the prior input as in the ninth invention because the coupling agent does not have a plurality of alkoxysilyl groups in the molecule and the coagulation thereof is small and also because a mercapto group suitably reacting with a polymer part becomes a fatty acid thioester, thereby non-uniformity resulting from a rapid reaction is prevented.

Step X1-9

In the step X1-9, compounding agents comprising a butadiene rubber (A1-9), a part of silica (B-9), a part of the coupling agent (D-9) and optionally a part of the vulcanizing agent (E-9) are kneaded with a Banbury mixer and the like. From this step, the filler disperses while forming a strong bond with a rubber component, particularly with a rubber component having high affinity with the filler. Further, by use of a coupling agent (D-9) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane is used, then it releases sulfur even in this phase, thereby processability is deteriorated, dispersion of the filler is prevented and the activity of a coupling agent itself is lowered. The coupling agent (D-9) represented by the chemical formula (1) does not release sulfur, thereby being able to continue kneading while maintaining processability according to the production method of the ninth invention.

In the rubber composition comprising BR and SBR as a rubber component, the silica tends to be localized in the SBR. However, in the production method of the ninth invention, by previously kneading the BR, silica and a specified coupling agent in the step X1-9, the silica is allowed to also exist in the BR well and a rubber composition which is more excellent in abrasion resistance, wet grip performance and on-ice performance can be produced.

The added amount of the silica (B-9) in the step X1-9 is preferably not less than 10% by mass, more preferably not less than 30% by mass, further preferably not less than 40% by mass, further preferably not less than 50% by mass of the total added amount of the silica (B-9) from the viewpoint of improvement of the effect of kneading silica, sufficient dispersion of silica and abrasion resistance. On the other hand, the added amount of the silica (B-9) in the step X1-9 is preferably not more than 95% by mass, more preferably not more than 90% by mass, further preferably not more than 85% by mass of the total added amount of the silica (B-9) from the viewpoint of the effect of adding the silica divisionally in the step X2-9 as described below, fuel efficiency and abrasion resistance.

The added amount of the coupling agent (D-9) represented by the chemical formula (1) in the step X1-9 is preferably not less than 4 parts by mass, more preferably not less than 5 parts by mass, further preferably not less than 6 parts by mass based on 100 parts by mass of the added amount of the silica (B-9) in the step X1-9, since a reaction with the filler becomes sufficient and the excellent effect of improving processability of the coupling agent (D-9) can be exerted. On the other hand, the added amount of the coupling agent (D-9) represented by the chemical formula (1) in the step X1-9 is preferably not more than 20 parts by mass, more preferably not more than 10 parts by mass, further preferably not more than 9 parts by mass from the viewpoint of the effect of improving dispersibility of silica that is compatible with the increase of cost.

It is preferable that the carbon black (C-9) is added in the step X1-9 and/or the step X2-9. The added amount of the carbon black (C-9) in the step X1-9 is preferably not less than 10% by mass, more preferably not less than 50% by mass, further preferably not less than 80% by mass, most preferably 100% by mass of the total added amount of the carbon black (C-9) from the viewpoint of the improvement of dispersibility of carbon black and efficiency of the step. If the added amount of the carbon black (C-9) in the step X1-9 is less than 100% by mass, it is preferable that the remaining amount is added in the step X2-9.

While the step in which the plasticizer (F-9) is added is not limited particularly, it is preferable that not less than 50% by mass, more preferably not less than 70% by mass, further preferably not less than 80% by mass of the total added amount of the plasticizer (F-9) is added in the step X1-9. If the added amount of the plasticizer (F-9) in the step X1-9 is less than 100% by mass, it is preferable that the remaining amount is added in the step X2-9 since dispersibility of the silica which is added in the step X2-9 is more improved.

It is preferable that the surfactant is added in the step X1-9 and/or the step X2-9 from the viewpoint of promoting the effect of dispersing silica, and is preferably added in the step X1-9 since the effect of dispersing silica is more promoted and a gelation of the coupling agent can be prevented.

Step X2-9

In the step X2-9, the compounding agents comprising an isoprene-based rubber (A2-9), the remaining amount of the silica (B-9), the remaining amount of the coupling agent (D-9) and optionally a part of the vulcanizing agent (E-9) are added to the kneaded product of the step X1-9 and the mixture is kneaded. If the all amount of the silica is input in the step X1-9, the silica tends to be localized within the isoprene-based rubber and/or an interface portion of the isoprene-based rubber, however, in the production method of the ninth invention, since the silica is respectively input divisionally in the step X1-9 and the step X2-9, the silica becomes easily dispersed through the entire rubber component. Further, the later added silica (input in the step X2-9) itself has an effect of promoting kneading by applying shear to the rubber component. Moreover, in the production method of the ninth invention, since the coupling agent (D-9) represented by the chemical formula (1) is divisionally added, an initial reduction of the activity of the coupling agent is prevented and processability throughout the kneading operation can be maintained.

The added amount of the coupling agent (D-9) in the step X2-9 is preferably not less than 4 parts by mass, more preferably not less than 5 parts by mass, further preferably not less than 6 parts by mass based on 100 parts by mass of the added amount of the silica (B-9) in the step X2-9 since the reaction with a filler can be made sufficient and the effect of improving excellent processability of the coupling agent (D-9) can be brought out. On the other hand, the added amount of the coupling agent (D-9) represented by the chemical formula (1) in the step X2-9 is preferably not more than 20 parts by mass, more preferably not more than 10 parts by mass, further preferably not more than 9 parts by mass from the viewpoint of the effect of improving dispersibility of silica that is compatible with the increase of cost.

The step in which the anti-aging agent (G-9) is added is not limited particularly, but from the viewpoint of operation efficiency and prevention of activity reduction of the anti-aging agent, it is preferable that all amount is added in the step X2-9.

The temperature at discharge of kneading in the step X1-9 and the step X2-9 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-9 and the step X2-9 is within the above range, the kneaded product in which silica (B-9) is well dispersed tends to be obtained efficiently.

The highest temperature during kneading in the step X1-9 in the step X2-9 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, by divisionally adding the coupling agent (D-9), a defect does not arise even if the kneading temperature becomes high and it is possible to promote the reaction of the coupling agent and promote the dispersion of the silica.

The kneading time in the step X1-9 and the step X2-9 is not limited particularly, but the kneading time in each step is preferably not less than 3.0 minutes, more preferably not less than 4.0 minutes, further preferably not less than 4.5 minutes since the kneaded product in which silica is well dispersed tends to be obtained efficiently. On the other hand, the kneading time in each step is preferably not more than 9 minutes, more preferably not more than 8 minutes, further preferably not more than 7 minutes.

In one embodiment of the ninth invention, it is preferable to keep the kneaded product at 150° C. to 190° C. for 10 to 120 seconds after the temperature reaches the highest temperature in the step X1-9 and/or the step X2-9 and the kneading is finished since the reaction between the coupling agent and the silica is completely performed.

Step F

In the step F-9, the kneaded product obtained in the step X2-9 is cooled and then the vulcanizing agent (E-9) containing the vulcanizer and the vulcanization accelerator is added and the mixture is kneaded with an open roll and the like to obtain an unvulcanized rubber composition.

While the vulcanizing agent may be added in the step F-9 at a time, it is preferable that a part or all amount is added in the step X1-9 and/or the step X2-9 and then the remaining amount is added in the step F-9. By adding a part or all amount in the step X1-9 and/or the step X2-9, dispersion between the silica and the rubber component can be promoted. It is more preferable that a part or all amount of the guanidine vulcanization accelerator is added in the step X1-9 and/or the step X2-9 since dispersibility of the silica can be more promoted.

It is preferable that the kneaded product obtained in the step X2-9 is normally cooled to 100° C. or less, preferably to 20 to 80° C.

The temperature at discharge of kneading in the step F-9 is preferably not higher than 110° C., more preferably not higher than 100° C. If the temperature at discharge exceeds 110° C., a rubber burning (scorch) tends to easily arise. On the other hand, the lower limit of the temperature at discharge of kneading in the step F-9 is not limited particularly, but is preferably not lower than 80° C.

The kneading time in the step F-9 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-9 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the ninth invention can be obtained successfully.

Rubber Composition for Tire

The rubber composition for tire according to the ninth invention can be used for any component of a tire and among these, can be suitably used for a tread or a sidewall since it is the rubber composition for tire in which processability, fuel efficiency and abrasion resistance are improved in a good balance.

Tire

In addition, a tire of the ninth invention can be produced with a normal method by use of the rubber composition for tire according to the ninth invention. That is, the rubber composition for tire produced by the production method of the ninth invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the ninth invention can be produced. It is noted that the tire of the ninth invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars.

<Tenth Invention>

The tenth invention is a production method of a rubber composition for tire comprising a rubber component (A-10) comprising at least one selected from the group consisting of a natural rubber and a synthetic diene rubber, silica (B-10), carbon black 1 (C1-10) having a nitrogen specific surface area of not more than 200 m²/g, carbon black 2 (C2-10) having a nitrogen specific surface area of not less than 900 m²/g, a coupling agent (D-10) represented by the following chemical formula (1), and a vulcanizing agent (E-10) comprising a vulcanizer and a vulcanization accelerator, the method comprising:
(step X1-10) a step X1-10 of kneading A-10, a part or all amount of B-10, C1-10, a part of D-10 and optionally a part of E-10,
(step X2-10) a step X2-10 of kneading the kneaded product of the step X1-10, the remaining amount of B-10, C2-10, the remaining amount of D-10 and optionally a part of E-10, and
(step F-10) a step F-10 of kneading the kneaded product of the step X2-10 and the remaining amount of E-10.

Chemical formula (1):

In the chemical formula (1), p represents an integer of 1 to 3, q represents an integer of 1 to 5, and k represents an integer of 5 to 12.

It is preferable that the rubber component comprises a styrene butadiene rubber and/or a butadiene rubber which has a functional group that reacts with silica.

It is preferable that the DBP oil absorption amount of the carbon black 2 (C2-10) is not less than 300 ml/100 g.

It is preferable that the volume specific resistivity of the rubber composition is less than $1.0 \times 10^7$ Ω·cm.

It is preferable that the added amount of silica in the step X1-10 is 50 to 95% by mass of the total added amount of silica.

It is preferable that the production method is a production method of the rubber composition further comprising a plasticizer and not less than 50% by mass of the total added amount of a plasticizer is kneaded in the step X1-10.

It is preferable that the highest temperature in the step X1-10 and/or the step X2-10 is 140° C. to 200° C.

It is preferable that after the kneading in the step X1-10 and/or the step X2-10 is finished, the production method comprises a step of keeping the kneaded product at 150 to 190° C. for 10 to 120 seconds.

It is preferable that a part or all amount of the vulcanization accelerator is kneaded in the step X1-10 and/or the step X2-10.

It is preferable that the production method is a production method of the rubber composition further comprising an anti-aging agent and an anti-aging agent is kneaded in the step X2-10.

It is preferable that the production method is a production method of the rubber composition further comprising a surfactant and a surfactant is kneaded in the step X1-10 and/or the step X2-10.

The tenth invention also relates to a tire having a tire component composed of the rubber composition for tire produced by the above production method of the rubber composition for tire.

According to the tenth invention, it is possible to produce a rubber composition for tire in which fuel efficiency, abrasion resistance, wet grip performance and electrical conductivity are improved in a good balance. Further, by use of a tire having a tire component composed of the produced rubber composition for tire, it is possible to produce a tire in which fuel efficiency, abrasion resistance, wet grip performance and electrical conductivity are improved in a good balance.

The rubber composition according to the invention is characterized by comprising a specified rubber component (A-10), silica (B-10), carbon black 1 (C1-10) and carbon black 2 (C2-10) respectively having a specified nitrogen adsorption specific surface area, a specified coupling agent (D-10), and a vulcanizing agent (E-10) comprising a vulcanizer and a vulcanization accelerator.

Rubber Component (A-10)

The rubber component (A-10) is characterized by comprising at least one selected from the group consisting of a natural rubber and a synthetic diene rubber, preferably comprising two or more thereof. By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The natural rubber includes a natural rubber (NR), and a modified natural rubber such as an epoxidized natural rubber (ENR), a hydrogenated natural rubber (HNR), a deproteinized natural rubber (DPNR), a high purity natural rubber (HPNR) and the like.

The NR is not limited particularly and those generally used in the tire industry such as SIR20, RSS#3, TSR20 and the like can be used.

In the case where the rubber composition comprises NR, the content thereof in the rubber component (A-10) is preferably not less than 5% by mass, more preferably not less than 10% by mass since breaking resistance of the rubber composition improves. On the other hand, the content of NR is preferably not more than 80% by mass, more preferably not more than 70% by mass, further preferably not more than 50% by mass since fuel efficiency and abrasion resistance of the rubber composition are excellent.

Examples of the synthetic diene rubber include an isoprene rubber (IR), a styrene butadiene rubber (SBR), a butadiene rubber (BR), a styrene-isoprene-butadiene rubber (SIBR) and the like.

Among synthetic diene rubbers, it is preferable that the rubber composition comprises SBR since it is excellent in processability, dry grip performance and wet grip performance. The SBR is not limited particularly and examples thereof include an unmodified solution-polymerized styrene-butadiene rubber (S-SBR), an unmodified emulsion-polymerized styrene-butadiene rubber (E-SBR), and modified SBRs of these (modified E-SBR, modified S-SBR) and the like. Examples of the modified SBR include a modified SBR in which a terminal and/or a main chain is modified, a modified SBR coupled by a tin or silicon compound (such as a condensate or one having a branched structure) and the like. Among these SBRs, S-SBR and modified S-SBR are preferable since they can improve grip performance and abrasion resistance in a good balance, and from the viewpoint of a reaction with silica, a modified SBR having at least one selected from the group consisting of a silyl group, an amino group, an amide group, a hydroxyl group and an epoxy group is particularly preferable. While these SBRs can be used alone, a use of SBRs having different physical properties such as a content of styrene is also possible depending on its application. It is noted that SBRs may be appropriately selected depending on a part to which they are applied.

The styrene content of SBR is preferably not less than 5% by mass, more preferably not less than 10% by mass, further preferably not less than 20% by mass from the viewpoint of dry grip performance, wet grip performance and rubber strength. On the other hand, the styrene content of SBR is preferably not more than 60% by mass, more preferably not more than 50% by mass, further preferably not more than 40% by mass from the viewpoint of fuel efficiency. It is noted that the styrene content of SBR herein is calculated from a $^1$H-NMR measurement.

The vinyl bond amount of SBR is preferably not less than 10 mol %, more preferably not less than 15 mol %, further preferably not less than 20 mol % from the viewpoint of dry grip performance, wet grip performance and rubber strength. On the other hand, the vinyl bond amount of SBR is preferably not more than 65 mol %, more preferably not more than 60 mol %, further preferably not more than 30 mol % from the viewpoint of fuel efficiency. It is noted that the vinyl bond amount of SBR herein refers to a vinyl bond amount of a butadiene part and is calculated from a $^1$H-NMR measurement.

In the case where the rubber composition comprises SBR, the content thereof in the rubber component (A-10) is preferably not less than 10% by mass, more preferably not less than 20% by mass, further preferably not less than 30% by mass from the viewpoint of dry grip performance and wet grip performance. On the other hand, the content of SBR is preferably not more than 90% by mass, more preferably not more than 80% by mass from the viewpoint of abrasion resistance.

Further, it is preferable that the rubber component comprises BR since it is excellent in abrasion resistance. In general, a rubber composition in which a white filler such as silica (B-10) is compounded in BR has a problem that dispersibility of the filler is low and it is difficult to obtain desired performance. However, in the tenth invention, the reaction between a filler and a rubber component is improved by divisionally kneading a specified coupling agent (D-10). Accordingly, dispersibility of a filler increases and fuel efficiency and abrasion resistance are improved as well as satisfactory processability can be obtained, thereby synergistically improving a balance among these performances.

Examples of the BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

In the case where the rubber composition comprises BR, the content thereof in the rubber component (A-10) is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75% by mass, further preferably not more than 70% by mass from the viewpoint of processability.

In particular, the modified SBR or modified BR, due to a strong interaction of its functional groups, coagulates itself and dispersion of a filler usually becomes all the more difficult. However, in the tenth invention, by divisionally kneading a specified coupling agent (D-10), the coagulation of the rubber component is prevented and the reaction with silica is promoted.

Silica (B-10)

The silica (B-10) is not limited particularly and ones generally used in the tire industry can be used. Examples thereof include dry processed silica (silicic anhydride) and wet processed silica (hydrous silicic acid) and the like, and wet processed silica is preferable because it has more silanol groups.

The nitrogen adsorption specific surface area ($N_2SA$) of the silica (B-10) is preferably not less than 40 $m^2/g$, more preferably not less than 50 $m^2/g$, further preferably not less than 100 $m^2/g$, particularly preferably not less than 130 $m^2/g$, most preferably not less than 160 $m^2/g$ from the viewpoint of breaking strength. On the other hand, the $N_2SA$ of the silica (B-10) is preferably not more than 500 $m^2/g$, more preferably not more than 300 $m^2/g$, further preferably not more than 250 $m^2/g$, particularly preferably not more than 200 $m^2/g$ from the viewpoint of fuel efficiency and processability. It is noted that the $N_2SA$ of the silica (B-10) herein is a value as measured with the BET method in accordance with ATSM D3037-81.

The content (total added amount) of the silica (B-10) is preferably not less than 10 parts by mass, more preferably not less than 20 parts by mass, further preferably not less than 30 parts by mass, particularly preferably not less than 40 parts by mass based on 100 parts by mass of the rubber component (A-10) from the viewpoint of fuel efficiency and wet grip performance. On the other hand, the total content of the silica (B-10) is preferably not more than 200 parts by mass, more preferably not more than 150 parts by mass, further preferably not more than 120 parts by mass from the viewpoint of dispersibility of a filler into the rubber component and processability.

Carbon Black

The rubber composition for tire according to the tenth invention is characterized by comprising carbon black 1 (C1-10) having a nitrogen adsorption specific surface area ($N_2SA$) of not more than 200 $m^2/g$ and carbon black 2 (C2-10) having a $N_2SA$ of not less than 900 $m^2/g$ as carbon black. By the combined use of the carbon black 1 and the carbon black 2, fuel efficiency, abrasion resistance, wet grip performance and electrical conductivity can be improved in a good balance. It is noted that carbon black other than the carbon black 1 (C1-10) and the carbon black (C2-10) may be also used in combination.

The carbon black 1 (C1-10) is not limited particularly as long as it has a nitrogen adsorption specific surface area ($N_2SA$) of not more than 200 $m^2/g$ and ones generally used in the tire industry such as GPF, FEF, HAF, ISAF, SAF and the like can be used, and these carbon black may be used alone, or may be used in combination with two or more thereof.

The nitrogen adsorption specific surface area ($N_2SA$) of the carbon black 1 (C1-10) is preferably not less than 80 m$^2$/g, more preferably not less than 100 m$^2$/g from the viewpoint of weather resistance and electrical conductivity. On the other hand, the $N_2SA$ of the carbon black 1 (C1-10) is not more than 200 m$^2$/g, preferably not more than 150 m$^2$/g. If the $N_2SA$ of the carbon black 1 (C1-10) exceeds 200 m$^2$/g, processability tends to deteriorate. It is noted that the $N_2SA$ of the carbon black herein is a value as measured in accordance with JIS K6217, method A.

The dibutyl phthalate (DBP) oil adsorption amount of the carbon black 1 (C1-10) is preferably not less than 60 ml/100 g, more preferably not less than 70 ml/100 g from the viewpoint of reinforcing property and braking resistance. On the other hand, the dibutyl phthalate (DBP) oil adsorption amount of the carbon black 1 (C1-10) is preferably not more than 130 ml/100 g, more preferably not more than 120 ml/100 g from the viewpoint of the tensile elongation at break, braking resistance and durability. It is noted that the DBP oil adsorption amount herein is a value calculated from a measurement method of JIS K6217-4.

The content of the carbon black 1 (C1-10) is preferably not less than 1 part by mass, more preferably not less than 5 parts by mass, further preferably not less than 8 parts by mass based on 100 parts by mass of the rubber component (A-10) from the viewpoint of the effect obtained by inclusion of the carbon black. On the other hand, the content of the carbon black 1 (C1-10) is preferably not more than 30 parts by mass, more preferably not more than 20 parts by mass from the viewpoint of fuel efficiency.

The carbon black 2 (C2-10) is what is called electrically conductive carbon black and according to the production method of the rubber composition of the tenth invention which comprises the carbon black 2 (C2-10), it is possible to easily improve fuel efficiency and electrical conductivity in a good balance.

The nitrogen adsorption specific surface area ($N_2SA$) of the carbon black 2 (C2-10) is not less than 900 m$^2$/g, preferably not less than 1,000 m$^2$/g, more preferably not less than 1,050 m$^2$/g. If the $N_2SA$ is less than 900 m$^2$/g, sufficient electrical conductivity tends not to be obtained. On the other hand, the $N_2SA$ of the carbon black 2 (C2-10) is preferably not more than 1,200 m$^2$/g, more preferably not more than 1,150 m$^2$/g, further preferably not more than 1,100 m$^2$/g from the viewpoint of fuel efficiency, dispersibility, breaking resistance and durability.

The DBP oil adsorption amount of the carbon black 2 (C2-10) is preferably not less than 300 ml/100 g, more preferably not less than 350 ml/100 g from the viewpoint of electrical conductivity. On the other hand, the DBP oil adsorption amount of the carbon black 2 (C2-10) is preferably not more than 600 ml/100 g, more preferably not more than 500 ml/100 g, further preferably not more than 450 ml/100 g from the viewpoint of braking resistance and durability.

Examples of a suitable commercially available product of carbon black 2 (C2-10) include LIONITE ($N_2SA$: 1,052 m$^2$/g, DBP: 378 ml/100 g) manufactured by Lion Corporation, KETJENBLACK EC300J ($N_2SA$: 800 m$^2$/g, DBP: 365 ml/100 g), PRINTEX XE2B ($N_2SA$: 1,000 m$^2$/g, DBP: 420 ml/100 g) manufactured by Evonik Industries and the like.

The content of the carbon black 2 (C2-10) is preferably not less than 0.5 part by mass, more preferably not less than 1.0 part by mass, further preferably not less than 2.0 parts by mass based on 100 parts by mass of the rubber component 7 (A-10) from the viewpoint of electrical conductivity. On the other hand, the content of the carbon black 2 (C2-10) is preferably not more than 20 parts by mass, more preferably not more than 15 parts by mass from the viewpoint of fuel efficiency and the cost.

Coupling Agent (D-10)

The coupling agent (D-10) is a compound represented by the following chemical formula (1).

Chemical formula (1):
$$(C_pH_{2p+1}O)_3-Si-(CH_2)_q-S-CO-C_kH_{2k+1}$$

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D-10) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and cost. It is also possible that the coupling agent is used together with a general coupling agent other than the coupling agent (D-10) represented by the chemical formula (1).

The total content of the coupling agent (D-10) is preferably not less than 4 parts by mass, more preferably not less than 5 parts by mass, further preferably not less than 6 parts by mass based on 100 parts by mass of the total content of the silica from the viewpoint of the effect of improvement of a reaction with a filler and processability. On the other hand, the total content of the coupling agent (D-10) is preferably not more than 20 parts by mass, more preferably not more than 10 parts by mass, further preferably not more than 9 parts by mass from the viewpoint of the effect of improving dispersibility of silica that is compatible with the increase of the cost.

Vulcanizing Agent (E-10)

The vulcanizing agent (E-10) comprises a vulcanizer (E1-10) and a vulcanization accelerator (E2-10). Vulcanizing agents generally used in the rubber industry such as a vulcanization accelerator auxiliary agent can be also used.

Vulcanizer (E1-10)

The vulcanizer (E1-10) is not limited particularly and ones generally used in the tire industry can be used. Since the effect of the tenth invention can be successfully obtained, sulfur is preferable and powder sulfur is more preferable. Sulfur can be used in combination with other vulcanizers.

Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as a dicumyl peroxide and the like.

The content of the vulcanizer (E1-10) is preferably not less than 0.1 part by mass, more preferably not less than 0.5 part by mass based on 100 parts by mass of the rubber component (A-10). On the other hand, the content of the vulcanizer (E1-10) is preferably not more than 15 parts by mass, more preferably not more than 5 parts by mass. If the content of the vulcanizer (E1-10) is within the above range, satisfactory tensile strength, abrasion resistance and heat resistance can be obtained.

Vulcanization Accelerator (E2-10)

The vulcanization accelerator (E2-10) is not limited particularly and ones generally used in the tire industry can be used. Examples thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolsulfenamide, N-t-butyl-2-benzothiazolsulfenamide, N-oxyethylene-2-benzothiazolsulfenamide, and N,N'-diisopropyl-2-benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-10) is preferably not less than 0.1 part by mass, more preferably not less than 0.2 part by mass based on 100 parts by mass of the rubber component (A-10). On the other hand, the content of the vulcanization accelerator (E2-10) is preferably not more than 5 parts by mass, more preferably not more than 3 parts by mass. If the content of the vulcanization accelerator (E2-10) is within the above range, the reduction of the elastic modulus of rubber and the deterioration of breaking resistance can be prevented.

Other Compounding Agents

The rubber composition for tire of the tenth invention can suitably comprise, in addition to the above components, compounding agents that have been used in the rubber industry such as, for example, a plasticizer (F-10), a filler for reinforcement other than silica and carbon black, an anti-aging agent (G-10), an antioxidant, a stearic acid, wax and the like as necessary.

Plasticizer (F-10)

Since processability is improved and the strength of rubber is increased, it is preferable that the rubber composition for tire of the tenth invention comprises the plasticizer (F-10). The plasticizer (F-10) is not limited particularly and ones generally used in the tire industry can be used, and examples thereof include oil, liquid polymer, liquid resin and the like. Among these, oil is preferable since cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as the plasticizer (F-10), the content thereof based on 100 parts by mass of the rubber component (A-10) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-10)

The anti-aging agent (G-10) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises the anti-aging agent (G-10), the content thereof based on 100 parts by mass of the rubber component (A-10) is preferably not less than 0.5 part by mass, more preferably not less than 1.0 part by mass from the viewpoint of ozone resistance and crack resistance. On the other hand, the content of the anti-aging agent is preferably not more than 10 parts by mass, more preferably not more than 5 parts by mass from the viewpoint of prevention of discoloration.

Surfactant

In an embodiment of the tenth invention, it is preferable that the rubber composition further comprises a surfactant. By inclusion of a surfactant, dispersibility of the above fillers comprising silica and carbon black is improved and a discoloration of the obtained rubber composition for tire due to deterioration over time can be prevented.

Examples of the surfactant include metallic soap such as an organic acid of a metallic salt, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of the surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-10) from the viewpoint of the effect of improving dispersibility of silica. On the other hand, the content of the surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

It is preferable that the volume specific resistivity of the rubber composition according to the tenth invention is less than $1.0 \times 10^7$ Ω·cm, more preferably not more than $1.0 \times 10^6$ Ω·cm since electrical conductivity can be obtained and a noise or spark due to static electricity can be prevented. It is noted that the volume specific resistivity herein is a value calculated by a measurement method of JIS K6271.

Production Method of Rubber Composition for Tire

The production method of a rubber composition for tire of the tenth invention is characterized by dividing a kneading step into a step X1-10, a step X2-10 and a step F-10. Known kneaders can be used in each step and examples thereof include a Banbury mixer, a kneader, an open roll and the like.

Specifically, the production method of a rubber composition for tire includes a kneading process comprising a step X1-10 of kneading A-10, a part or all amount of B-10, C1-10, a part of D-10 and optionally a part of E-10, a step X2-10 of kneading the kneaded product of the step X1-10, the remaining amount of B-10, C2-10, the remaining amount of D-10 and optionally a part of E-10, and a step F-10 of kneading the kneaded product of the step X2-10 and the remaining amount of E-10, to obtain an unvulcanized rubber composition. The obtained unvulcanized rubber composition is then vulcanized (vulcanization process) and the rubber composition for tire according to the tenth invention can be produced. It is noted that the timing when other compounding agents such as a plasticizer (F-10), an anti-aging agent (G-10), a zinc oxide, a stearic acid and the like are added and kneaded is not limited particularly, and these compounding agents may be added in any of the step X1-10, the step X2-10 or the step F-10, or may be added divisionally.

Additionally, the production method of the tenth invention is characterized in that the coupling agent (D-10) represented by the chemical formula (1) is divisionally kneaded. The coupling agent (D-10) can form homogeneous chemical bonds between the filler and the polymer without losing activity even in the kneading in the prior input as in the tenth invention because the coupling agent does not have a plurality of alkoxysilyl groups in the molecule and the coagulation thereof is small and also because a mercapto group suitably reacting with a polymer part becomes a fatty acid thioester, thereby non-uniformity resulting from a rapid reaction is prevented.

Step X1-10

In the step X1-10, compounding agents comprising all amount of the rubber component (A-10), a part or all amount of silica (B-10), carbon black 1 (C1-10), a part of the coupling agent (D-10) and optionally a part of the vulcanizing agent (E-10) are kneaded with a Banbury mixer and the like. From this step, the filler disperses while forming a strong bond with a rubber component, particularly with a rubber component having high affinity with the filler. Further, by use of a coupling agent (D-10) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane is used, then it releases sulfur even in this phase, thereby processability is deteriorated, dispersion of the filler is prevented and the activity of a coupling agent itself is lowered. The coupling agent (D-10) represented by the chemical formula (1) does not release sulfur, thereby being able to continue kneading while maintaining processability according to the production method of the tenth invention.

The added amount of the silica (B-10) in the step X1-10 is preferably not less than 50% by mass, more preferably not less than 60% by mass, further preferably not less than 70% by mass, even further preferably not less than 80% by mass of the total added amount of the silica (B-10) from the viewpoint of improvement of the effect of kneading silica, sufficient dispersion of silica and abrasion resistance. While all amount of the silica (B-10) may be added in the step X1-10, from the viewpoint of the effect of adding the silica divisionally in the step X2-10 as described below, fuel efficiency and abrasion resistance, the added amount is preferably not more than 95% by mass, more preferably not more than 90% by mass of the total added amount of the silica (B-10).

The added amount of the coupling agent (D-10) represented by the chemical formula (1) in the step X1-10 is preferably not less than 4 parts by mass, more preferably not less than 5 parts by mass, further preferably not less than 6 parts by mass based on 100 parts by mass of the added amount of the silica (B-10) in the step X1-10, since a reaction with the filler becomes sufficient and the excellent effect of improving processability of the coupling agent (D-10) can be exerted. On the other hand, the added amount of the coupling agent (D-10) represented by the chemical formula (1) in the step X1-10 is preferably not more than 20 parts by mass, more preferably not more than 10 parts by mass, further preferably not more than 9 parts by mass from the viewpoint of the effect of improving dispersibility of silica that is compatible with the increase of the cost.

While the step in which the plasticizer (F-10) is added is not limited particularly, it is preferable that not less than 50% by mass, more preferably not less than 70% by mass, further preferably not less than 80% by mass of the total added amount of the plasticizer (F-10) is added in the step X1-10. If the added amount of the plasticizer (F-10) in the step X1-10 is less than 100% by mass, it is preferable that the remaining amount is added in the step X2-10 since dispersibility of the silica which is added in the step X2-10 is more improved.

It is preferable that the surfactant is added in the step X1-10 and/or the step X2-10 from the viewpoint of promoting the effect of dispersing silica, and is preferably added in the step X1-10 since the effect of dispersing silica is more promoted and a gelation of the coupling agent can be prevented.

Step X2-10

In the step X2-10, the compounding agents comprising the remaining amount of the silica (B-10), carbon black 2 (C2-10), the remaining amount of the coupling agent (D-10) and optionally a part of the vulcanizing agent (E-10) are added to the kneaded product of the step X1-10 and the mixture is kneaded. If the carbon black 1 (C1-10) and the carbon black 2 (C2-10) are kneaded at the same time, there is a tendency that a kneading shear is excessively applied to the carbon black 2 and the network of electrically conductive carbon black is broken, thereby making electric conductivity and abrasion resistance insufficient. However, by adding the carbon black 2 (C2-10) after adding the carbon black 1 (C1-10), that is, by adding the carbon black 2 (C2-10) in the step X2-10, the dispersion of the carbon black 2 does not become excess and a suitable network can be formed. Moreover, in the production method of the tenth invention, since the coupling agent (D-10) represented by the chemical formula (1) is divisionally input, an initial reduction of the activity of the coupling agent is prevented and processability throughout the kneading operation can be maintained.

The added amount of the coupling agent (D-10) represented by the chemical formula (1) in the step X2-10 is preferably not less than 4 parts by mass, more preferably not less than 5 parts by mass, further preferably not less than 6 parts by mass based on 100 parts by mass of the added amount of the silica (B-10) in the step X2-10 since the reaction with a filler can be made sufficient and the effect of improving excellent processability of the coupling agent (D-10) can be brought out. On the other hand, the added amount of the coupling agent (D-10) represented by the chemical formula (1) in the step X2-10 is preferably not more than 20 parts by mass, more preferably not more than 10 parts by mass, further preferably not more than 9 parts by mass from the viewpoint of the effect of improving dispersibility of silica that is compatible with the increase of cost. It is noted that if all amount of the silica (B-10) is added in the step X1-10, then a part of the coupling agent (D-10) may be added in the step X1-10 instead of all amount thereof being added and the remaining amount may be added in the step X2-10.

The step in which the anti-aging agent (G-10) is added is not limited particularly, but from the viewpoint of operation efficiency and prevention of activity reduction of the anti-aging agent, it is preferable that all amount is added in the step X2-10.

The temperature at discharge of kneading in the step X1-10 and the step X2-10 is not limited particularly, but is preferably not lower than 142° C., more preferably not lower than 146° C., further preferably not lower than 148° C. On the other hand, the temperature at discharge is preferably not higher than 170° C., more preferably not higher than 160° C. If the temperature at discharge in the step X1-10 and the step X2-10 is within the above range, the kneaded product in which silica (B-10) is well dispersed tends to be obtained efficiently.

The highest temperature during kneading in the step X1-10 and the step X2-10 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, by divisionally adding the coupling agent (D-10), a defect does not arise even if the kneading temperature becomes high and it is possible to promote the reaction of the coupling agent and promote the dispersion of the silica.

The kneading time in the step X1-10 and the step X2-10 is not limited particularly, but the kneading time in each step is preferably not less than 3.0 minutes, more preferably not less than 4.0 minutes, further preferably not less than 4.5 minutes since the kneaded product in which silica is well dispersed tends to be obtained efficiently. On the other hand, the kneading time in each step is preferably not more than 9 minutes, more preferably not more than 8 minutes, further preferably not more than 7 minutes.

In one embodiment of the tenth invention, it is preferable to keep the kneaded product at 150° C. to 190° C., or more preferably at 150° C. to 180° C., for 10 to 120 seconds after the temperature reaches the highest temperature in the step X1-10 and/or the step X2-10 and the kneading is finished since the reaction between the coupling agent and the silica is completely performed.

Step F-10

In the step F-10, the kneaded product obtained in the step X2-10 is cooled and then the vulcanizing agent (E-10) containing the vulcanizer and the vulcanization accelerator is added and the mixture is kneaded with an open roll and the like to obtain an unvulcanized rubber composition.

While the vulcanization accelerator may be added in the step F-10 at a time, it is preferable that a part or all amount is added in the step X1-10 and/or the step X2-10 and then the remaining amount is added in the step F-10. By adding a part or all amount in the step X1-10 and/or the step X2-10, dispersion between the silica and the rubber component can be promoted. It is more preferable that a part or all amount of the guanidine vulcanization accelerator is added in the step X1-10 and/or the step X2-10 since dispersibility of the silica can be more promoted.

It is preferable that the kneaded product obtained in the step X2-10 is normally cooled to 100° C. or less, preferably to 20 to 80° C.

The temperature at discharge of kneading in the step F-10 is preferably not higher than 110° C., more preferably not higher than 100° C. If the temperature at discharge exceeds 110° C., rubber burning (scorch) tends to easily arise. On the other hand, the lower limit of the temperature at discharge of kneading in the step F-10 is not limited particularly, but is preferably not lower than 80° C.

The kneading time in the step F-10 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-10 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the tenth invention can be obtained successfully.

Rubber Composition for Tire

The rubber composition for tire according to the tenth invention can be used for any component of a tire and among these, can be suitably used for a tread, a sidewall or an electrically conductive component since it is the rubber composition for tire in which fuel efficiency, abrasion resistance, wet grip performance and electrical conductivity are improved in a good balance.

Tire

In addition, a tire of the tenth invention can be produced with a normal method by use of the rubber composition for tire according to the tenth invention. That is, the rubber composition for tire produced by the production method of the tenth invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the tenth invention can be produced.

It is noted that the tire of the tenth invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars. Additionally, examples of a non-pneumatic tire include a solid tire, an airless tire, a truck belt and the like.

One suitable embodiment of the tenth invention is an airless tire having a tread composed of the rubber composition for tire according to the tenth invention. In an airless tire, electrical conductivity throughout the tire tends to be inferior since an electrically conductive component such as a steel cord does not exist or a wheel is made of a resin, however, by using a tread comprising the rubber composition according to the tenth invention for an airless tire, satisfactory electrical conductivity can be obtained.

<Eleventh Invention>

The eleventh invention is a production method of a rubber composition for tire comprising a rubber component (A-11) comprising at least one selected from the group consisting of a natural rubber and a synthetic diene rubber, silica (B-11), carbon black (C-11), a coupling agent (D1-11) represented by the following chemical formula (1), a coupling agent (D2-11) having a sulfide group, and a vulcanizing agent (E-11) comprising a vulcanizer and a vulcanization accelerator, the method comprising:

(step X1-11) a step X1-11 of kneading A-11, a part of B-11, D1-11 and optionally a part of E-11,
(step X2-11) a step X2-11 of kneading the kneaded product of the step X1-11, the remaining amount of B-11, D2-11 and optionally a part of E-11, and
(step F-11) a step F-11 of kneading the kneaded product of the step X2-11 and the remaining amount of E-11.

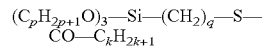

Chemical formula (1):

In the chemical formula (1), p represents an integer of 1 to 3, q represents an integer of 1 to 5, and k represents an integer of 5 to 12.

It is preferable that the rubber component (A-11) comprises a butadiene rubber and/or a styrene butadiene rubber which has a functional group that reacts with silica.

It is preferable that the nitrogen adsorption specific surface area of the silica is not less than 160 m$^2$/g and the total added amount of the silica is not less than 40 parts by mass based on 100 parts by mass of the rubber component.

It is preferable that the added amount of the coupling agent in each of the step X1-11 and the step X2-11 is 4 to 10 parts by mass based on 100 parts by mass of the silica added in each step.

It is preferable that the added amount of the silica in the step X1-11 is 50 to 95% by mass of the total added amount of silica.

It is preferable that the production method is a production method of the rubber composition further comprising a plasticizer and not less than 50% by mass of the total added amount of a plasticizer is kneaded in the step X1-11.

It is preferable that the highest temperature in the step X1-11 is 140° C. to 200° C.

It is preferable that after the kneading in the step X1-11 is finished, the production method comprises a step of keeping the kneaded product at 150 to 190° C. for 10 to 120 seconds.

It is preferable that a part or all amount of the vulcanization accelerator is kneaded in the step X1-11 and/or the step X2-11.

It is preferable that the production method is a production method of the rubber composition further comprising an anti-aging agent and an anti-aging agent is kneaded in the step X2-11.

It is preferable that the production method is a production method of the rubber composition further comprising a surfactant and a surfactant is kneaded in the step X1-11 and/or the step X2-11.

The eleventh invention also relates to a tire having a tire component composed of the rubber composition for tire produced by the above production method of the rubber composition for tire.

According to the eleventh invention, it is possible to produce a rubber composition for tire in which fuel efficiency, abrasion resistance and wet grip performance are improved in a good balance. Further, by use of a tire having a tire component composed of the produced rubber composition for tire, it is possible to produce a tire in which fuel efficiency, abrasion resistance and wet grip performance are improved in a good balance.

The rubber composition according to the eleventh invention is characterized by comprising a specified rubber component (A-11), silica (B-11), carbon black (C-11), coupling agents (D1-11) and (D2-11), and a vulcanizing agent (E-11) comprising a vulcanizer and a vulcanization accelerator.

Rubber Component (A-11)

The rubber component (A-11) is characterized by comprising at least one selected from the group consisting of a natural rubber and a synthetic diene rubber, preferably comprising two thereof. By blending a plurality of diene rubbers, it is possible to compensate for a defect of a particular rubber and improve physical properties in a good balance. It is preferable that a main chain or a terminal of these rubber components is modified with a modifier. In addition, a part thereof may have a branched structure by use of a multifunctional modifier such as, for example, a tin tetrachloride and a silicon tetrachloride. It is noted that a type or compounded amount of a rubber component can be appropriately selected depending on a part to which the rubber component is applied.

The natural rubber includes a natural rubber (NR), and a modified natural rubber such as an epoxidized natural rubber (ENR), a hydrogenated natural rubber (HNR), a deproteinized natural rubber (DPNR), a high purity natural rubber (HPNR) and the like.

The NR is not limited particularly and those generally used in the tire industry such as SIR20, RSS#3, TSR20 and the like can be used.

In the case where the rubber composition comprises NR, the content thereof in the rubber component (A-11) is preferably not less than 5% by mass, more preferably not less than 10% by mass since breaking resistance of the rubber composition improves. On the other hand, the content of NR is preferably not more than 80% by mass, more preferably not more than 70% by mass, further preferably not more than 50% by mass since fuel efficiency and abrasion resistance of the rubber composition are excellent.

Examples of the synthetic diene rubber include an isoprene rubber (IR), a styrene butadiene rubber (SBR), a butadiene rubber (BR), a styrene-isoprene-butadiene rubber (SIBR) and the like.

Among synthetic diene rubbers, it is preferable that the rubber composition comprises SBR since it is excellent in processability, wet grip performance and dry grip performance. The SBR is not limited particularly and examples thereof include an unmodified solution-polymerized styrene-butadiene rubber (S-SBR), an unmodified emulsion-polymerized styrene-butadiene rubber (E-SBR), and modified SBRs of these (modified E-SBR, modified S-SBR) and the like. Examples of the modified SBR include a modified SBR in which a terminal and/or a main chain is modified, a modified SBR coupled by a tin or silicon compound (such as a condensate or one having a branched structure) and the like. Among these SBRs, S-SBR and modified S-SBR are preferable since they can improve grip performance and abrasion resistance in a good balance, and from the viewpoint of a reaction with silica, a modified SBR having at least one selected from the group consisting of a silyl group, an amino group, an amide group, a hydroxyl group and an epoxy group is particularly preferable. While these SBRs can be used alone, SBRs having different physical properties such as a content of styrene may be used in combination depending on application. It is noted that SBRs may be appropriately selected depending on a part to which they are applied.

The styrene content of SBR is preferably not less than 5% by mass, more preferably not less than 10% by mass, further preferably not less than 20% by mass from the viewpoint of wet grip performance, dry grip performance and rubber strength. On the other hand, the styrene content of SBR is preferably not more than 60% by mass, more preferably not more than 50% by mass, further preferably not more than 40% by mass from the viewpoint of fuel efficiency. It is noted that the styrene content of SBR herein is calculated from a $^1$H-NMR measurement.

The vinyl bond amount of SBR is preferably not less than 10 mol %, more preferably not less than 15 mol %, further preferably not less than 20 mol % from the viewpoint of wet grip performance, dry grip performance and rubber strength. On the other hand, the vinyl bond amount of SBR is preferably not more than 65 mol %, more preferably not more than 60 mol %, further preferably not more than 30 mol % from the viewpoint of fuel efficiency. It is noted that the vinyl bond amount of SBR herein refers to a vinyl bond amount of a butadiene part and is calculated from a $^1$H-NMR measurement.

In the case where the rubber composition comprises SBR, the content thereof in the rubber component (A-11) is preferably not less than 10% by mass, more preferably not less than 20% by mass, further preferably not less than 30% by mass from the viewpoint of wet grip performance and dry grip performance. On the other hand, the content of SBR is preferably not more than 90% by mass, more preferably not more than 80% by mass from the viewpoint of abrasion resistance.

Further, it is preferable that the rubber component comprises BR since it is excellent in abrasion resistance. In general, a rubber composition in which a white filler such as silica (B-11) is compounded in BR has a problem that dispersibility of the filler is low and it is difficult to obtain desired performance. However, in the eleventh invention, the reaction between a filler and a rubber component is improved by divisionally kneading a specified coupling agent. Accordingly, dispersibility of a filler increases and fuel efficiency and abrasion resistance are improved as well as satisfactory processability can be obtained, thereby synergistically improving a balance among these performances.

Examples of the BR include a high-cis BR in which a cis content is not less than 90%, a modified BR in which a terminal and/or a main chain is modified, a modified BR coupled by a tin or silicon compound (such as a condensate or one having a branched structure) and the like. Among these BRs, a high-cis BR is preferable from the viewpoint of achievement of excellent abrasion resistance, and from the viewpoint of the reaction with silica, a modified BR in which a terminal and/or a main chain is modified, particularly a modified BR having at least one selected from the group consisting of a silyl group, an amino group, an amide group, a hydroxyl group and an epoxy group is preferable. It is noted that BRs may be appropriately selected depending on a part to which they are applied.

In the case where the rubber composition comprises BR, the content thereof in the rubber component (A-11) is preferably not less than 5% by mass, more preferably not less than 8% by mass, further preferably not less than 10% by mass from the viewpoint of abrasion resistance. On the other hand, the content of BR is preferably not more than 80% by mass, more preferably not more than 75% by mass, further preferably not more than 70% by mass from the viewpoint of processability.

In particular, the modified SBR or modified BR, due to a strong interaction of its functional groups, coagulates itself and dispersion of a filler usually becomes all the more difficult. However, in the eleventh invention, by divisionally kneading a specified coupling agent, the coagulation of the rubber component is prevented and the reaction with silica is promoted.

Silica (B-11)

The silica (B-11) is not limited particularly and ones generally used in the tire industry can be used. Examples thereof include dry processed silica (silicic anhydride) and wet processed silica (hydrous silicic acid) and the like, and wet processed silica is preferable because it has more silanol groups.

The nitrogen adsorption specific surface area ($N_2SA$) of the silica (B-11) is preferably not less than 40 m$^2$/g, more preferably not less than 50 m$^2$/g, further preferably not less than 100 m$^2$/g, particularly preferably not less than 130 m$^2$/g, most preferably not less than 160 m$^2$/g from the viewpoint of breaking resistance. On the other hand, the $N_2SA$ of the silica (B-11) is preferably not more than 500 m$^2$/g, more preferably not more than 300 m$^2$/g, further preferably not more than 250 m$^2$/g, particularly preferably not more than 200 m$^2$/g from the viewpoint of fuel efficiency and processability. It is noted that the $N_2SA$ of the silica (B-11) herein is a value as measured with the BET method in accordance with ATSM D3037-81.

The content (total added amount) of the silica (B-11) is preferably not less than 10 parts by mass, more preferably not less than 20 parts by mass, further preferably not less than 30 parts by mass, particularly preferably not less than 40 parts by mass based on 100 parts by mass of the rubber component (A-11) from the viewpoint of fuel efficiency and wet grip performance. On the other hand, the total content of the silica (B-11) is preferably not more than 200 parts by mass, more preferably not more than 150 parts by mass, further preferably not more than 120 parts by mass from the viewpoint of dispersibility of a filler into the rubber component and processability.

Carbon Black (C-11)

The carbon black (C-11) is not limited particularly and ones generally used in the tire industry such as GPF, FEF, HAF, ISAF, SAF and the like can be used, and these carbon black may be used alone, or may be used in combination with two or more thereof.

The nitrogen adsorption specific surface area ($N_2SA$) of the carbon black (C-11) is preferably not less than 80 m$^2$/g, more preferably not less than 100 m$^2$/g from the viewpoint of weather resistance and antistatic performance. On the other hand, the $N_2SA$ of the carbon black (C-11) is preferably not more than 200 m$^2$/g, more preferably not more than 150 m$^2$/g from the viewpoint of processability. It is noted that the $N_2SA$ of the carbon black (C-11) herein is a value as measured in accordance with JIS K6217, method A.

The content (total added amount) of the carbon black (C-11) is preferably not less than 1 part by mass, more preferably not less than 3 parts by mass based on 100 parts by mass of the rubber component (A-11). If the content of the carbon black (C-11) is less than 1 part by mass, the effect obtained by inclusion of the carbon black may not be obtained sufficiently. On the other hand, the content of the carbon black (C-11) is preferably not more than 30 parts by mass, more preferably not more than 10 parts by mass from the viewpoint of fuel efficiency and processability.

Coupling Agent

The coupling agent (D1-11) is a compound represented by the following chemical formula (1).

Chemical formula (1):

In the chemical formula (1), p represents an integer of 1 to 3, q represents an integer of 1 to 5, and k represents an integer of 5 to 12.

The p in the compound represented by the chemical formula (1) is an integer of 1 to 3, preferably an integer of 2 from the viewpoint of reactivity with silica.

The q in the compound represented by the chemical formula (1) is an integer of 1 to 5, preferably an integer of 2 to 5, more preferably an integer of 3 since a rubber molecule and silica are bonded in an appropriate length and low heat build-up property is improved.

The k in the compound represented by the chemical formula (1) is an integer of 5 to 12, preferably an integer of 6 to 10, more preferably an integer of 7 since both reactivity with a rubber molecule and processability are improved.

Examples of the coupling agent (D1-11) represented by the chemical formula (1) include 3-hexanoyl thiopropyl triethoxysilane, 3-octanoyl thiopropyl triethoxysilane, 3-decanoyl thiopropyl triethoxysilane, 3-lauroyl thiopropyl triethoxysilane, 2-hexanoyl thioethyl triethoxysilane, 2-octanoyl thioethyl triethoxysilane, 2-decanoyl thioethyl triethoxysilane, 2-lauroyl thioethyl triethoxysilane, 3-hexanoyl thiopropyl trimethoxysilane, 3-octanoyl thiopropyl trimethoxysilane, 3-decanoyl thiopropyl trimethoxysilane, 3-lauroyl thiopropyl trimethoxysilane, 2-hexanoyl thioethyl trimethoxysilane, 2-octanoyl thioethyl trimethoxysilane, 2-decanoyl thioethyl trimethoxysilane, 2-lauroyl thioethyl trimethoxysilane and the like and these may be used alone, or may be used in combination with two or more thereof. Among these, 3-octanoyl thiopropyl triethoxysilane (NTX silane manufactured by Momentive Performance Materials) is particularly preferable from the viewpoint of easy availability and the cost.

The coupling agent (D2-11) is a coupling agent having a sulfide group and examples thereof include bis(3-triethoxysilylpropyl)tetrasulfide, bis(2-triethoxysilylethyl)tetrasulfide, bis(3-trimethoxysilylpropyl)tetrasulfide, bis(2-trimethoxysilylethyl)tetrasulfide, bis(3-triethoxysilylpropyl)trisulfide, bis(3-trimethoxysilylpropyl)trisulfide, bis(3-triethoxysilylpropyl)disulfide, bis(3-trimethoxysilylpropyl)disulfide, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 2-trimethoxysilylethyl-N,N-dimethylthiocarbamoyl tetrasulfide, 3-trimethoxysilylpropylbenzothiazolyl tetrasulfide, 3-triethoxysilylpropylbenzothiazole tetrasulfide, 3-triethoxysilylpropyl methacrylate monosulfide, 3-trimethoxysilylpropyl methacrylate monosulfide and the like. Suitable examples of these coupling agents include Si75 (bis(3-triethoxysilylpropyl)disulfide), Si69 (bis(3-triethoxysilylpropyl)tetrasulfide) manufactured by Evonik Industries, which are available as a mixture that generally has a certain distribution, and the like.

The total content of the coupling agents (D1-11) and (D2-11) is preferably not less than 4 parts by mass, more preferably not less than 5 parts by mass, further preferably not less than 6 parts by mass based on 100 parts by mass of the total content of the silica from the viewpoint of the effect of improvement of a reaction with a filler and processability. On the other hand, the total content of the coupling agents is preferably not more than 20 parts by mass, more preferably not more than 10 parts by mass, further preferably not more than 9 parts by mass from the viewpoint of the effect of improving dispersibility of silica that is compatible with the increase of the cost.

Vulcanizing Agent (E-11)

The vulcanizing agent (E-11) comprises a vulcanizer (E1-11) and a vulcanization accelerator (E2-11). Vulcanizing agents generally used in the rubber industry such as a vulcanization accelerator auxiliary agent can be also used.

Vulcanizer (E1-11)

The vulcanizer (E1-11) is not limited particularly and ones generally used in the tire industry can be used. Since the effect of the eleventh invention can be successfully obtained, sulfur is preferable and powder sulfur is more preferable. Sulfur can be used in combination with other vulcanizers. Examples of other vulcanizers include a vulcanizer containing a sulfur atom such as TACKIROL V200 manufactured by Taoka Chemical Co., Ltd., Duralink HTS (1,6-hexamethylene-sodium dithiosulfate dehydrate) manufactured by Flexsys, KA9188 (1,6-bis(N,N'-dibenzylthiocarbamoyldithio) hexane) manufactured by LANXESS and the like, an organic peroxide such as dicumyl peroxide and the like.

The content of the vulcanizer (E1-11) is preferably not less than 0.1 part by mass, more preferably not less than 0.5 part by mass based on 100 parts by mass of the rubber component (A-11). On the other hand, the content of the vulcanizer (E1-11) is preferably not more than 15 parts by mass, more preferably not more than 5 parts by mass. If the content of the vulcanizer (E1-11) is within the above range, satisfactory tensile strength, abrasion resistance and heat resistance can be obtained.

Vulcanization Accelerator (E2-11)

The vulcanization accelerator (E2-11) is not limited particularly and ones generally used in the tire industry can be used. Examples thereof include thiazole vulcanization accelerators such as 2-mercaptobenzothiazole, dibenzothiazyl disulphide and N-cyclohexyl-2-benzothiazyl sulfen amide; thiuram vulcanization accelerators such as tetramethylthiuram monosulfide and tetramethylthiuram disulfide; sulfenamide vulcanization accelerators such as N-cyclohexyl-2-benzothiazolsulfenamide, N-t-butyl-2-benzothiazolsulfenamide, N-oxyethylene-2-benzothiazolsulfenamide, and N,N'-diisopropyl-2-benzothiazolsulfenamide; guanidine vulcanization accelerators such as diphenylguanidine, diorthotolyl guanidine and orthotolylbiguanide; and the like. Among these, sulfenamide vulcanization accelerators and guanidine vulcanization accelerators are preferable since both the rubber elastic modulus and processability are improved, and guanidine vulcanization accelerators are particularly preferable since they are excellent in fuel efficiency and a balance with other physical properties of the rubber.

The examples of the guanidine vulcanization accelerator include 1,3-diphenylguanidine, 1,3-di-o-tolylguanidine, 1-o-tolylbiguanide, di-o-tolylguanidine salt of dicatechol borate, 1,3-di-o-cumenylguanidine, 1,3-di-o-biphenylguanidine, 1,3-di-o-cumenyl-2-propionylguanidine and the like. Among these, 1,3-diphenylguanidine, 1,3-di-o-tolylguanidine and 1-o-tolylbiguanide are more preferable since they have high reactivity.

The content of the vulcanization accelerator (E2-11) is preferably not less than 0.1 part by mass, more preferably not less than 0.2 part by mass based on 100 parts by mass of the rubber component (A-11). On the other hand, the content of the vulcanization accelerator (E2-11) is preferably not more than 5 parts by mass, more preferably not more than 3 parts by mass. If the content of the vulcanization accelerator (E2-11) is within the above range, the reduction of the rubber elastic modulus and the deterioration of breaking resistance can be prevented.

Other Compounding Agents

The rubber composition for tire of the eleventh invention can suitably comprise, in addition to the above components, compounding agents that have been used in the rubber industry such as, for example, a plasticizer (F-11), a filler for reinforcement other than silica and carbon black, an anti-aging agent (G-11), an antioxidant, a stearic acid, wax and the like as necessary.

Plasticizer (F-11)

Since processability is improved and the strength of rubber is increased, it is preferable that the rubber composition for tire of the eleventh invention comprises the plasticizer (F-11). The plasticizer (F-11) is not limited particularly and ones generally used in the tire industry can be used, and examples thereof include oil, liquid polymer, liquid resin and the like. Among these, oil is preferable since cost and processability can be improved in a good balance.

Examples of oil include process oil, vegetable oil and fat, animal oil and fat and the like. Examples of process oil include paraffin process oil, naphthene process oil, aromatic process oil and the like. Examples of vegetable oil and fat include castor oil, cotton seed oil, linseed oil, rape seed oil, soy bean oil, palm oil, coconut oil, peanut oil, rosin, pine oil, pine tar, tall oil, corn oil, rice oil, sesame oil, olive oil, sun flower oil, palm kernel oil, *camellia* oil, jojoba oil, macadamia nut oil, safflower oil, wood oil and the like. Examples of animal oil and fat include oleyl alcohol, fish oil, beef fat and the like. Among these, process oil is preferable since it is advantageous in processability, and process oil having a low content of polycyclic aromatic compound (PCA) (low PCA containing process oil) is preferable since it can reduce the environmental load.

Examples of low PCA containing process oils include a treated distillate aromatic extract (TDAE) obtained by re-extracting oil aromatic process oil, an aroma-alternative oil that is a mixed oil of an asphalt and a naphthene oil, a mild extraction solvates (MES), a heavy naphthene oil and the like.

In the case where the rubber composition comprise oil as the plasticizer (F-11), the content thereof based on 100 parts by mass of the rubber component (A-11) is preferably not less than 2 parts by mass, more preferably not less than 5 parts by mass from the viewpoint of the effect of improving processability. On the other hand, the content of oil is preferably not more than 60 parts by mass, more preferably not more than 50 parts by mass, further preferably not more than 40 parts by mass from the viewpoint of the load in the process. It is noted that the content of oil herein does not include an oil amount in an oil extended product in the case where the rubber component is an oil extended product.

Anti-Aging Agent (G-11)

The anti-aging agent (G-11) is such as a heat resistant anti-aging agent, a weather resistant anti-aging agent and the like and not limited particularly as long as it is generally used for a rubber composition and examples thereof include an amine anti-aging agent such as a naphthylamine anti-aging agent (for example, phenyl-α-naphthylamine), a diphenylamine anti-aging agent (for example, octylated diphenylamine, 4,4'-bis(α,α'-dimethylbenzyl)diphenylamine and the like), p-phenylenediamine anti-aging agent (for example, N-isopropyl-N'-phenyl-p-phenylenediamine, N-(1,3-dimethylbutyl)-N'-phenyl-p-phenylenediamine, N,N'-di-2-naphthyl-p-phenylenediamine and the like) and the like: a quinoline anti-aging agent such as a polymer of 2,2,4-trimethyl-1,2-dihydroquinoline and the like; a phenol anti-aging agent such as a monophenol anti-aging agent (for example, 2,6-di-t-butyl-4-methylphenol, styrenated phenol and the like), a bis, tris, polyphenol anti-aging agent (for example, tetrakis-[methylene-3-(3',5'-di-t-butyl-4'-hydroxyphenyl)propionate]methan) and the like. Among these, an amine anti-aging agent is preferable since it is excellent in ozone resistance and p-phenylenediamine is particularly preferable.

In the case where the rubber composition comprises the anti-aging agent (G-11), the content thereof based on 100 parts by mass of the rubber component (A-11) is preferably not less than 0.5 part by mass, more preferably not less than 1.0 part by mass from the viewpoint of ozone resistance and crack resistance. On the other hand, the content of the anti-aging agent is preferably not more than 10 parts by mass, more preferably not more than 5 parts by mass from the viewpoint of prevention of discoloration.

Surfactant

In an embodiment of the eleventh invention, it is preferable that the rubber composition further comprises a surfactant. By inclusion of a surfactant, dispersibility of the above fillers comprising silica and carbon black is improved and a discoloration of the obtained rubber composition for tire due to deterioration over time can be prevented.

Examples of the surfactant include metallic soap such as an organic acid of a metallic salt, a nonionic surfactant such as a polyoxyalkylene derivative and the like, but the surfactant is not limited particularly. These may be used alone, or two or more may be used in combination.

A suitable example of the metallic salt of an organic acid is a metallic salt of carboxylic acid. Examples of the polyoxyalkylene derivative include an ether type such as a polyoxyalkylene alkyl ether, an ester type such as a polyoxyalkylene fatty acid ester, an ether ester type such as a polyoxyalkylene glycerine fatty acid ester, a nitrogen-containing type such as a polyoxyalkylene fatty acid amide and a polyoxyalkylene alkylamine and the like. Among these, a polyoxyalkylene alkyl ether and a polyoxyalkylene fatty acid ester are particularly preferable in their fuel efficiency and a balance with other physical properties of the rubber.

The content of the surfactant is preferably not less than 0.1 part by mass, more preferably not less than 0.3 part by mass, further preferably not less than 0.6 part by mass, most preferably not less than 1.0 part by mass based on 100 parts by mass of the rubber component (A-11) from the viewpoint of the effect of improving dispersibility of silica. On the other hand, the content of the surfactant is preferably not more than 5.0 parts by mass, more preferably not more than 4.0 parts by mass, further preferably not more than 3.0 parts by mass from the viewpoint of steering stability, crack resistance, ozone resistance and discoloration resistance.

Production Method of Rubber Composition for Tire

The production method of a rubber composition for tire of the eleventh invention is characterized by dividing a kneading step into a step X1-11, a step X2-11 and a step F-11. Known kneaders can be used in each step and examples thereof include a Banbury mixer, a kneader, an open roll and the like.

Specifically, the production method of a rubber composition for tire includes a kneading process comprising a step X1-11 of kneading A-11, a part of B-11, D1-11 and optionally a part of E-11, a step X2-11 of kneading the kneaded product of the step X1-11, the remaining amount of B-11, D2-11 and optionally a part of E-11, and a step F-11 of kneading the kneaded product of the step X2-11 and the remaining amount of E-11, to obtain an unvulcanized rubber composition. The obtained unvulcanized rubber composition is then vulcanized (vulcanization process) and the rubber composition for tire according to the eleventh invention can be produced. It is noted that the timing when other compounding agents such as carbon black (C-11), a plasticizer (F-11), an anti-aging agent (G-11), a zinc oxide, a stearic acid and the like are added and kneaded is not limited particularly, and these compounding agents may be added in any of the step X1-11, the step X2-11 or the step F-11, or may be added divisionally.

Particularly, the production method of the eleventh invention is characterized in that the coupling agent (D1-11) is kneaded in the preceding step (step X1-11) before the coupling agent (D2-11) having a sulfide group is kneaded. The coupling agent (D1-11) can form homogeneous chemical bonds between the filler and the polymer without losing activity even in the kneading in the prior input as in the eleventh invention because the coupling agent does not have a plurality of alkoxysilyl groups in the molecule and the coagulation thereof is small and also because a mercapto group suitably reacting with a polymer part becomes a fatty acid thioester, thereby non-uniformity resulting from a rapid reaction is prevented.

Step X1-11

In the step X1-11, compounding agents comprising all amount of the rubber component (A-11), a part of silica (B-11), the coupling agent (D1-11) and optionally a part of the vulcanizing agent (E-11) are kneaded with a Banbury mixer and the like. From this step, the filler disperses while forming a strong bond with a rubber component, particularly with a rubber component having high affinity with the filler. Further, by use of a coupling agent (D1-11) having the structure of the chemical formula (1), since thioester groups are decomposed during kneading to gradually generate mercapto groups which have high activity, it is possible to disperse the filler while maintaining processability and promote bonding with the polymer. However, if a conventional polysulfide silane (coupling agent (D2-11)) is input in the step X1, then it releases sulfur even in this phase, thereby processability is deteriorated, dispersion of the filler is prevented and the activity of a coupling agent itself is lowered. The coupling agent (D1-11) represented by the chemical formula (1) does not release sulfur, thereby being able to continue kneading while maintaining processability according to the production method of the eleventh invention.

The added amount of the silica (B-11) in the step X1-11 is preferably not less than 50% by mass, more preferably not less than 60% by mass, further preferably not less than 70% by mass, even further preferably not less than 80% by mass of the total added amount of the silica (B-11) from the viewpoint of improvement of the effect of kneading silica, sufficient dispersion of silica and abrasion resistance. On the other hand, the added amount of the silica (B-11) in the step X1-11 is preferably not more than 95% by mass, more preferably not more than 90% by mass, further preferably not more than 85% by mass of the total added amount of the silica (B-11) from the viewpoint of the effect of adding the silica divisionally in the step X2-11 as described below, fuel efficiency and abrasion resistance.

The added amount of the coupling agent (D1-11) represented by the chemical formula (1) in the step X1-11 is preferably not less than 4 parts by mass, more preferably not less than 5 parts by mass, further preferably not less than 6 parts by mass based on 100 parts by mass of the added amount of the silica (B-11) in the step X1-11, since a reaction with the filler becomes sufficient and the excellent effect of improving processability of the coupling agent (D1-11) can be exerted. On the other hand, the added amount of the coupling agent (D1-11) represented by the chemical formula (1) in the step X1-11 is preferably not more than 20 parts by mass, more preferably not more than 10 parts by mass, further preferably not more than 9 parts by mass from the viewpoint of the effect of improving dispersibility of silica that is compatible with the increase of cost.

It is preferable that the carbon black (C-11) is added in the step X1-11 and/or the step X2-11. The added amount of the carbon black (C-11) in the step X1-11 is preferably not less than 10% by mass, more preferably not less than 50% by mass, further preferably not less than 80% by mass, most preferably 100% by mass of the total added amount of the carbon black (C-11) from the viewpoint of the improvement of dispersibility of carbon black and efficiency of the step. If the added amount of the carbon black (C-11) in the step X1-11 is less than 100% by mass, it is preferable that the remaining amount is added in the step X2-11.

While the step in which the plasticizer (F-11) is added is not limited particularly, it is preferable that not less than 50% by mass, more preferably not less than 70% by mass, further preferably not less than 80% by mass of the total added amount of the plasticizer (F-11) is added in the step X1-11. If the added amount of the plasticizer (F-11) in the step X1-11 is less than 100% by mass, it is preferable that the remaining amount is added in the step X2-11 since dispersibility of the silica which is added in the step X2-11 is more improved.

It is preferable that the surfactant is added in the step X1-11 and/or the step X2-11 from the viewpoint of promoting the effect of dispersing silica, and is preferably added in the step X1-11 since the effect of dispersing silica is more promoted and a gelation of the coupling agent can be prevented.

The temperature at discharge of kneading in the step X1-11 is not limited particularly, but is preferably not lower than 142° C., more preferably not lower than 146° C., further preferably not lower than 148° C. On the other hand, the temperature at discharge is preferably not higher than 170° C., more preferably not higher than 160° C., further preferably not higher than 155° C. If the temperature at discharge in the step X1-11 is within the above range, the kneaded product in which silica (B-11) is well dispersed tends to be obtained efficiently.

The highest temperature during kneading in the step X1-11 is not limited particularly, but is preferably not lower than 140° C., more preferably not lower than 145° C., further preferably not lower than 150° C. since the coupling agent is sufficiently reacted and the kneaded product in which the silica is well dispersed can be obtained efficiently. On the other hand, the highest temperature during kneading is preferably not higher than 200° C. for preventing a rubber burning. While a defect such as a gelation may arise if the temperature exceeds 150° C. in a normal kneading process, polysulfide silane is not added as a vulcanization accelerator in the step X1-11 according to the eleventh invention and thus a defect does not arise even if the kneading temperature becomes high and it is possible to promote the reaction of the coupling agent and promote the dispersion of the silica.

The kneading time in the step X1-11 is not limited particularly, but the kneading time in each step is preferably not less than 3.0 minutes, more preferably not less than 4.0 minutes, further preferably not less than 4.5 minutes since the kneaded product in which silica is well dispersed can be obtained efficiently. On the other hand, the respective kneading time in each step is preferably not more than 9 minutes, more preferably not more than 8 minutes, further preferably not more than 7 minutes.

In one embodiment of the eleventh invention, it is preferable to keep the kneaded product at 150° C. to 190° C. for 10 to 120 seconds after the temperature reaches the highest temperature in the step X1-11 and the kneading is finished since the reaction between the coupling agent (D1-11) and the silica is completely performed.

Step X2-11

In the step X2-11, the compounding agents comprising the remaining amount of the silica (B-11), the coupling agent (D2-11) and optionally a part of the vulcanizing agent (E-11) are added to the kneaded product of the step X1-11 and the mixture is kneaded. If the all amount of the silica is input in the step X1-11, the silica tends to be localized in a polymer portion having high affinity with silica such as a modified polymer and/or an interface portion of the polymer, however, in the production method of the eleventh invention, since the silica is respectively input divisionally in the step X1-11 and the step X2-11, the silica becomes easily dispersed through the entire rubber component. Further, the later added silica (added in the step X2-11) itself has an effect of promoting kneading by applying shear to the rubber component. Moreover, in the production method of the eleventh invention, since the coupling agent (D1-11) represented by the chemical formula (1) is kneaded in the step X1-11, an initial reduction of the activity of the coupling agent is prevented and processability throughout the kneading operation can be maintained.

In addition, by kneading the coupling agent (D2-11) having a sulfide group in the step X2-11, an initial reduction of the activity of the coupling agent is prevented and processability throughout the kneading operation can be maintained. Moreover, since the coupling agent (D2-11) can release sulfur that acts as a vulcanizer, a uniform crosslinking is promoted and the improvement of physical properties of the rubber can be attempted.

The added amount of the coupling agent (D2-11) in the step X2-11 is preferably not less than 4 parts by mass, more preferably not less than 5 parts by mass, further preferably not less than 6 parts by mass based on 100 parts by mass of the added amount of the silica (B-11) in the step X2-11 since the reaction with a filler can be made sufficient and the effect of improving excellent processability of the coupling agent (D2-11) can be brought out. On the other hand, the added amount of the coupling agent (D2-11) represented by the chemical formula (1) in the step X2-11 is preferably not more than 20 parts by mass, more preferably not more than 10 parts by mass, further preferably not more than 9 parts by mass from the viewpoint of the effect of improving dispersibility of silica that is compatible with the increase of the cost.

The step in which the anti-aging agent (G-11) is added is not limited particularly, but from the viewpoint of operation efficiency and prevention of activity reduction of the anti-aging agent, it is preferable that all amount is added in the step X2-11.

The temperature at discharge of kneading in the step X2-11 is not limited particularly, but is preferably not lower than 100° C., more preferably not lower than 120° C., further preferably not lower than 130° C. On the other hand, the temperature at discharge is preferably not higher than 200° C., more preferably not higher than 170° C., further preferably not higher than 160° C. If the temperature at discharge in the step X2-11 is within the above range, the kneaded product in which silica (B-11) is well dispersed tends to be obtained efficiently.

The highest temperature during kneading in the step X2-11 is not limited particularly, but is preferably not lower than 100° C., more preferably not lower than 120° C., further preferably not lower than 130° C. since the coupling agent (D2-11) having a sulfide group is sufficiently reacted and the kneaded product in which the silica is well dispersed can be obtained efficiently. On the other hand, the highest temperature during kneading is preferably not higher than 200° C., more preferably not higher than 170° C., further preferably not higher than 160° C. for preventing a rubber burning.

The kneading time in the step X2-11 is not limited particularly, but the kneading time is preferably not less than 3.0 minutes since the kneaded product in which silica is well dispersed can be obtained efficiently. On the other hand, the respective kneading time is preferably not more than 9 minutes, more preferably not more than 8 minutes, further preferably not more than 7 minutes.

Step F-11

In the step F-11, the kneaded product obtained in the step X2-11 is cooled and then the vulcanizing agent (E-11) containing the vulcanizer and the vulcanization accelerator is added and the mixture is kneaded with an open roll and the like to obtain an unvulcanized rubber composition.

While the vulcanization accelerator may be added in the step F-11 at a time, it is preferable that a part or all amount is added in the step X1-11 and/or the step X2-11 and then the remaining amount is added in the step F-11. By adding a part or all amount in the step X1-11 and/or the step X2-11, dispersion between the silica and the rubber component can be promoted. It is more preferable that a part or all amount of the guanidine vulcanization accelerator is added in the step X1-11 and/or the step X2-11 since dispersibility of the silica can be more promoted.

It is preferable that the kneaded product obtained in the step X2-11 is normally cooled to 100° C. or less, preferably to 20 to 80° C.

The temperature at discharge of kneading in the step F-11 is preferably not higher than 110° C., more preferably not higher than 100° C. If the temperature at discharge exceeds 110° C., a rubber burning (scorch) tends to easily arise. On the other hand, the lower limit of the temperature at discharge of kneading in the step F-11 is not limited particularly, but is preferably not lower than 80° C.

The kneading time in the step F-11 is not limited particularly, but is normally not less than 30 seconds, preferably 1 to 30 minutes.

Vulcanization Process

The vulcanized rubber composition can be obtained by vulcanizing the unvulcanized rubber composition obtained in the step F-11 by a known method. The vulcanization temperature of the unvulcanized rubber composition is preferably not lower than 120° C., more preferably not lower than 140° C. On the other hand, the vulcanization temperature is preferably not higher than 200° C., more preferably not higher than 180° C. If the vulcanization temperature is within the above range, the effect of the eleventh invention can be obtained successfully.

Rubber Composition for Tire

The rubber composition for tire according to the eleventh invention can be used for any component of a tire and among these, can be suitably used for a tread or a sidewall since it is the rubber composition for tire in which processability, fuel efficiency and abrasion resistance are improved in a good balance.

Tire

In addition, a tire of the eleventh invention can be produced with a normal method by use of the rubber composition for tire according to the eleventh invention. That is, the rubber composition for tire produced by the production method of the eleventh invention is extruded into the shape of a component of a tire such as a tread at an unvulcanized state, laminated with other components of the tire in a tire building machine, and molded by a usual method to form an unvulcanized tire. This unvulcanized tire is heated and pressurized in a vulcanizer and the tire of the eleventh invention can be produced. It is noted that the tire of the eleventh invention may be a pneumatic tire or a non-pneumatic tire. If the tire is a pneumatic tire, it can be suitably used for tires for passenger vehicle, tires for truck or bus, tires for motorbike, high performance tires and the like. It is noted that high performance tires as used herein is a tire which is particularly excellent in grip performance and also includes tires for competition used for racing cars.

EXAMPLE

The present invention will be described based on Examples, but the present invention is not limited thereto only.

A variety of chemicals used in Examples and Comparative Examples will be collectively explained below.

NR: TSR20

SBR 1: Buna SL4525-0 (styrene content: 25% by mass, non-oil-extended, non-modified S-SBR) manufactured by LANXESS SBR 2: SBR (styrene content: 37.5% by mass, vinyl bond amount: 55.8 mol %, non-oil-extended, terminal-modified S-SBR having an amino group and an alkoxysilyl group) prepared in the following production example of modified SBR 2

SBR 3: SBR (styrene content: 25% by mass, vinyl bond amount: 55 mol %, non-oil-extended, terminal-modified S-SBR having an amino group and an alkoxysilyl group) prepared in the following production example of modified SBR 3

BR 1: BR150B (high-cis BR, cis-content: 97% by mass) manufactured by Ube Industries, Ltd.

BR 2: BR (cis-content: 29% by mass, terminal-modified BR having an amino group and an alkoxysilyl group) prepared in the following production example of modified BR 2

BR 3: BR (cis-content: 97% by mass, terminal-modified BR having an amino group and an alkoxysilyl group) prepared in the following production example of modified BR 3

Carbon black 1: DIABLACK N220 ($N_2SA$: 114 $m^2/g$, DBP oil absorption amount: 115 ml/100 g) manufactured by Mitsubishi Chemical Corporation Carbon black 2: LIONITE (electrically conductive carbon black) ($N_2SA$: 1,052 $m^2/g$, DBP oil absorption amount: 378 ml/100 g, iron content: 1,330 ppm) manufactured by Lion Corporation Silica 1: Ultrasil VN3 ($N_2SA$: 175 $m^2/g$) manufactured by Evonik Industries Silica 2: ZEOSIL 115MP ($N_2SA$: 100 $m^2/g$) manufactured by Rhodia Co., Ltd.

Coupling agent 1: NXT (3-octanoyl thio-1-propyl triethoxysilane, in the chemical formula (1), p: 2, q: 3, k: 7) manufactured by Momentive Performance Materials Coupling agent 2: Si69 (bis(3-triethoxysilylpropyl)tetrasulfide) manufactured by Degussa GmbH Coupling agent 3: Si75 (bis(3-triethoxysilylpropyl)disulfide) manufactured by Evonik Industries Oil 1: Diana Process Oil AH-24 manufactured by Idemitsu Kosan Co., Ltd.

Oil 2: VIVATEC 500 manufactured by H&R Co., Ltd.

Wax: OZOACE 0355 manufactured by Nippon Seiro Co., Ltd.

Surfactant: EMULGEN 123P (non-ionic surfactant, polyoxyethylene lauryl ether) manufactured by Kao Corporation Stearic acid: stearic acid beads "Tsubaki" manufactured by NOF Corporation Zinc oxide: Zinc oxide III manufactured by HakusuiTech Co., Ltd.

Sulfur: sulfur powder manufactured by TSURUMI CHEMICAL INDUSTRY CO., LTD.

Vulcanization accelerator 1: Nocceler NS (N-t-butyl-2-benzothiazolylsulfeneamide) manufactured by OUCHI SHINKO CHEMICAL INDUSTRIAL CO., LTD.

Vulcanization accelerator 2: Nocceler D (N,N'-Diphenylguanidine) manufactured by OUCHI SHINKO CHEMICAL INDUSTRIAL CO., LTD.
Anti-aging agent: Nocrac 6C (N-(1,3-dimethylbutyl)-N'-phenyl-p-phenylenediamine) manufactured by OUCHI SHINKO CHEMICAL INDUSTRIAL CO., LTD.

The production example of the modified SBR and the modified BR, and an analytical method will be shown.

Preparation of Terminal Modifier

Under a nitrogen atmosphere, 23.6 g of 3-(N,N-dimethylamino)propyl trimethoxysilane (manufactured by Azmax Co., Ltd.) was put into a 100 ml measuring flask, and hexane anhydride (made by Kanto Chemical Co., Inc.) was further added to adjust the total amount to 100 ml to prepare a terminal modifier.

Production Example of Modified SBR 2

To a sufficiently nitrogen-substituted pressure-resistant vessel of 30 L were added 18 L of n-hexane (manufactured by KANTO CHEMICAL CO., INC.), 740 g of styrene (manufactured by KANTO CHEMICAL CO., INC.), 1,260 g of butadiene (available from TAKACHIHO TRADING CO., LTD) and 17 mmol of tetramethylethylenediamine (manufactured by KANTO CHEMICAL CO., INC.) and the temperature was elevated to 40° C. Then, 10.5 mL of butyllithium (manufactured by KANTO CHEMICAL CO., INC.) was added and the temperature was elevated to 50° C., followed by stirring for three hours. Next, 3.5 mL of 0.4 mol/L silicon trachloride/hexane solution was added, followed by stirring for 30 minutes. Then, 30 mL of the above terminal modifier was added, followed by stirring for 30 minutes. To a reaction solution was added 2 mL of methanol (manufactured by KANTO CHEMICAL CO., INC.) into which 0.2 g of 2,6-tert-butyl-p-cresol (manufactured by OUCHI SHINKO CHEMICAL INDUSTRIAL CO., LTD.) was dissolved and then the reaction solution was put into a stainless steel vessel in which 18 L of methanol was contained to collect an aggeregate. The obtained aggregate was dried under reduced pressure for 24 hours to obtain a terminal-modified S-SBR (S-SBR 2). As a result of analyses, the Mw was 925,000, a styrene content was 37.5% by mass and a vinyl bond amount was 55.8 mol %.

Production Example of Modified SBR 3

To a sufficiently nitrogen-substituted autoclave reactor of 5 L were put 2,750 g of cyclohexane, 50 g of tetrahydrofuran, 125 g of styrene and 375 g of butadiene and the temperature within the reactor was adjusted to 10° C., then a cyclohexane solution containing 5.8 mmol of n-butyllithium was added, followed by a polymerization reaction at 50° C. to 80° C. for three hours. Then, a cyclohexane solution containing 4.96 mmol of N-[3-(trimethoxysilyl)-propyl]-N,N'-diethyl-N'-trimethylsilyl-ethan-1,2-diamine was added to the obtained polymer solution, followed by a reaction for 15 minutes. Then, to the obtained polymer solution was further added 2 g of 2,6-di-tert-butyl-p-cresol, and the mixture was desolvated by performing steam stripping with hot water in which pH was adjusted to 9 with sodium hydroxide and then dried with a hot roll in which the temperature was adjusted to 110° C., to obtain the SBR 3. As a result of analyses, the Mw was 560,000, a styrene content was 25% by mass and a vinyl bond amount was 55 mol %.

Production Example of Modified BR 2

To a sufficiently nitrogen-substituted pressure-resistant vessel of 30 L were added 18 L of n-hexane (manufactured by KANTO CHEMICAL CO., INC.), 2000 g of butadiene (available from TAKACHIHO TRADING CO., LTD) and 2 mmol of tetramethylethylenediamine (TMEDA, manufactured by KANTO CHEMICAL CO., INC.) and the temperature was elevated to 60° C. Then, 10.3 mL of butyllithium (manufactured by KANTO CHEMICAL CO., INC.) was added and the temperature was elevated to 50° C., followed by stirring for three hours. Then, 11.5 mL of the above produced terminal modifier was added, followed by stirring for 30 minutes. To a reaction solution were added 15 mL of methanol (manufactured by KANTO CHEMICAL CO., INC.) and 0.1 g of 2,6-tert-butyl-p-cresol (manufactured by OUCHI SHINKO CHEMICAL INDUSTRIAL CO., LTD.) and then the reaction solution was put into a stainless steel vessel in which 18 L of methanol was contained to collect an aggeregate. The obtained aggregate was dried under reduced pressure for 24 hours to obtain a terminal-modified BR (BR 2). As a result of analyses, the Mw was 670,000, Mw/Mn was 1.34, a cis content was 29% by mass and a vinyl bond amount was 26 mol %.

Production Example of Modified BR 3

To a sufficiently nitrogen-substituted autoclave reactor of 5 L were put 2,400 g of cyclohexane and 300 g of butadiene, and thereto was added a catalyst, which was previously prepared by reacting and maturing a cyclohexane solution of neodymium versatate (0.09 mmol), a toluene solution of methylalumoxane (1.0 mmol), a toluene solution of diisobutylaluminum hydride (3.5 mmol) and diethylaluminum chloride (0.18 mmol), and 1,3-butadiene (4.5 mmol) at 50° C. for 30 minutes. A polymerization reaction was conducted at 80° C. for 45 minutes. Then, while keeping the reaction temperature at 60° C., a toluene solution of 3-glycidoxypropyltrimethoxysilane (4.5 mmol) was added, followed by a reaction for 30 minutes to modify an active terminal of a first conjugated diene polymer and an active terminal of a second conjugated diene polymer. After that, a methanol solution containing 1.5 g of 2,4-di-tert-butyl-p-cresol was added and a solution of the above modified polymer was added into an aqueous solution of 20 L in which pH was adjusted to 10 with sodium hydroxide, followed by desolvating at 110° C. for two hours and drying with a hot roll of 110° C., to obtain the BR 2. As a result of analyses, the Mw was 350,000, a cis content was 97% and a vinyl bond amount was 1.1 mol %.

Measurement of Weight-Average Molecular Weight Mw and Number-Average Molecular Weight Mn The weight-average molecular weight and number-average molecular weight were calibrated with polystyrene standards based on measurement values determined with a gel permeation chromatograph (GPC) (GPC-8000 series manufactured by Tosoh Corporation; detector: differential refractometer; column: TSKGEL SUPERMALTPORE HZ-M manufactured by Tosoh Corporation).

Measurement of Styrene Content and Vinyl Bond Amount

A structural identification was conducted with an NMR device of JNM-ECA series manufactured by JEOL Ltd. and a styrene content and a vinyl bond amount were calculated.

Measurement of Cis Content

A cis content was calculated by infrared absorption spectrometry (FT/IR-5300 (Fourier transform infrared spectrophotometer) manufactured by JASCO Corporation)

Comparative examples and examples with reference to the first invention will be shown.

Comparative Examples 1 and 2

According to formulations shown in Table 1, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at the temperature at discharge of 80° C. for 5 minutes (step F) to obtain an unvulcanized rubber composition. After that, tires for test were produced in the same manner as in Examples and the following evaluations were conducted. The results are shown in Table 1.

Examples 1 to 8 and Comparative Examples 3 and 4

According to formulations shown in Table 1, the chemicals shown in the step X1 were kneaded with a 1.7 L Banbury mixer at the temperature at discharge of 150° C. for 5.0 minutes (step X1). Then, the kneaded product of the step X1 and chemicals shown in the step X2 were kneaded with a 1.7 L Banbury mixer at the temperature at discharge of 150° C. for 5.0 minutes (step X2). After that, the kneaded product of the step X2 and the chemicals shown in the step F were kneaded using an open roll at the temperature at discharge of 80° C. for 5 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 1.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 1 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 1 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 1 was reduced for 1 mm)×100

<Steering Stability Test>

The tires for test were loaded on the whole wheels of a real vehicle for test (domestically produced FF vehicle, displacement: 2000 cc), followed by meandering. During the meandering, the stability of control of steering was evaluated by a sensorial evaluation of a test driver and the results are shown by index, assuming the steering stability of Comparative Example 1 as 100. The higher the index is, the more excellent the steering stability is.

<Processability Test>

The easiness of processing of unvulcanized rubber compositions and the shape of processed products were checked by a visual inspection and evaluated by the following criteria.

4: easily processed and shape of sheet is smooth and very satisfactory

3: processed without any problem and shape of sheet is satisfactory

2: processing is possible but there are concavity and convexity on sheet cloth, which is inferior 1: condition of cloth is bad and sheet processing is impossible

TABLE 1

|  | COMPARATIVE EXAMPLES | |
| --- | --- | --- |
|  | 1 | 2 |
| Compounded amount (part by mass) | | |
| Step X | | |
| NR | — | 15 |
| SBR 1 | 70 | 40 |
| SBR 2 | — | 20 |
| BR 1 | 30 | — |
| BR 2 | — | 15 |
| Silica 1 | 60 | 60 |
| Silica 2 | — | — |
| Carbon black 1 | 5 | 5 |
| Oil 1 | 5 | 5 |
| Stearic acid | 2 | 2 |
| Wax | 2 | 2 |
| Coupling agent 1 | 4.8 | 4.8 |
| Coupling agent 2 | — | — |
| Silica 1 | — | — |
| Silica 2 | — | — |
| Carbon black 1 | — | — |
| Coupling agent 1 | — | — |
| Coupling agent 2 | — | — |
| Anti-aging agent | 2 | 2 |
| Zinc oxide | 2 | 2 |
| Step F | | |

TABLE 1-continued

|  |  |  |
|---|---|---|
| Sulfur | 1.5 | 1.5 |
| Vulcanization accelerator 1 | 1.5 | 1.5 |
| Vulcanization accelerator 2 | 1 | 1 |
| Evaluation |  |  |
| Fuel efficiency | 100 | 105 |
| Abrasion resistance | 100 | 103 |
| Steering stability | 100 | 101 |
| Processability | 3 | 2 |

|  | EXAMPLE |  |  |  |  |  |  |  | COM. EX. |  |
|---|---|---|---|---|---|---|---|---|---|---|
|  | 1 | 2 | 3 | 4 | 5 | 6 | 7 | 8 | 3 | 4 |
| Compounded amount (part by mass) |  |  |  |  |  |  |  |  |  |  |
| Step X1 |  |  |  |  |  |  |  |  |  |  |
| NR | — | 15 | — | — | — | — | — | — | — | — |
| SBR 1 | 70 | 40 | 70 | 70 | 70 | 70 | 70 | 70 | 70 | 70 |
| SBR 2 | — | 20 | — | — | — | — | — | — | — | — |
| BR 1 | 30 | — | 30 | 30 | 30 | 30 | 30 | 30 | 30 | 30 |
| BR 2 | — | 15 | — | — | — | — | — | — | — | — |
| Silica 1 | 45 | 45 | — | 22.5 | 45 | 45 | 15 | 45 | 45 | 45 |
| Silica 2 | — | — | 45 | — | — | — | — | — | — | — |
| Carbon black 1 | 5 | 5 | 5 | 5 | 5 | 5 | 5 | 3 | 5 | 5 |
| Oil 1 | 5 | 5 | 5 | 5 | 5 | 5 | 5 | 5 | 5 | 5 |
| Stearic acid | 2 | 2 | 2 | 2 | 2 | 2 | 2 | 2 | 2 | 2 |
| Wax | 2 | 2 | 2 | 2 | 2 | 2 | 2 | 2 | 2 | 2 |
| Coupling agent 1 | 3.6 | 3.6 | 3.6 | 1.8 | 7.2 | 6.75 | 1.2 | 3.6 | — | — |
| Coupling agent 2 | — | — | — | — | — | — | — | — | 3.6 | 3.6 |
| Step X2 |  |  |  |  |  |  |  |  |  |  |
| Silica 1 | 15 | 15 | — | 7.5 | 15 | 15 | 45 | 15 | 15 | 15 |
| Silica 2 | — | — | 15 | — | — | — | — | — | — | — |
| Carbon black 1 | — | — | — | — | — | — | — | 2 | — | — |
| Coupling agent 1 | 1.2 | 1.2 | 1.2 | 0.6 | 0.3 | 4.5 | 3.6 | 1.2 | 1.2 | — |
| Coupling agent 2 | — | — | — | — | — | — | — | — | — | 1.2 |
| Anti-aging agent | 2 | 2 | 2 | 2 | 2 | 2 | 2 | 2 | 2 | 2 |
| Zinc oxide | 2 | 2 | 2 | 2 | 2 | 2 | 2 | 2 | 2 | 2 |
| Step F |  |  |  |  |  |  |  |  |  |  |
| Sulfur | 1.5 | 1.5 | 1.5 | 1.5 | 1.5 | 1.5 | 1.5 | 1.5 | 1.5 | 1.5 |
| Vulcanization accelerator 1 | 1.5 | 1.5 | 1.5 | 1.5 | 1.5 | 1.5 | 1.5 | 1.5 | 1.5 | 1.5 |
| Vulcanization accelerator 2 | 1 | 1 | 1 | 1 | 1 | 1 | 1 | 1 | 1 | 1 |
| Evaluation |  |  |  |  |  |  |  |  |  |  |
| Fuel efficiency | 105 | 112 | 108 | 120 | 104 | 105 | 102 | 105 | 98 | 97 |
| Abrasion resistance | 103 | 107 | 98 | 92 | 102 | 100 | 101 | 103 | 100 | 99 |
| Steering stability | 102 | 105 | 103 | 95 | 102 | 102 | 101 | 102 | 102 | 102 |
| Processability | 4 | 4 | 4 | 4 | 4 | 3 | 4 | 4 | 2 | 2 |

From the results of Table 1, it can be seen that processability, fuel efficiency and abrasion resistance can be improved in a good balance by producing a rubber composition for tire comprising a specified rubber component (A-1), silica 1 (B1-1), silica 2 (B2-1), carbon black (C-1), a specified coupling agent (D-1), vulcanizer (E1-1) and a vulcanization accelerator (E2-1) by a specified production method.

Comparative examples and examples with reference to the second invention will be shown.

Comparative Examples 5 to 7

According to formulations shown in Table 2, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at the temperature at discharge of 80° C. for 3 minutes (step F) to obtain an unvulcanized rubber composition. After that, tires for test were produced in the same manner as in Examples and the following evaluations were conducted. The results are shown in Table 2.

Examples 9 to 14 and Comparative Example 8

According to formulations shown in Table 2, the chemicals shown in the step X1 were kneaded with a 1.7 L Banbury mixer at the temperature at discharge of 150° C. for 5.0 minutes (step X1). After that, the kneaded product was held for one minute within the mixer such that the temperature at discharge became 160° C. Then, the kneaded product of the step X1 and chemicals shown in the step X2 were kneaded with a 1.7 L Banbury mixer at the temperature of not lower than 140° C. for 30 seconds and further kneading at the temperature at discharge of 150° C. for 3 minutes (step X2). After that, the kneaded product of the step X2 and the chemicals shown in the step F were kneaded using an open roll at the temperature at discharge of 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 2.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 5 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 5 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 5 was reduced for 1 mm)×100

<Wet Grip Performance Test>

On the wet road surface, a braking distance from an initial speed of 100 km/h was measured. The results are shown by index in accordance with the following formula, assuming the result of Comparative Example 5 as 100. The larger the index is, the more excellent the wet grip performance is.

(Index of wet grip performance)=(Braking distance of Comparative Example 5)/(braking distance of each Example)×100

<Steering Stability Test>

The tires for test were loaded on the whole wheels of a real vehicle for test (domestically produced FF vehicle, displacement: 2000 cc), followed by meandering. During the meandering, the stability of control of steering was evaluated by a sensorial evaluation of a test driver and the results are shown by index, assuming the steering stability of Comparative Example 5 as 100. The higher the index is, the more excellent the steering stability is.

TABLE 2

| | COMPARATIVE EXAMPLES | | |
|---|---|---|---|
| | 5 | 6 | 7 |
| Compounded amount (part by mass) Step X | | | |
| SBR 1 | 70 | — | — |
| SBR 3 | — | 70 | 70 |
| BR 1 | 30 | — | — |
| BR 3 | — | 30 | 30 |
| Silica 1 | 45 | 45 | 45 |
| Silica 2 | 15 | 15 | 15 |
| Carbon black 1 | 5 | 5 | 5 |
| Oil 2 | 5 | 5 | 5 |
| Stearic acid | 2 | 2 | 2 |
| Wax | 2 | 2 | 2 |

TABLE 2-continued

| | | | |
|---|---|---|---|
| Surfactant | — | — | 1 |
| Vulcanization accelerator 2 | — | — | 1 |
| Coupling agent 1 | 4.8 | 4.8 | 4.8 |
| Coupling agent 2 | — | — | — |
| Silica 2 | — | — | — |
| Coupling agent 1 | — | — | — |
| Coupling agent 2 | — | — | — |
| Anti-aging agent | 2 | 2 | 2 |
| Zinc oxide Step F | 2 | 2 | 2 |
| Sulfur | 1.5 | 1.5 | 1.5 |
| Vulcanization accelerator 1 | 1.5 | 1.5 | 1.5 |
| Vulcanization accelerator 2 | 1.5 | 1.5 | 0.5 |
| Evaluation | | | |
| Fuel efficiency | 100 | 105 | 105 |
| Abrasion resistance | 100 | 95 | 95 |
| Wet grip performance | 100 | 100 | 95 |
| Steering stability | 100 | 95 | 100 |

| | EXAMPLES | | | | | | COM. EX. |
|---|---|---|---|---|---|---|---|
| | 9 | 10 | 11 | 12 | 13 | 14 | 8 |
| Compounded amount (part by mass) Step X1 | | | | | | | |
| SBR 1 | 70 | — | — | — | — | — | — |
| SBR 3 | — | 70 | 70 | 70 | 70 | 70 | 70 |
| BR 1 | 30 | — | — | — | — | — | — |
| BR 3 | — | 30 | 30 | 30 | 30 | 30 | 30 |
| Silica 1 | 45 | 45 | 45 | 45 | 15 | 45 | 45 |
| Silica 2 | — | — | — | — | — | — | — |
| Carbon black 1 | 5 | 5 | 5 | 5 | 5 | 5 | 5 |
| Oil 2 | 5 | 5 | 5 | 5 | 5 | 5 | 5 |
| Stearic acid | 2 | 2 | 2 | 2 | 2 | 2 | 2 |
| Wax | 2 | 2 | 2 | 2 | 2 | 2 | 2 |
| Surfactant | — | — | — | 1 | — | 2 | 1 |
| Vulcanization accelerator 2 | — | — | 1 | 1 | — | 1 | 1 |
| Coupling agent 1 | 3.6 | 3.6 | 3.6 | 3.6 | 1.2 | 3.6 | — |
| Coupling agent 2 | — | — | — | — | — | — | 3.6 |
| Step X2 | | | | | | | |
| Silica 2 | 15 | 15 | 15 | 15 | 45 | 15 | 15 |
| Coupling agent 1 | 1.2 | 1.2 | 1.2 | 1.2 | 3.6 | 1.2 | — |
| Coupling agent 2 | — | — | — | — | — | — | 1.2 |
| Anti-aging agent | 2 | 2 | 2 | 2 | 2 | 2 | 2 |
| Zinc oxide Step F | 2 | 2 | 2 | 2 | 2 | 2 | 2 |
| Sulfur | 1.5 | 1.5 | 1.5 | 1.5 | 1.5 | 1.5 | 1.5 |
| Vulcanization accelerator 1 | 1.5 | 1.5 | 1.5 | 1.5 | 1.5 | 1.5 | 1.5 |
| Vulcanization accelerator 2 | 1.5 | 1.5 | 0.5 | 0.5 | 1.5 | 0.5 | 0.5 |
| Evaluation | | | | | | | |
| Fuel efficiency | 105 | 115 | 115 | 120 | 128 | 121 | 95 |
| Abrasion resistance | 105 | 100 | 100 | 105 | 102 | 104 | 95 |

TABLE 2-continued

| | | | | | | | |
|---|---|---|---|---|---|---|---|
| Wet grip performance | 100 | 100 | 100 | 100 | 102 | 100 | 100 |
| Steering stability | 105 | 100 | 105 | 105 | 109 | 100 | 95 |

From the results of Table 2, it can be seen that fuel efficiency, abrasion resistance and wet grip performance can be improved in a good balance by producing a rubber composition for tire comprising a specified rubber component (A-2), silica 1 (B1-2), silica 2 (B2-2), carbon black (C-2), a specified coupling agent (D-2), a vulcanizer (E1-2) and a vulcanization accelerator (E2-2) by a specified production method.

Comparative examples and examples with reference to the third invention will be shown.

Comparative Examples 9 to 11

According to formulations shown in Table 3, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at about 80° C. for 3 minutes (step F) to obtain an unvulcanized rubber composition. After that, tires for test were produced in the same manner as in Examples and the following evaluations were conducted. The results are shown in Table 3.

Examples 15 to 20 and Comparative Example 12

According to formulations shown in Table 3, the chemicals shown in the step X1 were kneaded with a 1.7 L Banbury mixer at the temperature at discharge of 150° C. for 5.0 minutes (step X1). After that, the kneaded product was held for one minute within the mixer such that the temperature at discharge became 160° C. Then, the kneaded product of the step X1 and chemicals shown in the step X2 were kneaded with a 1.7 L Banbury mixer at the temperature of not lower than 140° C. for 30 seconds and further kneaded at the temperature at discharge of 145° C. for 3 minutes (step X2). Then, the kneaded product of the step X2 and the chemicals shown in the step F were kneaded using an open roll at about 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 3.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 9 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 9 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 9 was reduced for 1 mm)×100

<Wet Grip Performance Test>

On the wet road surface, a braking distance from an initial speed of 100 km/h was measured. The results are shown by index in accordance with the following formula, assuming the result of Comparative Example 9 as 100. The larger the index is, the more excellent the wet grip performance is.

(Index of wet grip performance)=(Braking distance of Comparative Example 9)/(braking distance of each Example)×100

<Steering Stability Test>

The tires for test were loaded on the whole wheels of a real vehicle for test (domestically produced FF vehicle, displacement: 2000 cc), followed by meandering. During the meandering, the stability of control of steering was evaluated by a sensorial evaluation of a test driver and the results are shown by index, assuming the steering stability of Comparative Example 9 as 100. The larger the index is, the more excellent the steering stability is.

TABLE 3

| | COMPARATIVE EXAMPLES | | |
|---|---|---|---|
| | 9 | 10 | 11 |
| Compounded amount (part by mass) | | | |
| Step X | | | |
| SBR 1 | 65 | — | — |
| SBR 3 | — | 65 | 65 |
| BR 1 | 35 | — | — |
| BR 3 | — | 35 | 35 |
| Silica 1 | 60 | 60 | 60 |
| Carbon black 1 | 5 | 5 | 5 |
| Oil 2 | 5 | 5 | 5 |
| Stearic acid | 2 | 2 | 2 |
| Wax | 2 | 2 | 2 |
| Surfactant | — | — | 1 |
| Vulcanization accelerator 2 | — | — | 1 |
| Coupling agent 1 | 3.2 | 3.2 | 3.2 |
| Coupling agent 3 | 1.6 | 1.6 | 1.6 |
| SBR 1 | — | — | — |
| SBR 3 | — | — | — |
| Silica 1 | — | — | — |
| Coupling agent 1 | — | — | — |
| Coupling agent 3 | — | — | — |
| Anti-aging agent | 2 | 2 | 2 |
| Zinc oxide | 2 | 2 | 2 |
| Step F | | | |
| Sulfur | 1.5 | 1.5 | 1.5 |
| Vulcanization | 1.5 | 1.5 | 1.5 |

TABLE 3-continued

| | | | |
|---|---|---|---|
| accelerator 1 | | | |
| Vulcanization accelerator 2 | 1.5 | 1.5 | 0.5 |
| Evaluation | | | |
| Fuel efficiency | 100 | 105 | 108 |
| Abrasion resistance | 100 | 97 | 98 |
| Wet grip performance | 100 | 95 | 97 |
| Steering stability | 100 | 98 | 95 |

| | EXAMPLES | | | | | | COM. EX. |
|---|---|---|---|---|---|---|---|
| | 15 | 16 | 17 | 18 | 19 | 20 | 12 |
| Compounded amount (part by mass) Step X1 | | | | | | | |
| SBR 1 | — | — | — | — | — | — | — |
| SBR 3 | — | — | — | — | — | — | — |
| BR 1 | 35 | — | — | — | — | — | — |
| BR 3 | — | 35 | 35 | 35 | 35 | 35 | 35 |
| Silica 1 | 40 | 40 | 40 | 40 | 20 | 40 | 40 |
| Carbon black 1 | 5 | 5 | 5 | 5 | 5 | 5 | 5 |
| Oil 2 | 5 | 5 | 5 | 5 | 5 | 5 | 5 |
| Stearic acid | 2 | 2 | 2 | 2 | 2 | 2 | 2 |
| Wax | 2 | 2 | 2 | 2 | 2 | 2 | 2 |
| Surfactant | — | — | — | 1 | — | 2 | 1 |
| Vulcanization accelerator 2 | — | — | 1 | 1 | — | 1 | 1 |
| Coupling agent 1 | 3.2 | 3.2 | 3.2 | 3.2 | 1.6 | 3.2 | — |
| Coupling agent 3 | — | — | — | — | — | — | 3.2 |
| Step X2 | | | | | | | |
| SBR 1 | 65 | — | — | — | — | — | — |
| SBR 3 | — | 65 | 65 | 65 | 65 | 65 | 65 |
| Silica 1 | 20 | 20 | 20 | 20 | 40 | 20 | 20 |
| Coupling agent 1 | — | — | — | — | — | — | — |
| Coupling agent 3 | 1.6 | 1.6 | 1.6 | 1.6 | 3.2 | 1.6 | 1.6 |
| Anti-aging agent | 2 | 2 | 2 | 2 | 2 | 2 | 2 |
| Zinc oxide | 2 | 2 | 2 | 2 | 2 | 2 | 2 |
| Step F | | | | | | | |
| Sulfur | 1.5 | 1.5 | 1.5 | 1.5 | 1.5 | 1.5 | 1.5 |
| Vulcanization accelerator 1 | 1.5 | 1.5 | 1.5 | 1.5 | 1.5 | 1.5 | 1.5 |
| Vulcanization accelerator 2 | 1.5 | 1.5 | 0.5 | 0.5 | 1.5 | 0.5 | 0.5 |
| Evaluation | | | | | | | |
| Fuel efficiency | 105 | 113 | 116 | 119 | 109 | 122 | 96 |
| Abrasion resistance | 108 | 107 | 110 | 113 | 103 | 111 | 98 |
| Wet grip performance | 104 | 103 | 107 | 108 | 101 | 109 | 100 |
| Steering stability | 105 | 105 | 106 | 105 | 103 | 105 | 97 |

From the results of Table 3, it can be seen that fuel efficiency, abrasion resistance and wet grip performance can be improved in a good balance by producing a rubber composition for tire comprising a butadiene rubber (A1-3), a styrene butadiene rubber (A2-3), silica (B-3), carbon black (C-3), a specified coupling agent (D1-3), a coupling agent having a sulfide group (D2-3), a vulcanizer (E1-3) and a vulcanization accelerator (E2-3) by a specified production method.

Comparative examples and examples with reference to the fourth invention will be shown.

Comparative Examples 13 to 15

According to formulations shown in Table 4, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at about 80° C. for 3 minutes (step F) to obtain an unvulcanized rubber composition. After that, tires for test were produced in the same manner as in Examples and the following evaluations were conducted. The results are shown in Table 4.

Examples 21 to 26 and Comparative Example 16

According to formulations shown in Table 4, the chemicals shown in the step X1 were kneaded with a 1.7 L Banbury mixer at the temperature at discharge of 150° C. for 5.0 minutes (step X1). After that, the kneaded product was held for one minute within the mixer such that the temperature at discharge became 160° C. Then, the kneaded product of the step X1 and chemicals shown in the step X2 were kneaded with a 1.7 L Banbury mixer at the temperature of not lower than 140° C. for 30 seconds and further kneaded at the temperature at discharge of 145° C. for 3 minutes (step X2). Then, the kneaded product of the step X2 and the chemicals shown in the step F were kneaded using an open roll at about 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 4.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 13 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 13 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 13 was reduced for 1 mm)×100

<Wet Grip Performance Test>

On the wet road surface, a braking distance from an initial speed of 100 km/h was measured. The results are shown by index in accordance with the following formula, assuming the result of Comparative Example 13 as 100. The larger the index is, the more excellent the wet grip performance is.

(Index of wet grip performance)=(Braking distance of Comparative Example 13)/(braking distance of each Example)×100

<Steering Stability Test>

The tires for test were loaded on the whole wheels of a real vehicle for test (domestically produced FF vehicle, displacement: 2000 cc), followed by meandering. During the meandering, the stability of control of steering was evaluated by a sensorial evaluation of a test driver and the results are shown by index, assuming the steering stability of Comparative Example 13 as 100. The higher the score is, the more excellent the steering stability is.

TABLE 4

| | COMPARATIVE EXAMPLES | | |
|---|---|---|---|
| | 13 | 14 | 15 |
| Compounded amount (part by mass) Step X | | | |
| NR | 15 | 15 | 15 |
| SBR 1 | 70 | — | — |
| SBR 3 | — | 70 | 70 |
| BR 1 | 15 | — | — |
| BR 3 | — | 15 | 15 |
| Silica 1 | 45 | 45 | 45 |
| Silica 2 | — | — | — |
| Carbon black 1 | 5 | 5 | 5 |
| Oil 2 | 5 | 5 | 5 |
| Stearic acid | 2 | 2 | 2 |
| Wax | 2 | 2 | 2 |
| Surfactant | — | — | 1 |
| Vulcanization accelerator 2 | — | — | 1 |
| Coupling agent 1 | 3.6 | 3.6 | 3.6 |
| Coupling agent 3 | 1.2 | 1.2 | 1.2 |
| Silica 2 | — | — | — |
| Coupling agent 1 | — | — | — |
| Coupling agent 3 | — | — | — |
| Anti-aging agent | 2 | 2 | 2 |
| Zinc oxide | 2 | 2 | 2 |
| Step F | | | |
| Sulfur | 1.5 | 1.5 | 1.5 |
| Vulcanization accelerator 1 | 1.5 | 1.5 | 1.5 |
| Vulcanization accelerator 2 | 1.5 | 1.5 | 0.5 |
| Evaluation | | | |
| Fuel efficiency | 100 | 102 | 103 |
| Abrasion resistance | 100 | 94 | 98 |
| Wet grip performance | 100 | 100 | 97 |
| Steering stability | 100 | 96 | 97 |

TABLE 4-continued

| | EXAMPLES | | | | | | COM. EX. |
|---|---|---|---|---|---|---|---|
| | 21 | 22 | 23 | 24 | 25 | 26 | 16 |
| Compounded amount (part by mass) Step X1 | | | | | | | |
| NR | 15 | 15 | 15 | 15 | 15 | 15 | 15 |
| SBR 1 | 70 | — | — | — | — | — | — |
| SBR 3 | — | 70 | 70 | 70 | 70 | 70 | 70 |
| BR 1 | 15 | — | — | — | — | — | — |
| BR 3 | — | 15 | 15 | 15 | 15 | 15 | 15 |
| Silica 1 | 45 | 45 | 45 | 45 | 15 | 45 | 45 |
| Silica 2 | — | — | — | — | — | — | — |
| Carbon black 1 | 5 | 5 | 5 | 5 | 5 | 5 | 5 |
| Oil 2 | 5 | 5 | 5 | 5 | 5 | 5 | 5 |
| Stearic acid | 2 | 2 | 2 | 2 | 2 | 2 | 2 |
| Wax | 2 | 2 | 2 | 2 | 2 | 2 | 2 |
| Surfactant | — | — | — | 1 | — | 2 | 1 |
| Vulcanization accelerator 2 | — | — | 1 | 1 | — | 1 | 1 |
| Coupling agent 1 | 3.6 | 3.6 | 3.6 | 3.6 | 1.2 | 3.6 | — |
| Coupling agent 3 | — | — | — | — | — | — | 3.6 |
| Step X2 | | | | | | | |
| Silica 2 | 15 | 15 | 15 | 15 | 45 | 15 | 15 |
| Coupling agent 1 | — | — | — | — | — | — | — |
| Coupling agent 3 | 1.2 | 1.2 | 1.2 | 1.2 | 3.6 | 1.2 | 1.2 |
| Anti-aging agent | 2 | 2 | 2 | 2 | 2 | 2 | 2 |
| Zinc oxide | 2 | 2 | 2 | 2 | 2 | 2 | 2 |
| Step F | | | | | | | |
| Sulfur | 1.5 | 1.5 | 1.5 | 1.5 | 1.5 | 1.5 | 1.5 |
| Vulcanization accelerator 1 | 1.5 | 1.5 | 1.5 | 1.5 | 1.5 | 1.5 | 1.5 |
| Vulcanization accelerator 2 | 1.5 | 1.5 | 0.5 | 0.5 | 1.5 | 0.5 | 0.5 |
| Evaluation | | | | | | | |
| Fuel efficiency | 104 | 109 | 116 | 118 | 125 | 120 | 97 |
| Abrasion resistance | 103 | 107 | 114 | 117 | 104 | 115 | 97 |
| Wet grip performance | 101 | 102 | 105 | 106 | 102 | 106 | 94 |
| Steering stability | 101 | 102 | 104 | 104 | 102 | 104 | 96 |

From the results of Table 4, it can be seen that fuel efficiency, abrasion resistance and wet grip performance can be improved in a good balance by producing a rubber composition for tire comprising a specified rubber component (A-4), silica 1 (B1-4), silica 2 (B2-4), carbon black (C-4), a specified coupling agent (D1-4), a coupling agent having a sulfide group (D2-4), a vulcanizer (E1-4) and a vulcanization accelerator (E2-4) by a specified production method.

Comparative examples and examples with reference to the fifth invention will be shown.

Comparative Examples 17 to 19

According to formulations shown in Table 5, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at about 80° C. for 3 minutes (step F) to obtain an unvulcanized rubber composition. After that, tires for test were produced in the same manner as in Examples and the following evaluations were conducted. The results are shown in Table 5.

Examples 27 to 32 and Comparative Example 20

According to formulations shown in Table 5, the chemicals shown in the step X1 were kneaded with a 1.7 L Banbury mixer at the temperature at discharge of 150° C. for 5.0 minutes (step X1). After that, the kneaded product was held for one minute within the mixer such that the temperature at discharge became 160° C. Then, the kneaded product of the step X1 and chemicals shown in the step X2 were kneaded with a 1.7 L Banbury mixer at the temperature of not lower than 140° C. for 30 seconds and further kneaded at the temperature at discharge of 145° C. for 3 minutes (step X2). Then, the kneaded product of the step X2 and the chemicals shown in the step F were kneaded using an open roll at about 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 5.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 17 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 17 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 17 was reduced for 1 mm)×100

<Wet Grip Performance Test>

On the wet road surface, a braking distance from an initial speed of 100 km/h was measured. The results are shown by index in accordance with the following formula, assuming the result of Comparative Example 17 as 100. The larger the index is, the more excellent the wet grip performance is.

(Index of wet grip performance)=(Braking distance of Comparative Example 17)/(braking distance of each Example)×100

<Steering Stability Test>

The tires for test were loaded on the whole wheels of a real vehicle for test (domestically produced FF vehicle, displacement: 2000 cc), followed by meandering. During the meandering, the stability of control of steering was evaluated by a sensorial evaluation of a test driver and the results are shown by index, assuming the steering stability of Comparative Example 17 as 100. The larger the index is, the more excellent the steering stability is.

TABLE 5

| | COMPARATIVE EXAMPLES | | |
|---|---|---|---|
| | 17 | 18 | 19 |
| Compounded amount (part by mass) Step X | | | |
| NR | 40 | 40 | 40 |
| BR 1 | 60 | — | — |
| BR 3 | — | 60 | 60 |
| Silica 1 | 100 | 100 | 100 |
| Carbon black 1 | 5 | 5 | 5 |
| Oil 2 | 30 | 30 | 30 |
| Stearic acid | 2 | 2 | 2 |
| Wax | 2 | 2 | 2 |
| Surfactant | — | — | 1 |
| Vulcanization accelerator 2 | — | — | 1 |
| Coupling agent 1 | 6.4 | 6.4 | 6.4 |
| Coupling agent 3 | 1.6 | 1.6 | 1.6 |
| NR | — | — | — |
| Silica 1 | — | — | — |
| Coupling agent 1 | — | — | — |
| Coupling agent 3 | — | — | — |
| Anti-aging agent | 2 | 2 | 2 |
| Zinc oxide | 2 | 2 | 2 |
| Step F | | | |
| Sulfur | 1 | 1 | 1 |
| Vulcanization accelerator 1 | 1.5 | 1.5 | 1.5 |
| Vulcanization accelerator 2 | 1.5 | 1.5 | 0.5 |
| Evaluation | | | |
| Fuel efficiency | 100 | 105 | 108 |
| Abrasion resistance | 100 | 95 | 103 |
| Wet grip performance | 100 | 95 | 103 |
| Steering stability | 100 | 95 | 103 |

| | EXAMPLES | | | | | | COM. EX. |
|---|---|---|---|---|---|---|---|
| | 27 | 28 | 29 | 30 | 31 | 32 | 20 |
| Compounded amount (part by mass) Step X1 | | | | | | | |
| NR | — | — | — | — | — | — | — |
| BR 1 | 60 | — | — | — | — | — | — |
| BR 3 | — | 60 | 60 | 60 | 60 | 60 | 60 |
| Silica 1 | 80 | 80 | 80 | 80 | 20 | 80 | 80 |
| Carbon black 1 | 5 | 5 | 5 | 5 | 5 | 5 | 5 |
| Oil 2 | 30 | 30 | 30 | 30 | 5 | 30 | 30 |
| Stearic acid | 2 | 2 | 2 | 2 | 2 | 2 | 2 |
| Wax | 2 | 2 | 2 | 2 | 2 | 2 | 2 |
| Surfactant | — | — | — | 1 | — | 2 | 1 |
| Vulcanization accelerator 2 | — | — | 1 | 1 | — | 1 | 1 |
| Coupling agent 1 | 6.4 | 6.4 | 6.4 | 6.4 | 1.6 | 6.4 | — |
| Coupling agent 3 | — | — | — | — | — | — | 6.4 |
| Step X2 | | | | | | | |
| NR | 40 | 40 | 40 | 40 | 40 | 40 | 40 |
| Silica 1 | 20 | 20 | 20 | 20 | 80 | 20 | 20 |
| Coupling agent 1 | — | — | — | — | — | — | — |
| Coupling agent 3 | 1.6 | 1.6 | 1.6 | 1.6 | 6.4 | 1.6 | 1.6 |
| Anti-aging agent | 2 | 2 | 2 | 2 | 2 | 2 | 2 |
| Zinc oxide | 2 | 2 | 2 | 2 | 2 | 2 | 2 |
| Step F | | | | | | | |

TABLE 5-continued

| | | | | | | | |
|---|---|---|---|---|---|---|---|
| Sulfur | 1 | 1 | 1 | 1 | 1.5 | 1.5 | 1.5 |
| Vulcanization accelerator 1 | 1.5 | 1.5 | 1.5 | 1.5 | 1.5 | 1.5 | 1.5 |
| Vulcanization accelerator 2 | 1.5 | 1.5 | 0.5 | 0.5 | 1.5 | 0.5 | 0.5 |
| Evaluation | | | | | | | |
| Fuel efficiency | 105 | 108 | 117 | 120 | 106 | 122 | 90 |
| Abrasion resistance | 102 | 108 | 114 | 119 | 105 | 116 | 95 |
| Wet grip performance | 102 | 105 | 114 | 114 | 105 | 114 | 95 |
| Steering stability | 103 | 106 | 115 | 115 | 106 | 115 | 95 |

From the results of Table 5, it can be seen that fuel efficiency, abrasion resistance and wet grip performance can be improved in a good balance by producing a rubber composition for tire comprising a butadiene rubber (A1-5), an isoprene based rubber (A2-5), silica (B-5), carbon black (C-5), a specified coupling agent (D1-5), a coupling agent having a sulfide group (D2-5), a vulcanizer (E1-5) and a vulcanization accelerator (E2-5) by a specified production method.

Comparative examples and examples with reference to the sixth invention will be shown.

Comparative Examples 21 to 23

According to formulations shown in Table 6, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at about 80° C. for 3 minutes (step F) to obtain an unvulcanized rubber composition. After that, tires for test were produced in the same manner as in Examples and the following evaluations were conducted. The results are shown in Table 6.

Examples 33 to 38 and Comparative Example 24

According to formulations shown in Table 6, the chemicals shown in the step X1 were kneaded with a 1.7 L Banbury mixer at the temperature at discharge of 150° C. for 5.0 minutes (step X1). Then, the kneaded product of the step X1 and chemicals shown in the step X2 were kneaded with a 1.7 L Banbury mixer at the temperature of not lower than 140° C. for 30 seconds and further kneaded at the temperature at discharge of 150° C. for 3 minutes (step X2). After that, the kneaded product was held for one minute within the mixer such that the temperature at discharge became 155° C. Then, the kneaded product of the step X2 and the chemicals shown in the step F were kneaded using an open roll at about 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 6.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 21 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 21 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 21 was reduced for 1 mm)×100

<Wet Grip Performance Test>

On the wet road surface, a braking distance from an initial speed of 100 km/h was measured. The results are shown by index in accordance with the following formula, assuming the result of Comparative Example 21 as 100. The larger the index is, the more excellent the wet grip performance is.

(Index of wet grip performance)=(Braking distance of Comparative Example 21)/(braking distance of each Example)×100

<Steering Stability Test>

The tires for test were loaded on the whole wheels of a real vehicle for test (domestically produced FF vehicle, displacement: 2000 cc), followed by meandering. During the meandering, the stability of control of steering was evaluated by a sensorial evaluation of a test driver and the results are shown by index, assuming the steering stability of Comparative Example 21 as 100. The larger the index is, the more excellent the steering stability is.

TABLE 6

| | COMPARATIVE EXAMPLES | | |
|---|---|---|---|
| | 21 | 22 | 23 |
| Compounded amount (part by mass) Step X | | | |
| SBR 1 | 65 | — | — |
| SBR 3 | — | 65 | 65 |
| BR 1 | 35 | — | — |
| BR 3 | — | 35 | 35 |
| Silica 1 | 60 | 60 | 60 |
| Carbon black 1 | 5 | 5 | 5 |
| Oil 2 | 5 | 5 | 5 |
| Stearic acid | 2 | 2 | 2 |
| Wax | 2 | 2 | 2 |
| Surfactant | — | — | 1 |
| Vulcanization accelerator 2 | — | — | 1 |
| Coupling agent 1 | 4.8 | 4.8 | 4.8 |
| Coupling agent 2 | — | — | — |
| SBR 1 | — | — | — |
| SBR 3 | — | — | — |
| Silica 1 | — | — | — |
| Coupling agent 1 | — | — | — |
| Coupling agent 2 | — | — | — |
| Anti-aging agent | 2 | 2 | 2 |

TABLE 6-continued

| | | | |
|---|---|---|---|
| Zinc oxide | 2 | 2 | 2 |
| Step F | | | |
| Sulfur | 1.5 | 1.5 | 1.5 |
| Vulcanization accelerator 1 | 1.5 | 1.5 | 1.5 |
| Vulcanization accelerator 2 | 1.5 | 1.5 | 0.5 |
| Evaluation | | | |
| Fuel efficiency | 100 | 111 | 114 |
| Abrasion resistance | 100 | 90 | 89 |
| Wet grip performance | 100 | 101 | 100 |
| Steering stability | 100 | 91 | 93 |

| | EXAMPLES | | | | | | COM. EX. |
|---|---|---|---|---|---|---|---|
| | 33 | 34 | 35 | 36 | 37 | 38 | 24 |
| Compounded amount (part by mass) Step X1 | | | | | | | |
| SBR 1 | — | — | — | — | — | — | — |
| SBR 3 | — | — | — | — | — | — | — |
| BR 1 | 35 | — | — | — | — | — | — |
| BR 3 | — | 35 | 35 | 35 | 35 | 35 | 35 |
| Silica 1 | 40 | 40 | 40 | 40 | 20 | 45 | 40 |
| Carbon black 1 | 5 | 5 | 5 | 5 | 5 | 5 | 5 |
| Oil 2 | 5 | 5 | 5 | 5 | 5 | 5 | 5 |
| Stearic acid | 2 | 2 | 2 | 2 | 2 | 2 | 2 |
| Wax | 2 | 2 | 2 | 2 | 2 | 2 | 2 |
| Surfactant | — | — | — | 1 | — | 2 | 1 |
| Vulcanization accelerator 2 | — | — | 1 | 1 | — | 1 | 1 |
| Coupling agent 1 | 3.2 | 3.2 | 3.2 | 3.2 | 1.6 | 3.6 | — |
| Coupling agent 2 | — | — | — | — | — | — | 3.2 |
| Step X2 | | | | | | | |
| SBR 1 | 65 | — | — | — | — | — | — |
| SBR 3 | — | 65 | 65 | 65 | 40 | 65 | 65 |
| Silica 1 | 20 | 20 | 20 | 20 | 20 | 20 | 20 |
| Coupling agent 1 | 1.6 | 1.6 | 1.6 | 1.6 | 3.2 | 1.2 | — |
| Coupling agent 2 | — | — | — | — | — | — | 1.6 |
| Anti-aging agent | 2 | 2 | 2 | 2 | 2 | 2 | 2 |
| Zinc oxide | 2 | 2 | 2 | 2 | 2 | 2 | 2 |
| Step F | | | | | | | |
| Sulfur | 1.5 | 1.5 | 1.5 | 1.5 | 1.5 | 1.5 | 1.5 |
| Vulcanization accelerator 1 | 1.5 | 1.5 | 1.5 | 1.5 | 1.5 | 1.5 | 1.5 |
| Vulcanization accelerator 2 | 1.5 | 1.5 | 0.5 | 0.5 | 0.5 | 0.5 | 0.5 |
| Evaluation | | | | | | | |
| Fuel efficiency | 121 | 130 | 137 | 141 | 125 | 130 | 90 |
| Abrasion resistance | 118 | 117 | 116 | 120 | 113 | 124 | 98 |
| Wet grip performance | 117 | 117 | 118 | 121 | 115 | 125 | 99 |
| Steering stability | 115 | 118 | 119 | 123 | 115 | 125 | 94 |

From the results of Table 6, it can be seen that fuel efficiency, abrasion resistance and wet grip performance can be improved in a good balance by producing a rubber composition for tire comprising a butadiene rubber (A1-6), a styrene butadiene rubber (A2-6), silica (B-6), silica (B-6), carbon black (C-6), a specified coupling agent (D), a vulcanizer (E1-6) and a vulcanization accelerator (E2-6) by a specified production method.

Comparative examples and examples with reference to the seventh invention will be shown.

Comparative Examples 25 to 27

According to formulations shown in Table 7, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at about 80° C. for 3 minutes (step F) to obtain an unvulcanized rubber composition. After that, tires for test were produced in the same manner as in Examples and the following evaluations were conducted. The results are shown in Table 7.

Examples 39 to 44 and Comparative Example 28

According to formulations shown in Table 7, the chemicals shown in the step X1 were kneaded with a 1.7 L Banbury mixer at the temperature at discharge of 150° C. for 5.0 minutes (step X1). After that, the kneaded product was held for one minute within the mixer such that the temperature at discharge became 160° C. Then, the kneaded product of the step X1 and chemicals shown in the step X2 were kneaded with a 1.7 L Banbury mixer at the temperature of not lower than 140° C. for 30 seconds and further kneaded at the temperature at discharge of 145° C. for 3 minutes (step X2). Then, the kneaded product of the step X2 and the chemicals shown in the step F were kneaded using an open roll at about 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 7.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 25 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 25 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 25 was reduced for 1 mm)×100

<Wet Grip Performance Test>

On the wet road surface, a braking distance from an initial speed of 100 km/h was measured. The results are shown by index in accordance with the following formula, assuming the result of Comparative Example 25 as 100. The larger the index is, the more excellent the wet grip performance is.

(Index of wet grip performance)=(Braking distance of Comparative Example 25)/(braking distance of each Example)×100

<Electrical Conductivity Test>

A test piece of 15 cm×15 cm having a thickness of 2 mm was cut out of each of the tires for test and a volume specific resistivity was measured under conditions of an electrical voltage of 500 V, a temperature of 25° C., and a relative humidity of 50% using an electrical resistance meter R8340A manufactured by ADVANTEST Corporation. The evaluation results are shown by symbols according to the following criteria.

○: Volume specific resistivity of less than $1.0×10^7$ Ω·cm
×: Volume specific resistivity of not less than $1.0×10^7$ Ω·cm

TABLE 7

| | COMPARATIVE EXAMPLES | | |
|---|---|---|---|
| | 25 | 26 | 27 |
| Compounded amount (part by mass) Step X | | | |
| NR | 40 | 40 | 40 |
| SBR 1 | 30 | — | — |
| SBR 3 | — | 30 | 30 |
| BR 1 | 30 | — | — |
| BR 3 | — | 30 | 30 |
| Silica 1 | 75 | 75 | 75 |
| Carbon black 1 | 8 | 8 | 8 |
| Carbon black 2 | 3 | 3 | 3 |
| Oil 2 | 30 | 30 | 30 |
| Stearic acid | 2 | 2 | 2 |
| Wax | 2 | 2 | 2 |
| Surfactant | — | — | 1 |
| Vulcanization accelerator 2 | — | — | 1 |
| Coupling agent 1 | 6 | 6 | 6 |
| Coupling agent 3 | — | — | — |
| Silica 1 | — | — | — |
| Carbon black 2 | — | — | — |
| Coupling agent 1 | — | — | — |
| Coupling agent 3 | — | — | — |
| Anti-aging agent | 2 | 2 | 2 |
| Zinc oxide | 2 | 2 | 2 |
| Step F | | | |
| Sulfur | 1.5 | 1.5 | 1.5 |
| Vulcanization accelerator 1 | 1.5 | 1.5 | 1.5 |
| Vulcanization accelerator 2 | 1.5 | 1.5 | 0.5 |
| Evaluation | | | |
| Fuel efficiency | 100 | 102 | 103 |
| Abrasion resistance | 100 | 94 | 98 |
| Wet grip performance | 100 | 100 | 97 |
| Electrical conductivity | × | × | × |

| | EXAMPLES | | | | | | COM. EX. |
|---|---|---|---|---|---|---|---|
| | 39 | 40 | 41 | 42 | 43 | 44 | 28 |
| Compounded amount (part by mass) Step X1 | | | | | | | |

TABLE 7-continued

| | | | | | | | |
|---|---|---|---|---|---|---|---|
| NR | 40 | 40 | 40 | 40 | 40 | 40 | 40 |
| SBR 1 | 30 | — | — | — | — | — | — |
| SBR 3 | — | 30 | 30 | 30 | 30 | 30 | 30 |
| BR 1 | 30 | — | — | — | — | — | — |
| BR 3 | — | 30 | 30 | 30 | 30 | 30 | 30 |
| Silica 1 | 60 | 60 | 60 | 60 | 15 | 45 | 60 |
| Carbon black 1 | 8 | 8 | 8 | 8 | 5 | 5 | 8 |
| Carbon black 2 | — | — | — | — | — | — | — |
| Oil 2 | 30 | 30 | 30 | 30 | 5 | 5 | 30 |
| Stearic acid | 2 | 2 | 2 | 2 | 2 | 2 | 2 |
| Wax | 2 | 2 | 2 | 2 | 2 | 2 | 2 |
| Surfactant | — | — | — | 1 | — | 2 | 1 |
| Vulcanization accelerator 2 | — | — | 1 | 1 | — | 1 | 1 |
| Coupling agent 1 | 4.8 | 4.8 | 4.8 | 4.8 | 1.2 | 3.6 | — |
| Coupling agent 3 | — | — | — | — | — | — | 4.8 |
| Step X2 | | | | | | | |
| Silica 1 | 15 | 15 | 15 | 15 | 60 | 15 | 15 |
| Carbon black 2 | 3 | 3 | 3 | 3 | 3 | 3 | 3 |
| Coupling agent 1 | — | — | — | — | — | — | — |
| Coupling agent 3 | 1.2 | 1.2 | 1.2 | 1.2 | 4.8 | 1.2 | 1.2 |
| Anti-aging agent | 2 | 2 | 2 | 2 | 2 | 2 | 2 |
| Zinc oxide | 2 | 2 | 2 | 2 | 2 | 2 | 2 |
| Step F | | | | | | | |
| Sulfur | 1.5 | 1.5 | 1.5 | 1.5 | 1.5 | 1.5 | 1.5 |
| Vulcanization accelerator 1 | 1.5 | 1.5 | 1.5 | 1.5 | 1.5 | 1.5 | 1.5 |
| Vulcanization accelerator 2 | 1.5 | 1.5 | 0.5 | 0.5 | 1.5 | 0.5 | 0.5 |
| Evaluation | | | | | | | |
| Fuel efficiency | 104 | 109 | 116 | 118 | 107 | 120 | 97 |
| Abrasion resistance | 103 | 107 | 114 | 117 | 104 | 115 | 97 |
| Wet grip performance | 101 | 102 | 105 | 106 | 101 | 106 | 94 |
| Electrical conductivity | ○ | ○ | ○ | ○ | ○ | ○ | ○ |

From the results of Table 7, it can be seen that fuel efficiency, abrasion resistance, wet grip performance and electrical conductivity can be improved in a good balance by producing a rubber composition for tire comprising a specified rubber component (A-7), silica (B-7), carbon black 1 (C1-7), carbon black 2 (C2-7), a specified coupling agent (D1-7), a coupling agent having a sulfide group (D2-7), a vulcanizer (E1-7) and a vulcanization accelerator (E2-7) by a specified production method.

Comparative examples and examples with reference to the eighth invention will be shown.

Comparative Examples 29 to 31

According to formulations shown in Table 8, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at about 80° C. for 3 minutes (step F) to obtain an unvulcanized rubber composition. After that, tires for test were produced in the same manner as in Examples and the following evaluations were conducted. The results are shown in Table 8.

Examples 45 to 51 and Comparative Example 32

According to formulations shown in Table 8, the chemicals shown in the step X1 were kneaded with a 1.7 L Banbury mixer at the temperature at discharge of 150° C. for 5.0 minutes (step X1). After that, the kneaded product was held for one minute within the mixer such that the temperature at discharge became 160° C. Then, the kneaded product of the step X1 and chemicals shown in the step X2 were kneaded with a 1.7 L Banbury mixer at the temperature of not lower than 140° C. for 30 seconds and further kneaded at the temperature at discharge of 150° C. for 3 minutes (step X2). Then, the kneaded product of the step X2 and the chemicals shown in the step F were kneaded using an open roll at about 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 8.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 29 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 29 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 29 was reduced for 1 mm)×100

<Steering Stability Test>

The tires for test were loaded on the whole wheels of a real vehicle for test (domestically produced FF vehicle, displacement: 2000 cc), followed by meandering. During the meandering, the stability of control of steering was evaluated by a sensorial evaluation of a test driver and the results are shown by index, assuming the steering stability of Comparative Example 29 as 100. The larger the index is, the more excellent the steering stability is.

<Wet Grip Performance Test>

On the wet road surface, a braking distance from an initial speed of 100 km/h was measured. The results are shown by index in accordance with the following formula, assuming the result of Comparative Example 29 as 100. The larger the index is, the more excellent the wet grip performance is.

(Index of wet grip performance)=(Braking distance of Comparative Example 29)/(braking distance of each Example)×100

TABLE 8

|  | COMPARATIVE EXAMPLES | | |
| --- | --- | --- | --- |
|  | 29 | 30 | 31 |
| Compounded amount (part by mass) Step X | | | |
| SBR 1 | 70 | — | — |
| SBR 3 | — | 70 | 70 |
| BR 1 | 30 | — | — |
| BR 3 | — | 30 | 30 |
| Silica 1 | 60 | 60 | 60 |
| Carbon black 1 | 5 | 5 | 5 |
| Oil 2 | 5 | 5 | 5 |
| Stearic acid | 2 | 2 | 2 |
| Wax | 2 | 2 | 2 |
| Surfactant | — | — | 1 |
| Vulcanization accelerator 2 | — | — | 1 |
| Coupling agent 1 | 4.8 | 4.8 | 4.8 |
| Coupling agent 2 | — | — | — |
| Silica 1 | — | — | — |
| Vulcanization accelerator 2 | — | — | — |
| Coupling agent 1 | — | — | — |
| Coupling agent 2 | — | — | — |
| Anti-aging agent | 2 | 2 | 2 |
| Zinc oxide | 2 | 2 | 2 |
| Step F | | | |
| Sulfur | 1.5 | 1.5 | 1.5 |
| Vulcanization accelerator 1 | 1.5 | 1.5 | 1.5 |
| Vulcanization accelerator 2 | 1.5 | 1.5 | 0.5 |
| Evaluation | | | |
| Fuel efficiency | 100 | 105 | 108 |
| Abrasion resistance | 100 | 95 | 100 |
| Wet grip performance | 100 | 102 | 102 |
| Steering stability | 100 | 95 | 98 |

COM.

TABLE 8-continued

| | EXAMPLES | | | | | | | EX. |
|---|---|---|---|---|---|---|---|---|
| | 45 | 46 | 47 | 48 | 49 | 50 | 51 | 32 |
| Compounded amount (part by mass) Step X1 | | | | | | | | |
| SBR 1 | — | — | — | — | — | — | 70 | — |
| SBR 3 | 70 | 70 | 70 | 70 | 70 | 70 | — | 70 |
| BR 1 | — | — | — | — | — | — | 30 | — |
| BR 3 | 30 | 30 | 30 | 30 | 30 | 30 | — | 30 |
| Silica 1 | 45 | 45 | 45 | 45 | 15 | 45 | 45 | 45 |
| Carbon black 1 | 5 | 5 | 5 | 5 | 5 | 5 | 5 | 5 |
| Oil 2 | 5 | 5 | 5 | 5 | 5 | 5 | 5 | 5 |
| Stearic acid | 2 | 2 | 2 | 2 | 2 | 2 | 2 | 2 |
| Wax | 2 | 2 | 2 | 2 | 2 | 2 | 2 | 2 |
| Surfactant | — | 1 | — | 1 | — | 2 | — | 1 |
| Vulcanization accelerator 2 | 1 | 1 | — | — | 1 | 1 | 1 | 1 |
| Coupling agent 1 | 3.6 | 3.6 | 3.6 | 3.6 | 1.2 | 3.6 | 3.6 | — |
| Coupling agent 2 | — | — | — | — | — | — | — | 3.6 |
| Step X2 | | | | | | | | |
| Silica 1 | 15 | 15 | 15 | 15 | 45 | 15 | 15 | 15 |
| Vulcanization accelerator 2 | — | — | 1 | 1 | — | — | — | — |
| Coupling agent 1 | 1.2 | 1.2 | 1.2 | 1.2 | 3.6 | 1.2 | 1.2 | — |
| Coupling agent 2 | — | — | — | — | — | — | — | 1.2 |
| Anti-aging agent | 2 | 2 | 2 | 2 | 2 | 2 | 2 | 2 |
| Zinc oxide | 2 | 2 | 2 | 2 | 2 | 2 | 2 | 2 |
| Step F | | | | | | | | |
| Sulfur | 1.5 | 1.5 | 1.5 | 1.5 | 1.5 | 1.5 | 1.5 | 1.5 |
| Vulcanization accelerator 1 | 1.5 | 1.5 | 1.5 | 1.5 | 1.5 | 1.5 | 1.5 | 1.5 |
| Vulcanization accelerator 2 | 0.5 | 0.5 | 0.5 | 0.5 | 0.5 | 0.5 | 0.5 | 0.5 |
| Evaluation | | | | | | | | |
| Fuel efficiency | 115 | 115 | 112 | 114 | 110 | 118 | 104 | 95 |
| Abrasion resistance | 115 | 110 | 110 | 109 | 108 | 106 | 105 | 95 |
| Wet grip performance | 115 | 115 | 113 | 113 | 110 | 115 | 102 | 100 |
| Steering stability | 105 | 105 | 104 | 105 | 102 | 105 | 100 | 95 |

From the results of Table 8, it can be seen that fuel efficiency, abrasion resistance and wet grip performance can be improved in a good balance by producing a rubber composition for tire comprising a specified rubber component (A-8), silica (B-8), carbon black (C-8), a specified coupling agent (D-8), a vulcanizer (E1-8) and a vulcanization accelerator (E2-8) by a specified production method.

Comparative examples and examples with reference to the ninth invention will be shown.

Comparative Examples 33 to 35

According to formulations shown in Table 9, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at about 80° C. for 3 minutes (step F) to obtain an unvulcanized rubber composition. After that, tires for test were produced in the same manner as in Examples and the following evaluations were conducted. The results are shown in Table 9.

Examples 52 to 57 and Comparative Example 36

According to formulations shown in Table 9, the chemicals shown in the step X1 were kneaded with a 1.7 L Banbury mixer at the temperature at discharge of 150° C. for 5.0 minutes (step X1). Then, the kneaded product of the step X1 and chemicals shown in the step X2 were kneaded with a 1.7 L Banbury mixer at the temperature of not lower than 140° C. for 30 seconds and further kneaded at the temperature at discharge of 150° C. for 3 minutes (step X2). After that, the kneaded product was held for one minute within the mixer such that the temperature at discharge became 155° C. Then, the kneaded product of the step X2 and the chemicals shown in the step F were kneaded using an open roll at about 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 9.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 33 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 33 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 33 was reduced for 1 mm)×100

<Wet Grip Performance Test>

On the wet road surface, a braking distance from an initial speed of 100 km/h was measured. The results are shown by index in accordance with the following formula, assuming the result of Comparative Example 33 as 100. The larger the index is, the more excellent the wet grip performance is.

(Index of wet grip performance)=(Braking distance of Comparative Example 33)/(braking distance of each Example)×100

<On-Ice Performance Test>

The tires for test were loaded on the whole wheels of a real vehicle for test (domestically produced FF vehicle, displacement: 2000 cc). During running on ice at a speed of 30 km/h, a lock brake was applied and a distance required for stopping (distance at stop) was measured. The results are shown by index in accordance with the following formula, assuming the result of Comparative Example 33 as 100. The larger the index is, the more excellent the on-ice performance is. It is noted that the test was performed on a Hokkaido Nayoro test course of Sumitomo Rubber Industries, Ltd. and the temperature on ice was −2 to −6° C.

(Index of on-ice performance)=(Distance at stop of Comparative Example 33)/(distance at stop of each Example)×100

TABLE 9

| | COMPARATIVE EXAMPLES | | |
|---|---|---|---|
| | 33 | 34 | 35 |
| Compounded amount (part by mass) Step X | | | |
| NR | 40 | 40 | 40 |
| BR 1 | 60 | — | — |
| BR 3 | — | 60 | 60 |
| Silica 1 | 100 | 100 | 100 |
| Carbon black 1 | 5 | 5 | 5 |
| Oil 2 | 30 | 30 | 30 |
| Stearic acid | 2 | 2 | 2 |
| Wax | 2 | 2 | 2 |
| Surfactant | — | — | 1 |
| Vulcanization accelerator 2 | — | — | 1 |
| Coupling agent 1 | 8 | 8 | 8 |
| Coupling agent 2 | — | — | — |
| NR | — | — | — |
| Silica 1 | — | — | — |
| Coupling agent 1 | — | — | — |
| Coupling agent 2 | — | — | — |
| Anti-aging agent | 2 | 2 | 2 |
| Zinc oxide | 2 | 2 | 2 |
| Step F | | | |
| Sulfur | 1 | 1 | 1 |
| Vulcanization accelerator 1 | 1.5 | 1.5 | 1.5 |
| Vulcanization accelerator 2 | 1.5 | 1.5 | 0.5 |
| Evaluation | | | |
| Fuel efficiency | 100 | 102 | 103 |
| Abrasion resistance | 100 | 98 | 102 |
| Wet grip performance | 100 | 98 | 102 |
| On-ice performance | 100 | 98 | 102 |

| | EXAMPLES | | | | | | COM. EX. |
|---|---|---|---|---|---|---|---|
| | 52 | 53 | 54 | 55 | 56 | 57 | 36 |
| Compounded amount (part by mass) Step X1 | | | | | | | |
| NR | — | — | — | — | — | — | — |
| BR 1 | 60 | — | — | — | — | — | — |
| BR 3 | — | 60 | 60 | 60 | 60 | 60 | 60 |
| Silica 1 | 80 | 80 | 80 | 80 | 20 | 80 | 80 |
| Carbon black 1 | 5 | 5 | 5 | 5 | 5 | 5 | 5 |
| Oil 2 | 30 | 30 | 30 | 30 | 5 | 30 | 30 |
| Stearic acid | 2 | 2 | 2 | 2 | 2 | 2 | 2 |
| Wax | 2 | 2 | 2 | 2 | 2 | 2 | 2 |
| Surfactant | — | — | — | 1 | — | 2 | 1 |

TABLE 9-continued

| | | | | | | | |
|---|---|---|---|---|---|---|---|
| Vulcanization accelerator 2 | — | — | 1 | 1 | — | 1 | 1 |
| Coupling agent 1 | 6.4 | 6.4 | 6.4 | 6.4 | 1.6 | 6.4 | — |
| Coupling agent 2 | — | — | — | — | — | — | 6.4 |
| Step X2 | | | | | | | |
| NR | 40 | 40 | 40 | 40 | 40 | 40 | 40 |
| Silica 1 | 20 | 20 | 20 | 20 | 80 | 20 | 20 |
| Coupling agent 1 | 1.6 | 1.6 | 1.6 | 1.6 | 6.4 | 1.6 | — |
| Coupling agent 2 | — | — | — | — | — | — | 1.6 |
| Anti-aging agent | 2 | 2 | 2 | 2 | 2 | 2 | 2 |
| Zinc oxide | 2 | 2 | 2 | 2 | 2 | 2 | 2 |
| Step F | | | | | | | |
| Sulfur | 1 | 1 | 1 | 1 | 1.5 | 1.5 | 1 |
| Vulcanization accelerator 1 | 1.5 | 1.5 | 1.5 | 1.5 | 1.5 | 1.5 | 1.5 |
| Vulcanization accelerator 2 | 1.5 | 1.5 | 0.5 | 0.5 | 0.5 | 0.5 | 0.5 |
| Evaluation | | | | | | | |
| Fuel efficiency | 105 | 108 | 110 | 112 | 106 | 114 | 98 |
| Abrasion resistance | 104 | 106 | 108 | 111 | 102 | 109 | 97 |
| Wet grip performance | 105 | 108 | 110 | 110 | 106 | 110 | 97 |
| On-ice performance | 103 | 105 | 107 | 109 | 103 | 109 | 97 |

From the results of Table 9, it can be seen that fuel efficiency, abrasion resistance and wet grip performance can be improved in a good balance by producing a rubber composition for tire comprising a butadiene rubber (A1-9), an isoprene-based rubber (A2-9), silica (B-9), silica (B-9), carbon black (C-9), a specified coupling agent (D-9), a vulcanizer (E1-9) and a vulcanization accelerator (E2-9) by a specified production method.

Comparative examples and examples with reference to the tenth invention will be shown.

Comparative Examples 37 to 39

According to formulations shown in Tables 10 and 11, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at about 80° C. for 3 minutes (step F) to obtain an unvulcanized rubber composition. After that, tires for test were produced in the same manner as in Examples and the following evaluations were conducted. The results are shown in Tables 10 and 11.

Examples 58 to 63 and Comparative Example 40

According to formulations shown in Tables 10 and 11, the chemicals shown in the step X1 were kneaded with a 1.7 L Banbury mixer at the temperature at discharge of 150° C. for 5.0 minutes (step X1). After that, the kneaded product was held for one minute within the mixer such that the temperature at discharge became 160° C. Then, the kneaded product of the step X1 and chemicals shown in the step X2 were kneaded with a 1.7 L Banbury mixer at the temperature of not lower than 140° C. for 30 seconds and further kneaded at the temperature at discharge of 150° C. for 3 minutes (step X2). Then, the kneaded product of the step X2 and the chemicals shown in the step F were kneaded using an open roll at about 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 10 and Table 11.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 37 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 37 as 100. The larger the index is, the more excellent the abrasion resistance is.

(Abrasion resistance index)=(Running distance at which the depth of a groove of the tread portion of each tire for test was reduced for 1 mm)/(running distance at which the depth of a groove of the tread portion of tire for test of Comparative Example 37 was reduced for 1 mm)×100

<Wet Grip Performance Test>

On the wet road surface, a braking distance from an initial speed of 100 km/h was measured. The results are shown by index in accordance with the following formula, assuming the result of Comparative Example 37 as 100. The larger the index is, the more excellent the wet grip performance is.

(Index of wet grip performance)=(Braking distance of Comparative Example 37)/(braking distance of each Example)×100

<Electrical Conductivity Test>

A test piece of 15 cm×15 cm having a thickness of 2 mm was cut out of each of the tires for test and a volume specific resistivity was measured under conditions of an electrical voltage of 500 V, a temperature of 25° C., and a relative humidity of 50% using an electrical resistance meter R8340A manufactured by ADVANTEST Corporation. The evaluation results are shown by symbols according to the following criteria.

○: Volume specific resistivity of less than $1.0 \times 10^7$ Ω·cm
x: Volume specific resistivity of not less than $1.0 \times 10^7$ Ω·cm

TABLE 10

| | EXAMPLES | | | | | |
|---|---|---|---|---|---|---|
| | 58 | 59 | 60 | 61 | 62 | 63 |
| Compounded amount (part by mass) | | | | | | |
| Step X1 | | | | | | |
| NR | 40 | 40 | 40 | 40 | 40 | 40 |
| SBR 1 | 30 | — | — | — | — | — |
| SBR 3 | — | 30 | 30 | 30 | 30 | 30 |
| BR 1 | 30 | — | — | — | — | — |
| BR3 | — | 30 | 30 | 30 | 30 | 30 |
| Silica 1 | 60 | 60 | 60 | 60 | 15 | 60 |
| Carbon black 1 | 8 | 8 | 8 | 8 | 8 | 8 |
| Carbon black 2 | — | — | — | — | — | — |
| Oil 2 | 30 | 30 | 30 | 30 | 30 | 30 |
| Stearic acid | 2 | 2 | 2 | 2 | 2 | 2 |
| Wax | 2 | 2 | 2 | 2 | 2 | 2 |
| Surfactant | — | — | — | 1 | — | 2 |
| Vulcanization accelerator 2 | — | — | 1 | 1 | — | 1 |
| Coupling agent 1 | 4.8 | 4.8 | 4.8 | 4.8 | 1.2 | 4.8 |
| Coupling agent 2 | — | — | — | — | — | — |
| Step X2 | | | | | | |
| Silica 1 | 15 | 15 | 15 | 15 | 60 | 15 |
| Carbon black 2 | 3 | 3 | 3 | 3 | 3 | 3 |
| Coupling agent 1 | 1.2 | 1.2 | 1.2 | 1.2 | 4.8 | 1.2 |
| Coupling agent 2 | — | — | — | — | — | — |
| Anti-aging agent | 2 | 2 | 2 | 2 | 2 | 2 |
| Zinc oxide | 2 | 2 | 2 | 2 | 2 | 2 |
| Step F | | | | | | |
| Sulfur | 1.5 | 1.5 | 1.5 | 1.5 | 1.5 | 1.5 |
| Vulcanization accelerator 1 | 1.5 | 1.5 | 1.5 | 1.5 | 1.5 | 1.5 |
| Vulcanization accelerator 2 | 1.5 | 1.5 | 0.5 | 0.5 | 1.5 | 0.5 |
| Evaluation | | | | | | |
| Fuel efficiency | 107 | 113 | 118 | 125 | 108 | 128 |
| Abrasion resistance | 109 | 107 | 116 | 119 | 105 | 110 |
| Wet grip performance | 107 | 108 | 119 | 120 | 105 | 119 |
| Electrical conductivity | ○ | ○ | ○ | ○ | ○ | ○ |

TABLE 11

| | COM. EX. | | | COM. EX. |
|---|---|---|---|---|
| | 37 | 38 | 39 | 40 |
| Compounded amount (part by mass) | | | | |
| Step X / Step X1 | | | | |
| NR | 40 | 40 | 40 | 40 |
| SBR 1 | 30 | — | — | — |
| SBR 3 | — | 30 | 30 | 30 |
| BR 1 | 30 | — | — | — |
| BR 3 | — | 30 | 30 | 30 |
| Silica 1 | 75 | 75 | 75 | 60 |
| Carbon black 1 | 8 | 8 | 8 | 8 |
| Carbon black 2 | 3 | 3 | 3 | — |
| Oil 2 | 30 | 30 | 30 | 30 |
| Stearic acid | 2 | 2 | 2 | 2 |
| Wax | 2 | 2 | 2 | 2 |
| Surfactant | — | — | 1 | 1 |
| Vulcanization accelerator 2 | — | — | 1 | 1 |
| Coupling agent 1 | 6 | 6 | 6 | — |
| Coupling agent 2 | — | — | — | 4.8 |
| Step X2 | | | | |
| Silica 1 | — | — | — | 15 |
| Carbon black 2 | — | — | — | 3 |
| Coupling agent 1 | — | — | — | — |
| Coupling agent 2 | — | — | — | 1.2 |
| Anti-aging agent | 2 | 2 | 2 | 2 |
| Zinc oxide | 2 | 2 | 2 | 2 |
| Step F | | | | |
| Sulfur | 1.5 | 1.5 | 1.5 | 1.5 |
| Vulcanization accelerator 1 | 1.5 | 1.5 | 1.5 | 1.5 |
| Vulcanization accelerator 2 | 1.5 | 1.5 | 0.5 | 0.5 |
| Evaluation | | | | |
| Fuel efficiency | 100 | 103 | 103 | 96 |
| Abrasion resistance | 100 | 94 | 98 | 97 |
| Wet grip performance | 100 | 100 | 97 | 96 |
| Electrical conductivity | x | x | x | ○ |

From the results of Table 10 and Table 11, it can be seen that fuel efficiency, abrasion resistance, wet grip performance and electrical conductivity can be improved in a good balance by producing a rubber composition for tire comprising a specified rubber component (A-10), silica (B-10), carbon black 1 (C1-10), carbon black 2 (C2-10), a specified coupling agent (D-10), a vulcanizer (E1-10) and a vulcanization accelerator (E2-10) by a specified production method.

Comparative examples and examples with reference to the eleventh invention will be shown.

Comparative Examples 41 to 43

According to formulations shown in Table 12, all of the chemicals other than the vulcanizer (E1) and vulcanization accelerator (E2) were kneaded with a 1.7 L Banbury mixer at the temperature at discharge of 150° C. for 5 minutes (step X). Then, the kneaded product of the step X, the vulcanizer (E1) and the vulcanization accelerator (E2) were kneaded using an open roll at about 80° C. for 3 minutes (step F) to obtain an unvulcanized rubber composition. After that, tires for test were produced in the same manner as in Examples and the following evaluations were conducted. The results are shown in Table 12.

Examples 64 to 69 and Comparative Example 44

According to formulations shown in Table 12, the chemicals shown in the step X1 were kneaded with a 1.7 L Banbury mixer at the temperature at discharge of 150° C. for 5.0 minutes (step X1). After that, the kneaded product was held for one minute within the mixer such that the temperature at discharge became 160° C. Then, the kneaded product of the step X1 and chemicals shown in the step X2 were kneaded with a 1.7 L Banbury mixer at the temperature of not lower than 140° C. for 30 seconds and further kneaded at the temperature at discharge of 145° C. for 3 minutes (step X2). Then, the kneaded product of the step X2 and the chemicals shown in the step F were kneaded using an open roll at about 80° C. for 3 minutes (step F) to obtain an unvulcanized rubber composition. The obtained unvulcanized rubber composition was formed into the shape of a tread, laminated with other components of the tire in a tire building machine and vulcanized for 35 minutes under a condition of 150° C. and 25 kgf to obtain tires for test (tire size: 195/65R15). With respect to the obtained tires for test, the following evaluations were conducted. The results are shown in Table 12.

<Fuel Efficiency Test>

Rolling resistance of tires for test when each tire was run under conditions of a rim (15×6JJ), an inner pressure (230 kPa), a load (3.43 kN) and a speed (80 km/h) was measured with a rolling resistance testing machine and results are shown by index, assuming the result of Comparative Example 41 as 100. The larger the index is, the more excellent the fuel efficiency is.

<Abrasion Resistance Test>

Each of the test tires was loaded on the whole wheels of a real vehicle for test (domestically produced FF vehicle, displacement: 2000 cc), followed by the running on a dry asphalt road for 8000 km. The depth of a groove of the tread portion of tire was measured and the running distance at which the depth of a groove of the tread portion of tire was reduced for 1 mm was calculated. The results are shown by index in accordance with the following formula, assuming the result of Comparative Example 41 as 100. The larger the index is, the more excellent the abrasion resistance is.

(Index of abrasion resistance)=(Running distance at which the depth of a groove of the tread portion of each tire for test was reduced for 1 mm)/(running distance at which the depth of a groove of the tread portion of tire for test of Comparative Example 41 was reduced for 1 mm)×100

<Wet Grip Performance Test>

On the wet road surface, a braking distance from an initial speed of 100 km/h was measured. The results are shown by index in accordance with the following formula, assuming the result of Comparative Example 41 as 100. The larger the index is, the more excellent the wet grip performance is.

(Index of wet grip performance)=(Braking distance of Comparative Example 41)/(braking distance of each Example)×100

<Steering Stability Test>

The tires for test were loaded on the whole wheels of a real vehicle for test (domestically produced FF vehicle, displacement: 2000 cc), followed by meandering. During the meandering, the stability of control of steering was evaluated by a sensorial evaluation of a test driver and the results are shown by index, assuming the steering stability of Comparative Example 41 as 100. The larger the index is, the more excellent the steering stability is.

TABLE 12

| | COMPARATIVE EXAMPLES | | |
|---|---|---|---|
| | 41 | 42 | 43 |
| Compounded amount (part by mass) | | | |
| Step X | | | |
| SBR 1 | 70 | — | — |
| SBR 3 | — | 70 | 70 |
| BR 1 | 30 | — | — |
| BR 3 | — | 30 | 30 |
| Silica 1 | 60 | 60 | 60 |
| Carbon black 1 | 5 | 5 | 5 |
| Oil 2 | 5 | 5 | 5 |
| Stearic acid | 2 | 2 | 2 |
| Wax | 2 | 2 | 2 |
| Surfactant | — | — | 1 |
| Vulcanization accelerator 2 | — | — | 1 |
| Coupling agent 1 | 3.6 | 3.6 | 3.6 |
| Coupling agent 3 | 1.2 | 1.2 | 1.2 |
| Silica 1 | — | — | — |
| Coupling agent 1 | — | — | — |
| Coupling agent 3 | — | — | — |
| Anti-aging agent | 2 | 2 | 2 |
| Zinc oxide | 2 | 2 | 2 |
| Step F | | | |
| Sulfur | 1.5 | 1.5 | 1.5 |
| Vulcanization accelerator 1 | 1.5 | 1.5 | 1.5 |
| Vulcanization accelerator 2 | 1.5 | 1.5 | 0.5 |
| Evaluation | | | |
| Fuel efficiency | 100 | 103 | 103 |
| Abrasion resistance | 100 | 98 | 93 |
| Wet grip performance | 100 | 101 | 98 |
| Steering stability | 100 | 98 | 94 |

TABLE 12-continued

| | EXAMPLES | | | | | | COM. EX. |
|---|---|---|---|---|---|---|---|
| | 64 | 65 | 66 | 67 | 68 | 69 | 44 |
| Compounded amount (part by mass) Step X1 | | | | | | | |
| SBR 1 | 70 | — | — | — | — | — | — |
| SBR 3 | — | 70 | 70 | 70 | 70 | 70 | 70 |
| BR 1 | 30 | — | — | — | — | — | — |
| BR 3 | — | 30 | 30 | 30 | 30 | 30 | 30 |
| Silica 1 | 45 | 45 | 45 | 45 | 15 | 45 | 45 |
| Carbon black 1 | 5 | 5 | 5 | 5 | 5 | 5 | 5 |
| Oil 2 | 5 | 5 | 5 | 5 | 5 | 5 | 5 |
| Stearic acid | 2 | 2 | 2 | 2 | 2 | 2 | 2 |
| Wax | 2 | 2 | 2 | 2 | 2 | 2 | 2 |
| Surfactant | — | — | — | 1 | — | 2 | 1 |
| Vulcanization accelerator 2 | — | — | 1 | 1 | — | 1 | 1 |
| Coupling agent 1 | 3.6 | 3.6 | 3.6 | 3.6 | 1.2 | 3.6 | — |
| Coupling agent 3 | — | — | — | — | — | — | 3.6 |
| Step X2 | | | | | | | |
| Silica 1 | 15 | 15 | 15 | 15 | 45 | 15 | 15 |
| Coupling agent 1 | — | — | — | — | — | — | — |
| Coupling agent 3 | 1.2 | 1.2 | 1.2 | 1.2 | 3.6 | 1.2 | 1.2 |
| Anti-aging agent | 2 | 2 | 2 | 2 | 2 | 2 | 2 |
| Zinc oxide | 2 | 2 | 2 | 2 | 2 | 2 | 2 |
| Step F | | | | | | | |
| Sulfur | 1.5 | 1.5 | 1.5 | 1.5 | 1.5 | 1.5 | 1.5 |
| Vulcanization accelerator 1 | 1.5 | 1.5 | 1.5 | 1.5 | 1.5 | 1.5 | 1.5 |
| Vulcanization accelerator 2 | 1.5 | 1.5 | 0.5 | 0.5 | 1.5 | 0.5 | 1.5 |
| Evaluation | | | | | | | |
| Fuel efficiency | 105 | 110 | 115 | 120 | 108 | 122 | 95 |
| Abrasion resistance | 105 | 107 | 111 | 120 | 106 | 112 | 97 |
| Wet grip performance | 105 | 108 | 112 | 116 | 107 | 115 | 100 |
| Steering stability | 105 | 105 | 113 | 116 | 104 | 115 | 98 |

From the results of Table 12, it can be seen that fuel efficiency, abrasion resistance and wet grip performance can be improved in a good balance by producing a rubber composition for tire comprising a specified rubber component (A-11), silica (B-11), carbon black (C-11), a specified coupling agent (D1-11), a coupling agent having a sulfide group (D2-11), a vulcanizer (E1-11) and a vulcanization accelerator (E2-11) by a specified production method.

From the results of Tables 1 to 12, it can be seen that a rubber composition for tire in which fuel efficiency and abrasion resistance are improved in a good balance can be produced according to the production method of a rubber composition for tire of the present invention comprising a rubber component (A) comprising at least one selected from the group consisting of a natural rubber and a synthetic diene rubber, a filler, a coupling agent (D) represented by the following chemical formula (1), and a vulcanizing agent (E) comprising a vulcanizer and a vulcanization accelerator, the method comprising:

(step X1) a step X1 of kneading all amount of A, a part of the filler and a part of D, (step X2) a step X2 of kneading the kneaded product of step X1, the remaining amount of the filler and D, and (step F) a step F of kneading the kneaded product of step X2 and E.

The invention claimed is:

1. A production method of a rubber composition for a tire comprising a rubber component (A) comprising at least one selected from the group consisting of a natural rubber and a synthetic diene rubber, silica (B), carbon black (C), a coupling agent (D1) represented by the following chemical formula (1), a coupling agent (D2) selected from the list below, and a vulcanizing agent (E) comprising a vulcanizer and a vulcanization accelerator, the method comprising:

(step X1) a step X1 of kneading all of an amount of A, a part of an amount of B, all of an amount of D1, optionally a part or all of an amount of C, and optionally a part of an amount of E, (step X2) a step X2 of kneading the kneaded product of step X1, and the remaining amount of B, all of an amount of D2, optionally a part or all of an amount of C, and optionally a part of the amount of E, and (step F) a step F of kneading the kneaded product of step X2 and the remaining amount of E, wherein some remaining amount of E is available for step F, and

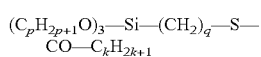

Chemical formula (1):

wherein p represents an integer of 1 to 3, q represents an integer of 1 to 5, and k represents an integer of 5 to 12; and (D2) is selected from the following list: bis(3-triethoxysilylpropyl)tetrasulfide, bis(2-triethoxysilylethyl)tetrasulfide, bis(3-trimethoxysilylpropyl)tetrasulfide, bis(2-trimethoxysilylethyl)tetrasulfide, bis(3-triethoxysilylpropyl)trisulfide, bis(3-trimethoxysilylpropyl)trisulfide, bis(3-triethoxysilylpropyl)disulfide, bis(3-trimethoxysilylpropyl)disulfide, 3-trimethoxysilylpropyl-N,N-dimethylthiocarbamoyl tetrasulfide, 3-triethoxysilylpropyl-N,N-dimethylthiocarbamoyl tetrasulfide, 2-triethoxysilylethyl-N,N-dimethylthiocarbamoyl tetrasulfide, 2-trimethoxysilylethyl-N,N-dimethylthiocarbamoyl tetrasulfide, 3-trimethoxysilylpropylbenzothiazolyl tetrasulfide, 3-triethoxysilylpropylbenzothiazole tetrasulfide, 3-triethoxysilylpropyl methacrylate monosulfide, and 3-trimethoxysilylpropyl methacrylate monosulfide.

2. The production method of claim 1, wherein the rubber component comprises a styrene butadiene rubber and/or a butadiene rubber which has a functional group that reacts with silica.

3. The production method of claim 1, wherein the rubber composition further comprises a plasticizer and not less than 50% by mass of the total added amount of the plasticizer is kneaded in the step X1.

4. The production method of claim 1, wherein the rubber composition further comprises an anti-aging agent and the anti-aging agent is kneaded in the step X2.

5. A tire having a tire component composed of a rubber composition for tire produced by the production method of claim 1.

6. The production method of claim 1, wherein the added amount of the coupling agent in each of the step X1 and the step X2 is 4 to 10 parts by mass based on 100 parts by mass of the silica added in each step.

7. The production method of claim 1, wherein the added amount of the silica in the step X1 is 50 to 95% by mass of the total added amount of silica.

8. The production method of claim 1, wherein the highest temperature in the step X1 is 140° C. to 200° C.

9. The production method of claim 1, wherein after the kneading in the step X1 is finished, the production method comprises a step of maintaining the kneaded product at 150 to 190° C. for 10 to 120 seconds.

10. The production method of claim 1, wherein a part or all amount of the vulcanization accelerator is kneaded in the step X1 and/or the step X2.

11. The production method of claim 1, wherein the production method is a production method of the rubber composition further comprising a surfactant and a surfactant is kneaded in the step X1 and/or the step X2.

* * * * *